US009657046B2

(12) United States Patent
Umetsu et al.

(10) Patent No.: US 9,657,046 B2
(45) Date of Patent: May 23, 2017

(54) METHODS FOR THE TREATMENT AND PREVENTION OF INFLAMMATORY DISEASES

(75) Inventors: Dale T. Umetsu, Newton, MA (US); Rosemarie H. De Kruyff, Newton, MA (US); Ya-Jen Chang, Brookline, MA (US); Petr Illarionov, Birmingham (GB)

(73) Assignees: Children's Medical Center Corporation, Boston, MA (US); University of Birmingham, Birmingham (GB)

( * ) Notice: Subject to any disclaimer, the term of this patent is extended or adjusted under 35 U.S.C. 154(b) by 777 days.

(21) Appl. No.: 13/699,436

(22) PCT Filed: May 24, 2011

(86) PCT No.: PCT/US2011/037664
§ 371 (c)(1),
(2), (4) Date: Jun. 7, 2013

(87) PCT Pub. No.: WO2011/149881
PCT Pub. Date: Dec. 1, 2011

(65) Prior Publication Data
US 2014/0301996 A1 Oct. 9, 2014

Related U.S. Application Data

(60) Provisional application No. 61/421,797, filed on Dec. 10, 2010, provisional application No. 61/347,596, filed on May 24, 2010.

(51) Int. Cl.
| | | |
|---|---|---|
| *A61K 31/704* | (2006.01) | |
| *A61K 31/56* | (2006.01) | |
| *C07H 15/24* | (2006.01) | |
| *A61K 31/70* | (2006.01) | |
| *A61K 35/15* | (2015.01) | |
| *A61K 35/17* | (2015.01) | |
| *A61K 39/00* | (2006.01) | |

(52) U.S. Cl.
CPC ............. *C07H 15/24* (2013.01); *A61K 31/56* (2013.01); *A61K 31/70* (2013.01); *A61K 31/704* (2013.01); *A61K 35/15* (2013.01); *A61K 35/17* (2013.01); *A61K 2039/572* (2013.01)

(58) Field of Classification Search
CPC ........ A61K 35/15; A61K 35/17; A61K 31/56; A61K 31/70; A61K 31/704
USPC ........................................................ 514/26
See application file for complete search history.

(56) References Cited

U.S. PATENT DOCUMENTS

| | | | |
|---|---|---|---|
| 3,966,918 A | 6/1976 | Kawamata et al. | |
| 2006/0116331 A1* | 6/2006 | Jiang | C07H 15/00 514/25 |
| 2006/0116332 A1* | 6/2006 | Strober | A61K 31/164 514/25 |
| 2009/0227781 A1 | 9/2009 | Miyake et al. | |

FOREIGN PATENT DOCUMENTS

| | | |
|---|---|---|
| EP | 0162330 A1 | 11/1985 |
| EP | 1837345 A1 | 9/2007 |
| JP | 2000026495 A | 1/2000 |
| JP | 2003073278 A | 3/2003 |
| WO | 2004028475 A2 | 4/2004 |

OTHER PUBLICATIONS

Yoshikazu Hirai et al., "Unique Cholesteryl Glucosides in Helicobacter pylon: Composition and Structural Analysis", J Bacteriology, 1995, 177(18). pp. 5327-5333.
International Search Report for PCT/US2011/037664 mailed Jan. 17, 2012.
Patricia Hachern et al.; "Frontline: a-Galactosylceramide-induced iNKT cells suppress experimental allergic asthma in sensitized mice: Role of IFN-c", Oct. 1, 2005, XP055092438, Retrieved from the Internet: URL:http://onlinelibrary.wiley.com/store/10.1002/eji.200535268/asset/2793_ftp.pdf?v=1&t=hp0vseqw &s=36da291clbe3959fec09595bbfc51c3d22bble77 [retrieved on Dec. 10, 2013].
Ito Yuki et al.; "Cholesteryl alpha-Glucosides of Helicobacter pylori Play Critical Roles in Bacterial Growth and Innate Immunity by Invariant Natural Killer T Cells", Glycobiology, Oxford Univeristy Press, US, vol. 20, No. 11, Nov. 10, 2010, p. 1461.
"Natural killer T cells and the regulation of asthma", Mucosal Immunology: Nature Publishing Group, vol. 2, No. 5, Sep. 1, 2009.

(Continued)

*Primary Examiner* — Jennifer M Kim
(74) *Attorney, Agent, or Firm* — Mintz Levin Cohn Ferris Glovsky and Popeo, P.C.; Peter F. Corless; Christopher R. Cowles

(57) ABSTRACT

The inventors demonstrate that treatment of young, suckling mice with a glycolipid derived from *Helicobacter pylori* activates NKT cells in a CD1d-restricted fashion, and is protective against AHR in a model of allergen-induced asthma. The inventors further found that this protective effect can be transferred by NKT cells exposed to the glycolipid, and is associated with the expansion of a suppressive double-negative NKT cells and Foxp3$^+$ T$_{Reg}$ cells. The inventors also demonstrate herein that pre-treatment of adult mice with a glycolipid derived from *Helicobacter pylori* partially suppresses airway hyperreactivity and inhibits BAL inflammation in an ozone-exposure model. Accordingly, provided herein are compositions and methods for the treatment and prevention of inflammatory diseases, such as asthma or autoimmune diseases, in a subject in need thereof.

21 Claims, 59 Drawing Sheets

(56) References Cited

OTHER PUBLICATIONS

Extended European Search Report for corresponding European Application Ser. No. 11787213.5, Mar. 1, 2014, 17 pages.

* cited by examiner

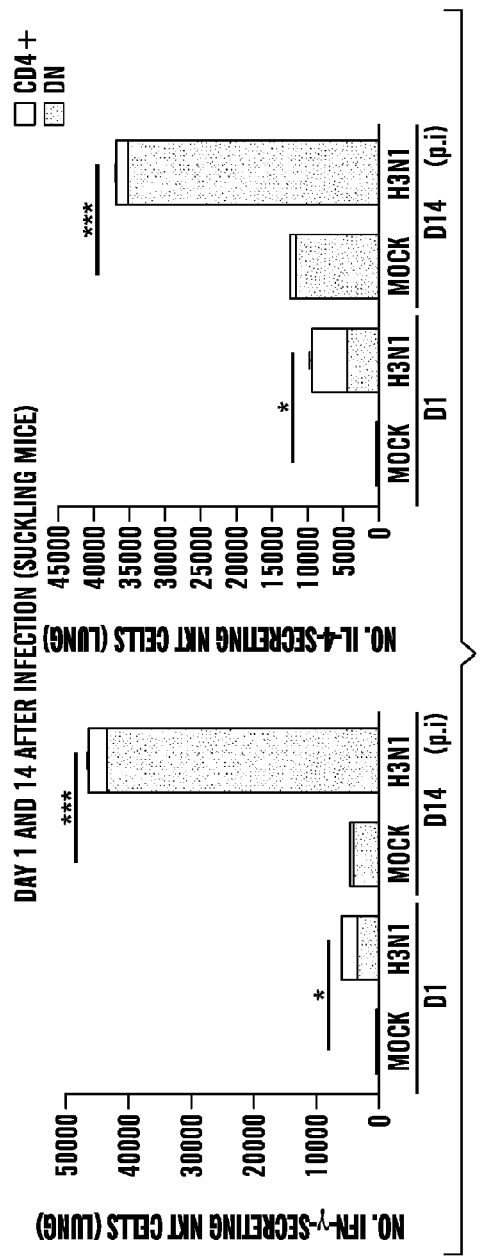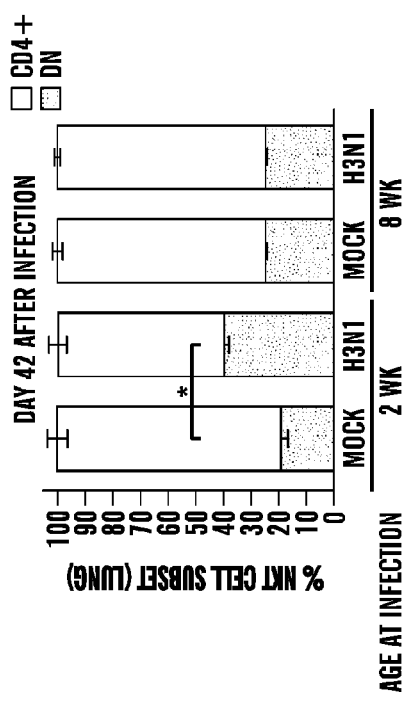
FIG. 3E
FIG. 3F

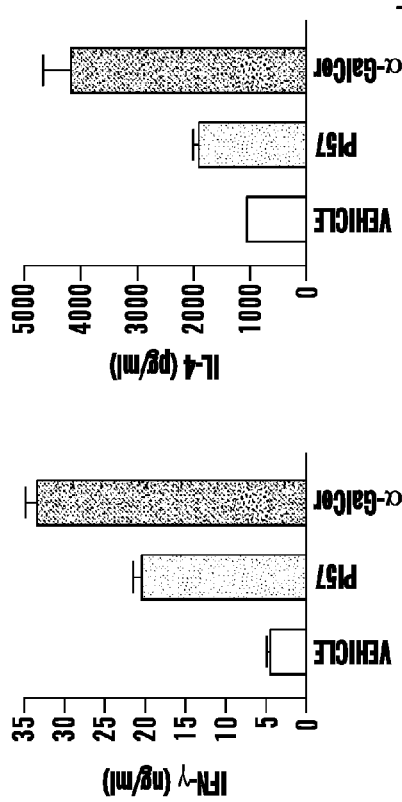
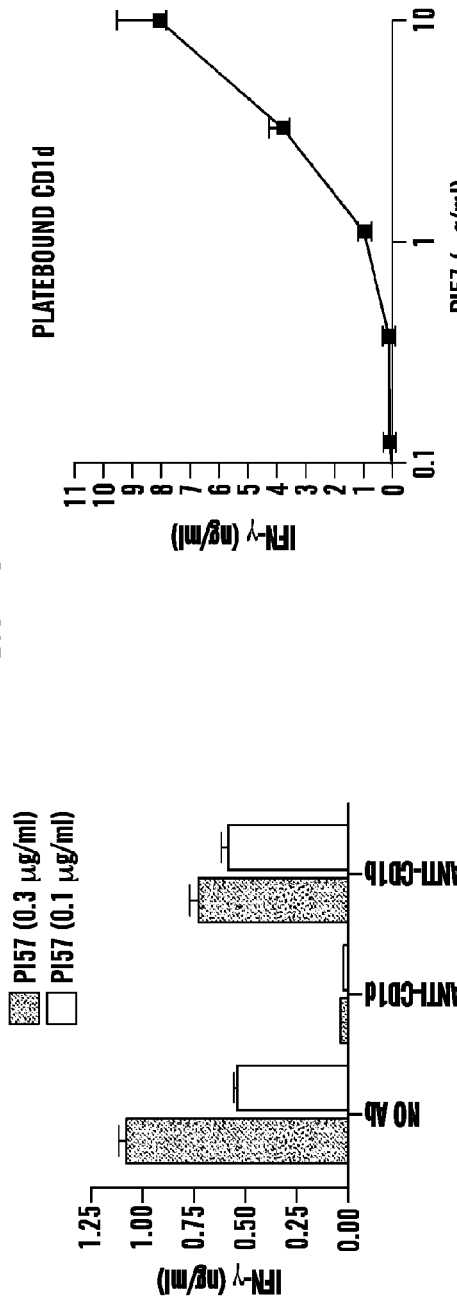
FIG. 7E
FIG. 7F
FIG. 7G

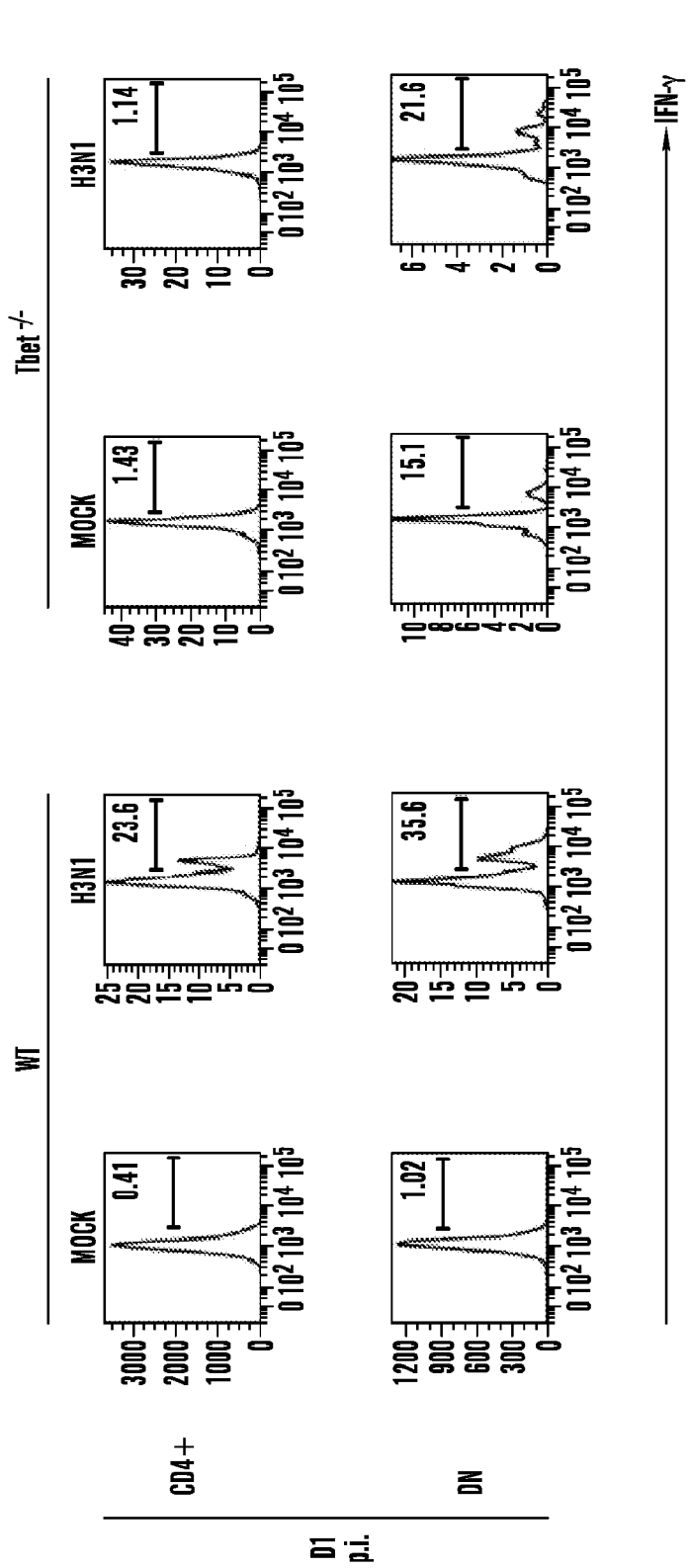

METHODS FOR THE TREATMENT AND PREVENTION OF INFLAMMATORY DISEASES

CROSS-REFERENCE TO RELATED APPLICATIONS

This application is a 35 U.S.C. §371 National Phase Entry Application of co-pending International Application No. PCT/US2011/037664 filed May 24, 2011, which designates the U.S., and which claims the benefit of priority under 35 U.S.C. §119(e) of U.S. Provisional Patent Application Ser. No. 61/421,797 filed on Dec. 10, 2010 and U.S. Provisional Patent Application Ser. No. 61/347,596 filed on May 24, 2010, the contents of each of which are incorporated herein in their entireties by reference.

GOVERNMENT SUPPORT

The invention was made with Government support under grants R01 AI68085, R01 HL62348, R01 AI026322, and RC1HL069507 awarded by the National Institutes of Health (NIH). The Government has certain rights in the invention.

FIELD OF THE INVENTION

The present invention relates to methods and glycolipid compounds for the treatment of inflammatory disease, such as asthma and autoimmune diseases.

BACKGROUND OF THE INVENTION

Bronchial asthma, a complex and heterogeneous trait, is a major public health problem, affecting nearly 10% of the general population, and disproportionately affecting children. Moreover, the prevalence of asthma has increased dramatically over the past three decades, an increase thought to be due to changes in our environment. These environmental changes include reductions in the incidence of infectious diseases that may exert protective effects against asthma, as suggested by the Hygiene Hypothesis[1]. While the infectious agents responsible for this relationship, and the precise mechanisms by which infectious microorganisms might protect against asthma are very poorly understood, epidemiological studies suggest that infection with bacteria (e.g., *Helicobacter pylori* (2,3), endotoxin (4), or *Acinetobacter lwoffi* (5) or viruses (e.g., hepatitis A virus (6,7)) can reduce the likelihood of developing asthma.

The role of viral infection in modulating the development of asthma is particularly complex, because many different viruses affect the respiratory tract, some appearing to enhance and some appearing to protect against the development of asthma. For example, infection with human rhinovirus in children before three years of age increases the later risk of developing asthma (8), while other respiratory viral infections appear to protect against the later development of asthma (9-14). However, in older individuals with established asthma, respiratory viral infection, particularly with rhinovirus and also with influenza A virus, almost always triggers acute symptoms of asthma (15-17). These discrepancies, without wishing to be bound or limited by theory, may be due to the timing of the infection, since infection in very young children may profoundly alter the developing innate immune system in such a way as to protect against the later development of asthma, or to the specific immunological cell types activated by a given infectious agent.

In asthma, a population of innate immune cells known as natural killer T (NKT) cells have been suggested to play a very important pathogenic role (20, 47). Some patients, particularly those with mild or well-controlled asthma, have few detectable pulmonary NKT cells, while patients with severe, poorly controlled asthma have a significant increase in pulmonary NKT cells (19, 48, 49). In many distinct mouse models of asthma, the presence of specific NKT cell subsets have been shown to be required for the development of airway hyperreactivity (AHR), a cardinal feature of asthma. For example, in an allergen-induced AHR model, $CD4^+IL-17RB^+$ NKT cells are required (19, 20, 50, 51); in an ozone-induced AHR model, an $NK1.1^-$, IL-17 producing subset is required (21); and in a Sendai virus-induced AHR model, a $CD4^+$ NKT cell population that interacts with alternatively activated alveolar macrophages is required (22).

Recent evidence indicates that NKT cells participate in immune responses to a growing list of infectious microorganisms. These immune responses can be driven either by direct TCR recognition of specific glycolipids expressed by microorganisms, as in the case of *Borrelia burgdorferi* (39) and *Sphingomonas paucimobilis* (32, 40), or by indirect responses to cytokines released by activated dendritic cells (DCs), as in the case of *Salmonella typhimurium* (41), *E. coli*, *S. aureus* and *L. monocytogenes* (42), and *Mycobacteria tuberculosis* (43, 44). Thus, NKT cells have been implicated both in enhancing protective immunity to a diverse group of pathogens, as well as in enhancing or causing pathogenic immune responses, such as those found in asthma or autoimmune disorders.

SUMMARY OF THE INVENTION

As described herein, the inventors demonstrate that immunological exposure to viruses and bacteria at a young age can provide protection against the later initiation of allergic asthma, and that this protective effect can be transferred via NKT cells. The inventors demonstrate that treatment of young, suckling mice with a glycolipid derived from *Helicobacter pylori* (a bacterium associated with protection against asthma), activates NKT cells in a CD1d-restricted fashion, and is protective against AHR in a model of allergen-induced asthma. The inventors further found that this protective effect can be transferred by NKT cells exposed to the glycolipid, and is associated with the expansion of a suppressive double-negative NKT cells and $Foxp3^+$ $T_{Reg}$ cells. The inventors also demonstrate herein that pre-treatment of adult mice with the glycolipid derived from *Helicobacter pylori* partially suppresses airway hyperreactivity and inhibits BAL inflammation in an ozone-exposure model. The inventors further demonstrate that young, suckling mice infected with influenza A are protected as adults against allergen-induced airway hyperreactivity (AHR). The protective effect was associated with the preferential expansion of $CD4^-CD8^-$, but not $CD4^+$, natural killer T (NKT) cells, and required T-bet and TLR7. Adoptive transfer of this population into allergen-sensitized adult mice suppressed the development of allergen-induced AHR, while expanding allergen-specific $Foxp3^+$ $T_{Reg}$ cells. The findings discovered by the inventors provide novel regulatory pathways, and new therapeutic strategies for the prevention and treatment of inflammatory diseases requiring immune regulation and suppression, such as asthma and autoimmune diseases.

Accordingly, in one aspect, a method for the treatment or prevention of an inflammatory disease in a subject in need thereof is provided, comprising administering to a subject having an inflammatory disease an effective amount of a compound of formula (I):

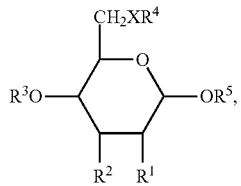

FORMULA (I)

wherein:

$R^1$ is $OR^3$, $NH_2$, or NHC(O)-alkyl, or together with $R^2$ forms a second bond between the carbons they are attached to;

$R^2$ is $OR^3$ or together with $R^1$ forms a second bond between the carbons they are attached to;

$R^3$ and $R^4$ are independently H, alkyl, alkenyl, alkynyl, acyl, $PO_3^{2-}$, each of which may be optionally substituted;

$R^5$ is

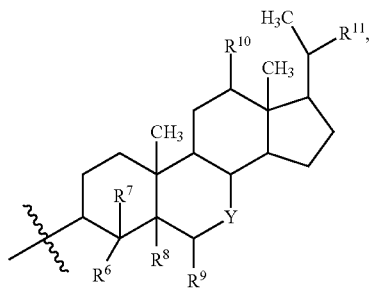

alkyl, alkenyl, alkynyl, or acyl, each of which may be optionally substituted;

$R^6$ and $R^7$ are both H or both alkyl;

$R^8$ is H or together with $R^9$ forms a second bond between the carbons to which they are attached;

$R^9$ is H, $OR^3$, or together with $R^8$ forms a second bond between the carbons to which they are attached;

$R^{10}$ is H, OH, alkyl, or O-alkyl, each of which may be optionally substituted;

$R^{11}$ is alkyl, alkenyl, or alkynyl, each of which may be optionally substituted;

X is O, or NH;

Y is $CH_2$, C(O), or $CHOR^3$; and pharmaceutically acceptable salts thereof.

In some embodiments of the aspect, the method further comprises administering an effective amount of antigen presenting cells (APCs).

Another aspect provides a method for the treatment or prevention of an inflammatory disease in a subject in need thereof, comprising administering to a subject having an inflammatory disease an NKT cell population contacted with an effective amount of a compound of formula (I):

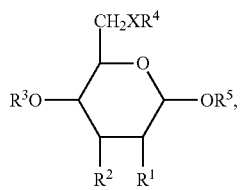

FORMULA (I)

wherein:

$R^1$ is $OR^3$, $NH_2$, or NHC(O)-alkyl, or together with $R^2$ forms a second bond between the carbons they are attached to;

$R^2$ is $OR^3$ or together with $R^1$ forms a second bond between the carbons they are attached to;

$R^3$ and $R^4$ are independently H, alkyl, alkenyl, alkynyl, acyl, $PO_3^{2-}$, each of which may be optionally substituted;

$R^5$ is

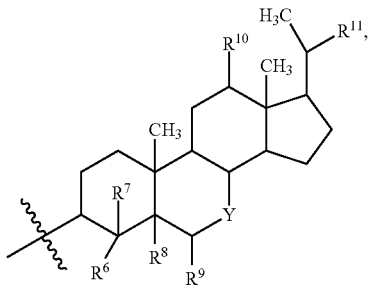

alkyl, alkenyl, alkynyl, or acyl, each of which may be optionally substituted;

$R^6$ and $R^7$ are both H or both alkyl;

$R^8$ is H or together with $R^9$ forms a second bond between the carbons to which they are attached;

$R^9$ is H, $OR^3$, or together with $R^8$ forms a second bond between the carbons to which they are attached;

$R^{10}$ is H, OH, alkyl, or O-alkyl, each of which may be optionally substituted;

$R^{11}$ is alkyl, alkenyl, or alkynyl, each of which may be optionally substituted;

X is O, or NH;

Y is $CH_2$, C(O), or $CHOR^3$; and pharmaceutically acceptable salts thereof.

In some embodiments of the aspect, the contacting of the NKT cell population with the compound of formula (I) occurs in vitro, ex vivo, or in vivo.

In some embodiments of the aspect, the contacting of the NKT cell population with the compound of formula (I) occurs in the presence of one or more antigen-presenting cells.

In some embodiments of the aspect, the NKT cells are allogeneic NKT cells obtained from one or more donors. In other embodiments of the aspect, the NKT cells are autologous NKT cells.

Another aspect of the invention provides a method for the treatment of an inflammatory disease in a subject in need thereof, the method comprising:

a) isolating a plurality of immune cells from a first subject, wherein the immune cells comprise an NKT population;

b) contacting said immune cells with an effective amount of a compound of formula (I):

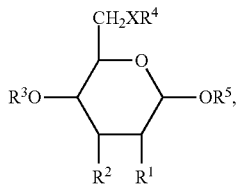

FORMULA (I)

wherein:
R$^1$ is OR$^3$, NH$_2$, or NHC(O)-alkyl, or together with R$^2$ forms a second bond between the carbons they are attached to;
R$^2$ is OR$^3$ or together with R$^1$ forms a second bond between the carbons they are attached to;
R$^3$ and R$^4$ are independently H, alkyl, alkenyl, alkynyl, acyl, PO$_3^{2-}$, each of which may be optionally substituted;
R$^5$ is

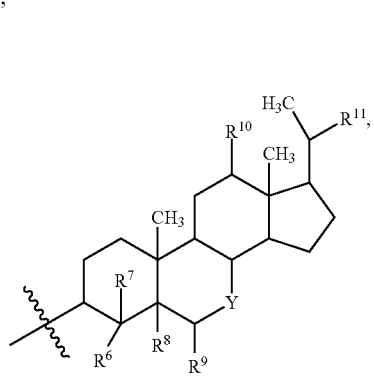

alkyl, alkenyl, alkynyl, or acyl, each of which may be optionally substituted;
R$^6$ and R$^7$ are both H or both alkyl;
R$^8$ is H or together with R$^9$ forms a second bond between the carbons to which they are attached;
R$^9$ is H, OR$^3$, or together with R$^8$ forms a second bond between the carbons to which they are attached;
R$^{10}$ is H, OH, alkyl, or O-alkyl, each of which may be optionally substituted;
R$^{11}$ is alkyl, alkenyl, or alkynyl, each of which may be optionally substituted;
X is O, or NH;
Y is CH$_2$, C(O), or CHOR$^3$; and
pharmaceutically acceptable salts thereof; and
c) administering to a second subject an effective amount of the plurality of immune cells contacted with a compound of formula (I), wherein said second subject has an inflammatory disease.

In some embodiments of the aspect, the immune cells are contacted with the compound of formula (I) in an amount and time sufficient to expand an NKT cell population in the plurality of immune cells.

Another aspect of the invention provides a method for the treatment of an inflammatory disease in a subject in need thereof, comprising:
a. administering to a first subject an effective amount of a compound of formula (I):

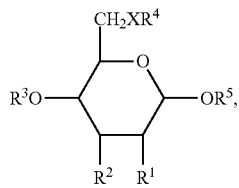

FORMULA (I)

wherein:
R$^1$ is OR$^3$, NH$_2$, or NHC(O)-alkyl, or together with R$^2$ forms a second bond between the carbons they are attached to;
R$^2$ is OR$^3$ or together with R$^1$ forms a second bond between the carbons they are attached to;
R$^3$ and R$^4$ are independently H, alkyl, alkenyl, alkynyl, acyl, PO$_3^{2-}$, each of which may be optionally substituted;
R$^5$ is

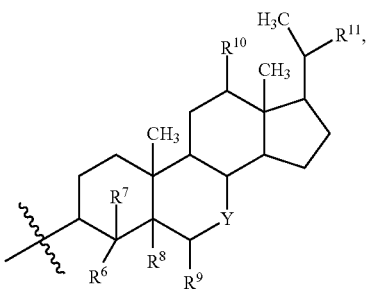

alkyl, alkenyl, alkynyl, or acyl, each of which may be optionally substituted;
R$^6$ and R$^7$ are both H or both alkyl;
R$^8$ is H or together with R$^9$ forms a second bond between the carbons to which they are attached;
R$^9$ is H, OR$^3$, or together with R$^8$ forms a second bond between the carbons to which they are attached;
R$^{10}$ is H, OH, alkyl, or O-alkyl, each of which may be optionally substituted;
R$^{11}$ is alkyl, alkenyl, or alkynyl, each of which may be optionally substituted;
X is O, or NH;
Y is CH$_2$, C(O), or CHOR$^3$; and
pharmaceutically acceptable salts thereof; and
b. isolating a plurality of immune cells from the first subject, wherein the immune cells comprise an NKT population; and
c. administering to a second subject an effective amount of the plurality of immune cells isolated from the first subject contacted with a compound of formula (I), wherein said second subject has an inflammatory disease.

In some embodiments of the aspect, the first and second subject are the same subject.

In some embodiments of the aspect, the first subject is a young subject or an infant subject. In some embodiment, the first subject is less than 10 years, less than 9 years, less than 8 years, less than 7 years, less than 6 years, less than 5 years, less than 4 years, less than 3 years, less than 2 years, less than 1 year, less than 11 months, less than 10 months, less than 9 months, less than 8 months, less than 7 months, less than 6 months, less than 5 months, less than 4 months, less than 3 months, less than 2 months, or less than 1 month of age.

In some embodiments of the aspect, the plurality of immune cells further comprise antigen-presenting cells.

In some embodiments of the aspect, the plurality of immune cells are isolated from the peripheral blood, bone marrow, thymus, or spleen of the first subject.

In some embodiments of the aspect, the method further comprises purifying or enriching for an NKT cell population from the plurality of immune cells prior to the administration of the plurality of immune cells to the second subject. In some embodiments, the purified NKT cell population has a CD4⁻CD8⁻ or double-negative phenotype.

In some embodiments of this aspect and all such aspects described herein, the compound of formula (I) is a compound of formula (II), formula (III), formula (IV) or formula (V).

In some embodiments of this aspect and all such aspects described herein, the compound of formula (I) is selected from the cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside; 7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate-α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O-tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6-bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside.

In some embodiments of this aspect and all such aspects described herein, the compound of formula (I) is cholesteryl 6-O-tetradecanoyl-α-D-glucopyranoside (also referred to herein as 6-O-acyl α-glucoside).

In some embodiments of this aspect and all such aspects described herein, the inflammatory disease is a respiratory disease or an autoimmune disease. In some such embodiments, the respiratory disease is selected from the group consisting of asthma, airway hyperreactivity, lung inflammation, chronic obstructive pulmonary disease, pneumonia, hypersensitivity pneumonitis, pulmonary infiltrate with eosinophilia, environmental lung disease, bronchiectasis, cystic fibrosis, interstitial lung disease, primary pulmonary hypertension, pulmonary thromboembolism, disorders of the pleura, acute respiratory distress syndrome, mesothelioma, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis. In some embodiments, the asthma is allergic or non-allergic asthma.

In some embodiments of this aspect and all such aspects described herein, the inflammatory disease is an autoimmune disease selected from the group consisting of type-I diabetes, multiple sclerosis, Hashinoto's thyroiditis, Crohn's disease, rheumatoid arthritis, systemic lupus erythromatosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

In another aspect, provided herein is a compound of formula (I) for use in treating or preventing an inflammatory disease in a subject in need thereof:

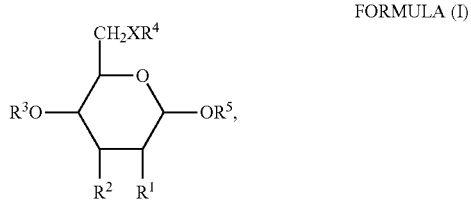

FORMULA (I)

wherein:
$R^1$ is $OR^3$, $NH_2$, or NHC(O)-alkyl, or together with $R^2$ forms a second bond between the carbons they are attached to;
$R^2$ is $OR^3$ or together with $R^1$ forms a second bond between the carbons they are attached to;
$R^3$ and $R^4$ are independently H, alkyl, alkenyl, alkynyl, acyl, $PO_3^{2-}$, each of which may be optionally substituted;
$R^5$ is

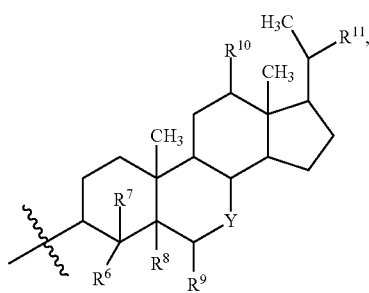

alkyl, alkenyl, alkynyl, or acyl, each of which may be optionally substituted;
$R^6$ and $R^7$ are both H or both alkyl;
$R^8$ is H or together with $R^9$ forms a second bond between the carbons to which they are attached;
$R^9$ is H, $OR^3$, or together with $R^8$ forms a second bond between the carbons to which they are attached;
$R^{10}$ is H, OH, alkyl, or O-alkyl, each of which may be optionally substituted;
$R^{11}$ is alkyl, alkenyl, or alkynyl, each of which may be optionally substituted;
X is O, or NH;
Y is $CH_2$, C(O), or $CHOR^3$; and
pharmaceutically acceptable salts thereof.

In some embodiments of the aspect, the use further comprises administering an effective amount of antigen presenting cells (APCs).

In some embodiments of the aspect, the use further comprises contacting a NKT cell population with the compound of formula (I) in vitro, ex vivo, or in vivo. In some such embodiments of the aspect, the contacting of the NKT cell population with the compound of formula (I) occurs in the presence of one or more antigen-presenting cells. In some such embodiments of the aspect, the NKT cells are allogeneic NKT cells obtained from one or more donors. In other embodiments of the aspect, the NKT cells are autologous NKT cells.

In some embodiments of this aspect and all such aspects described herein, the compound of formula (I) is a compound of formula (II), formula (III), formula (IV) or formula (V).

In some embodiments of this aspect and all such aspects described herein, the compound of formula (I) is selected from the cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside; 7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate- α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O-tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6-bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside.

In some embodiments of this aspect and all such aspects described herein, the compound of formula (I) is cholesteryl 6-O-tetradecanoyl-α-D-glucopyranoside (also referred to herein as 6-O-acyl α-glucoside).

In some embodiments of this aspect and all such aspects described herein, the inflammatory disease is a respiratory disease or an autoimmune disease. In some such embodiments, the respiratory disease is selected from the group consisting of asthma, airway hyperreactivity, lung inflammation, chronic obstructive pulmonary disease, pneumonia, hypersensitivity pneumonitis, pulmonary infiltrate with eosinophilia, environmental lung disease, bronchiectasis, cystic fibrosis, interstitial lung disease, primary pulmonary hypertension, pulmonary thromboembolism, disorders of the pleura, acute respiratory distress syndrome, mesothelioma, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis. In some embodiments, the asthma is allergic or non-allergic asthma.

In some embodiments of this aspect and all such aspects described herein, the inflammatory disease is an autoimmune disease selected from the group consisting of type-I diabetes, multiple sclerosis, Hashinoto's thyroiditis, Crohn's disease, rheumatoid arthritis, systemic lupus erythromatosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

In another aspect, provided herein is a method for the treatment or prevention of an inflammatory disease in a subject in need thereof, the method comprising administering to a subject having an inflammatory disease an effective amount of a compound of formula (VI):

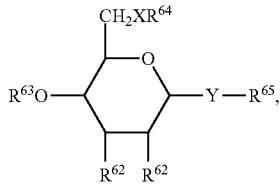

FORMULA (VI)

wherein:

$R^{61}$ is $OR^{63}$, $NH_2$, or NHC(O)-alkyl, or together with $R^{62}$ forms a second bond between the carbons they are attached to;

$R^{62}$ is $OR^{63}$ or together with $R^{61}$ forms a second bond between the carbons they are attached to;

$R^{63}$ and $R^{64}$ are independently H, alkyl, alkenyl, alkynyl, acyl, $PO_3^{2-}$, each of which may be optionally substituted;

$R^{65}$ is alkyl, alkenyl, alkynyl, acyl, fatty acid, or lipid each of which may be optionally substituted;

X is O, or NH;

Y is absent, or a linker; and pharmaceutically acceptable salts thereof.

In another aspect, provided herein is a method for the treatment or prevention of an inflammatory disease in a subject in need thereof, the method comprising administering to a subject having an inflammatory disease an NKT cell population contacted with an effective amount of a compound of formula (VI):

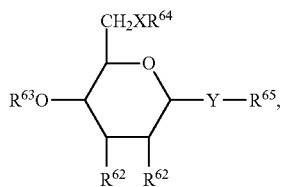

FORMULA (VI)

wherein:
$R^{61}$ is $OR^{63}$, $NH_2$, or NHC(O)-alkyl, or together with $R^{62}$ forms a second bond between the carbons they are attached to;
$R^{62}$ is $OR^{63}$ or together with $R^{61}$ forms a second bond between the carbons they are attached to;
$R^{63}$ and $R^{64}$ are independently H, alkyl, alkenyl, alkynyl, acyl, $PO_3^{2-}$, each of which may be optionally substituted;
$R^{65}$ is alkyl, alkenyl, alkynyl, acyl, fatty acid, or lipid each of which may be optionally substituted;
X is O, or NH;
Y is absent, or a linker; and
pharmaceutically acceptable salts thereof.

In another aspect, provided herein is the use of a compound of formula (VI) for treating or preventing an inflammatory disease in a subject in need thereof:

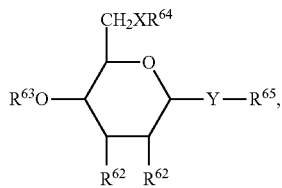

FORMULA (VI)

wherein:
$R^{61}$ is $OR^{63}$, $NH_2$, or NHC(O)-alkyl, or together with $R^{62}$ forms a second bond between the carbons they are attached to;
$R^{62}$ is $OR^{63}$ or together with $R^{61}$ forms a second bond between the carbons they are attached to;
$R^{63}$ and $R^{64}$ are independently H, alkyl, alkenyl, alkynyl, acyl, $PO_3^{2-}$, each of which may be optionally substituted;
$R^{65}$ is alkyl, alkenyl, alkynyl, acyl, fatty acid, or lipid each of which may be optionally substituted;
X is O, or NH;
Y is absent, or a linker; and
pharmaceutically acceptable salts thereof.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "media" as referred to herein is a medium for maintaining a tissue or cell population, or culturing a cell population (e.g. "culture media") containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

As used herein, the term "donor" refers to a subject to which a organ, tissue or cell to be transplanted is harvested from. As used herein, the term "recipient" refers to a subject which will receive a transplanted organ, tissue or cell. The term "graft" as used herein refers to the process whereby a free (unattached) cell, tissue, or organ integrates into a tissue following transplantation into a subject. The term "allograft" refers to a transplanted cell, tissue, or organ derived from a different animal of the same species. The term "xenograft" or "xenotransplant" as used herein refers to a transplanted cell, tissue, or organ derived from an animal of a different species. In some embodiments, a xenograft is a surgical graft of tissue from one species to an unlike species, genus or family. By way of an example, a graft from a baboon to a human is a xenograft.

The term "tissue" refers to a group or layer of similarly specialized cells which together perform certain special functions. The term "tissue-specific" refers to a source or defining characteristic of cells from a specific tissue.

The term "disease" or "disorder" is used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affection.

The term "pathology" as used herein, refers to symptoms, for example, structural and functional changes in a cell, tissue, or organs, which contribute to a disease or disorder.

A "marker," as used herein, describes the characteristics and/or phenotype of a cell. Markers can be used for selection of cells comprising characteristics of interest. Markers will vary with specific cells. Markers are characteristics, whether morphological, functional or biochemical (enzymatic), particular to a cell type, or molecules expressed by the cell type. Preferably, such markers are proteins, and more preferably, possess an epitope for antibodies or other binding molecules available in the art, such as a tetramer. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art.

Accordingly, as used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to. Cell-surface markers of particular relevance to the methods described herein include CD4, CD8, TCRβ, or CD25.

As defined herein, an "intracellular marker" refers to any molecule that can be detected within a cell, or prior to their release from a cell. Examples of intracellular markers that can be detected for the methods described herein, include, but are not limited to, cytokines, or transcription factors, such as Foxp3.

A cell can be designated "positive" or "negative" for any of the cell-surface or intracellular markers described herein, and both such designations are useful for the practice of the methods described herein. A cell is considered "positive" for a cell-surface or intracellular marker if it expresses the marker on its cell-surface or intracellularly in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell may express messenger RNA for a cell-surface or intracellular marker, in order to be considered positive for the methods described herein, the cell must express it as a protein. Similarly, a cell is considered "negative" for a cell-surface or intracellular marker if it does not express the marker on its cell-surface or intracellularly in amounts sufficient to be detected using methods known to those of skill in the art, such as contacting a cell with an antibody that binds specifically to that marker and subsequently performing flow cytometric analysis of such a contacted cell to determine whether the antibody is bound the cell. In some embodiments, agents specific for cell-surface lineage markers are used, where the agents can all comprise the same label or tag, such as fluorescent tag, and thus all cells positive for that label or tag can be excluded or removed for the methods using isolated NKT described herein, so that the remaining NKT cells are "negative" for the one or more lineage markers used.

Accordingly, as defined herein, an "agent specific for a cell-surface or intracellular marker" refers to an agent that can selectively react with or bind to that cell-surface or intracellular marker, but has little or no detectable reactivity to another cell-surface or intracellular marker or antigen. For example, an agent specific for CD4 will not be specific for CD8. Thus, agents specific for cell-surface or intracellular markers recognize unique structural features of the markers. In some embodiments, an agent specific for a cell-surface marker binds to the cell-surface marker, but does not cause initiation of downstream signaling events mediated by that cell-surface marker, for example, a non-activating antibody. Agents specific for cell-surface or intracellular molecules include, but are not limited to, antibodies or antigen-binding fragments thereof, natural or recombinant ligands, small molecules; nucleic acid sequence and nucleic acid analogues; intrabodies; aptamers; and other proteins or peptides.

In some embodiments described herein, the preferred agents specific for cell-surface or intracellular markers are antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)]. Such antibodies or antigen-binding fragments are available commercially from vendors such as R&D Systems, BD Biosciences, e-Biosciences and Miltenyi, or can be raised against these cell-surface markers by methods known to those skilled in the art.

In some embodiments of the aspects described herein, an agent specific for a cell-surface or intracellular molecule, such as an antibody or antigen-binding fragment, is labeled with a tag to facilitate the isolation of immune cell or NKT cell populations. The terms "label" or "tag", as used herein, refer to a composition capable of producing a detectable signal indicative of the presence of a target, such as, the presence of a specific cell-surface or intracellular marker in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods to isolate and enrich immune or NKT cells.

The terms "labeled antibody" or "tagged antibody", as used herein, includes antibodies that are labeled by detectable means and include, but are not limited to, antibodies that are fluorescently, enzymatically, radioactively, and chemiluminescently labeled. Antibodies can also be labeled with a detectable tag, such as c-Myc, HA, VSV-G, HSV, FLAG, V5, or HIS, which can be detected using an antibody specific to the tag, for example, an anti-c-Myc antibody. Various methods of labeling polypeptides and glycoproteins are known in the art and may be used. Non-limiting examples of fluorescent labels or tags for labeling the antibodies for use in the methods of invention include Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorophyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 (U.S.A. Health & Human Services) and WO 01/18058 (Novopharm Biotech Inc.) disclose bacteriophage display libraries and selection methods for producing antibody binding domain fragments. Methods for the production of antibodies are disclosed in PCT publication WO 97/40072 or U.S. Application. No. 2002/0182702, which are herein incorporated by reference. The processes of immunization to elicit antibody production in a mammal, the generation of hybridomas to produce monoclonal antibodies, and the purification of antibodies may be performed by described in "Current Protocols in Immunology" (CPI) (John Wiley and Sons, Inc.) and Antibodies: A Laboratory Manual (Ed Harlow and David Lane editors, Cold Spring Harbor Laboratory Press 1988) which are both incorporated by reference herein in their entirety.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein, the term "comprising" means that other elements can also be present in addition to the defined elements presented. The use of "comprising" indicates inclusion rather than limitation.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages may mean±1%.

BRIEF DESCRIPTION OF THE DRAWINGS

FIG. 1A is a schematic showing the protocol for OVA-induced AHR. Two-week-old (suckling) or 8 week-old (adult) mice were treated with influenza A virus (H3N1) or control AF (mock infection) and assessed 6 weeks later as adults for AHR. FIG. 1B shows BALB/c mice (n=8 per group) treated with H3N1 or AF at 2 weeks of age that were assessed 42 days after infection for OVA-induced AHR. Changes in lung resistance (RL) were measured in anesthetized, tracheotomized, intubated, and mechanically ventilated mice (left panel). ***$P<0.001$ compared with mock-infected group. Cells in BAL were collected and analyzed 24 hours after the final OVA challenge (right panel). *$P<0.05$ compared with mock-infected group. FIG. 1C shows representative lung sections stained with H&E (original magnification, ×10) from mock- or H3N1-infected mice treated with saline or challenged with OVA. FIG. 1D shows data from eight-week-old BALB/c mice (n=5 per group) that were infected with H3N1 or AF. Six weeks after infection, the mice were assessed for OVA-induced AHR by measuring lung resistance (left panel). Cells in BAL were collected and analyzed 24 hours after the final OVA challenge (right panel). Data are representative of 3 independent experiments.

FIG. 2A depicts a schematic showing a protocol for adoptive transfer of NKT cells to OVA-immunized $J\alpha 18^{-/-}$ recipients. The donor mice were infected with H3N1 or mock infected at 2 weeks of age. Six weeks after infection, NKT cells were purified and adoptively transferred into OVA-sensitized $J\alpha 18^{-/-}$ mice, which were then challenged with OVA and assessed for AHR. FIG. 2B demonstrates that adoptive transfer of H3N1-exposed NKT cells (vNKT) to $J\alpha 18^{-/-}$ mice failed to reconstitute OVA-induced AHR (measured as lung resistance in response to methacholine challenge) (left panel). Adoptive transfer of NKT cells from mock-infected mice (NKT) fully reconstituted AHR. H3N1 infection at 2 weeks of age of $J\alpha 18^{-/-}$ mice (v$J\alpha 18^{-/-}$) and reconstitution at 8 weeks of age with NKT cells from mock-infected mice did not protect against AHR (n=8-10 per group). BAL fluid was collected and analyzed (right panel). *$P<0.05$ and $P<0.01$, compared with Jα18$^{-/-}$ +NKT group. FIGS. 2C and 2D show lung cells that were isolated from the recipients after measurement of AHR, and the absolute numbers (2C) and percentages (2D) of lung CD4$^+$ or CD4$^-$CD8$^-$ (DN) NKT subsets were assessed by FACS. Upper panels show dot plots for NKT cells in lung leukocytes. After gating on the NKT cells, the cells were analyzed for CD4 and CD8 (lower panels). *P<0.001 compared with WT NKT group. Data are representative of 3 independent experiments.

FIGS. 3A-3G demonstrate that H3N1 infection in 2-week-old mice alters the phenotype of NKT cells. FIG. 3A shows lung cells that were isolated over a 6-week period and analyzed for NKT cells. Left: Absolute numbers of lung NKT cells. Right: Percentage of NKTs (top) in lung leukocytes. NKT cells were analyzed for CD4 and CD8 (bottom). FIG. 3B shows Left: BALB/c mice (n=3/group) that were infected with H3N1 or AF at 2 or 8 weeks of age, and data from lung NKT cells that were assessed over 2 weeks. Right: Percentage of NKT cells in lungs of 2-week-old and 8-week-old mice. FIG. 3C shows two-week-old BALB/c mice that were mock infected or infected with H3N1, and pulmonary CD4$^+$ NKT and DN NKT cell numbers were assessed on days 1 and 14 after infection. FIGS. 3D and 3E show data from NKT cells from FIG. 3C that were assessed for CD4, IFN-γ, and IL-4 expression (3D) and absolute numbers quantified (3E). FIG. 3F shows BALB/c mice (n=4-5/group) that were infected with H3N1 or mock infected at 2 or 8 weeks of age, and lung samples were taken 42 days later to assess NKT cell subsets. One of 2 independent experiments is shown. FIG. 3G shows data from two-week-old BALB/c mice were infected with H3N1 or mock infected. After 42 days, lung cells were harvested and stimulated ex vivo with vehicle or α-GalCer for 96 hours. IFN-γ and IL-4 in supernatants from triplicate wells were determined by ELISA and the IFN-γ/IL-4 ratio calculated. *P<0.05, ***P<0.001 compared with mock infection.

FIG. 4A depicts a protocol for adoptive transfer of NKT cells. FIGS. 4B and 4C show lung resistance data that was measured in recipient mice (4B; n=15/group) and BAL cells collected (4C). FIG. 4D shows assessment of relative numbers of CD4$^+$ versus DN NKT cells in recipients' lungs. FIG. 4E shows H3N1-exposed CD4$^-$CD8$^-$NKT (vDN NKT) or CD4$^+$NKT (vCD4 NKT) cells were purified and transferred as in FIG. 4A. Lung resistance was measured in recipient mice (n=5/group). FIG. 4F shows data from eight-week-old WT BALB/c mice that received 5×10$^4$ DO11.10 Rag$^{-/-}$ T cells and were sensitized with OVA/alum. Seven days later, NKT cells from WT BALB/c, Vα14tg, or H3N1-infected mice were adoptively transferred into OVA-sensitized mice. After OVA challenge, the numbers of natural T$_{regs}$ (CD4$^+$C25$^+$Foxp3$^+$) and adaptive OVA antigen-specific T$_{regs}$ (CD4$^+$CD25$^+$Foxp3$^+$KJ1-26$^+$) were determined. Absolute cell numbers were calculated (n=5/group). FIG. 4G shows data from eight-week-old WT BALB/c recipients that were depleted of T$_{regs}$ through injections of anti-CD25 mAb (clone PC61; 0.5 mg) and assessed as in FIG. 4A (n=5/group). FIGS. 4H and 4I show data from NKT cells from WT or Vα14 Tg that were transferred to OVA-sensitized BALB/c mice (n=4-6/group), which were assessed as in FIG. 4A (4H), and BAL cells that were analyzed (4I). FIG. 4J shows representative lung sections from recipients described in 4H that were H&E stained (original magnification, ×10). Data represent 2-3 independent experiments. *P<0.05, P<0.01, *P<0.001 versus WT NKT-OVA (4B-4D), OVA (4E), WT NKT (4F, 4H, and 4I), and OVA-vNKT (4G).

FIG. 5A is a schematic showing the protocol for WT, Tlr7$^{-/-}$, or Tbet$^{-/-}$ mice infected at 2 weeks of age with H3N1 virus or mock infected and examined for OVA-induced AHR at 8 weeks of age (n=4-6 per group). FIG. 5B shows lung resistance was measured. *P<0.05, P<0.01, *P<0.001 compared with the mock-OVA group. FIG. 5C shows BAL cells from 5B were collected. FIG. 5D shows WT, Tlr7$^{-/-}$, or Tbet$^{-/-}$ mice were infected with H3N1 or mock at 2 weeks of age, and lung samples were taken 42 days later to assess for NKT cell subsets. *P<0.001 compared with the mock group. FIG. 5E is a schematic showing the adoptive transfer of NKT from virus-infected WT, Tlr7$^{-/-}$, or Tbet$^{-/-}$ mice to OVA-sensitized BALB/c recipients (n=4-6 per group). The donor mice were infected with H3N1 or mock-infected at 2 weeks of age. NKT cells were purified from these mice 42 days after infection and transferred to OVA-sensitized BALB/c mice, which were then challenged with OVA to induce AHR. FIG. 5F shows Left: After OVA challenge, AHR was measured as described in 5D. Right: Cells in BAL were assessed. *P<0.001 compared with the WT-OVA group. Data are representative of 2 independent experiments.

In FIGS. 6A-6B, two-week-old BALB/c mice (n=6-8/group) (6A) or Tbet$^{-/-}$ mice (6B) (n=4-6 per group) received 5 μg α-GalCer (cGal), 2 μg α-GalCer, or vehicle. After OVA sensitization and challenge, AHR was measured on day 44. In FIG. 6C, donor mice were treated with α-C-GalCer (5 μg) or vehicle i.p. NKT cells served as donors, as in FIG. 4A (n=4 per group). Lung resistance (left) and cell counts in BAL (right) were assessed. FIG. 6D shows a structure of PI57. In FIG. 6E, mice received PI57 (50 μg), α-GalCer (2 μg), or vehicle i.p., and lungs were examined 1 or 14 days later for CD4 and CD8 expression. In FIG. 6F, absolute numbers of CD4$^+$ NKT and DN NKT subsets from 6E were assessed. In FIG. 6G, BALB/c mice (n=5-8/group) received PI57 or vehicle i.p. Lung resistance (left) and BAL cells (right) were assessed.

FIGS. 7A-7G demonstrate that PI57 directly activates NKT cells. In FIG. 7A, NKT cell lines were cocultured with BM-derived DCs (BMDCs) and α-GalCer (100 ng/ml), PI57 (10 μg/ml), or vehicle for 48 hours, with or without preincubation with anti-CD1d (10 μg/ml). IFN-γ was measured by ELISA. In FIG. 7B, murine NKT cell lines were cocultured as in 7A with BMDCs from WT, Cd1d$^{-/-}$, Myd88$^{-/-}$, or Trif$^{-/-}$ mice. Cells were treated with α-GalCer (100 ng/ml), PI57 (2.5, 5, or 10 μg/ml), PBS30 (1, 2.5, or 5 μg/ml), or vehicle for 48 hours. IFN-γ and IL-4 were measured by ELISA. FIG. 7C shows IL-2 production from hybridomas derived from invariant Vα14 NKT cells (RT2, RT23, and RT24) and an irrelevant Vβ8+ T cell (RT8; control). In FIG. 7D, mouse NKT cell lines were stained with PE-labeled CD1d tetramers of PI57 or α-GalCer at 4° C. for 45 minutes or 37° C. for 25 minutes, and with anti-TCRβ-APC antibody. Top: Lymphocytes were gated in the FSC/SSC window. Bottom: Percentage of CD1d tetramer+ cells. FIG. 7E shows IFN-γ and IL-4 production from human NKT cell lines by treatment with α-GalCer (100 ng/ml), PI57 (10 μg/ml), or vehicle for 48 hours in vitro. FIG. 7F shows IFN-γ production from CD1d-transfected NKT cell clone BM2a.3 in presence of PI57 and blocking mAb against human CD1d or CD1b. In FIG. 7G, CD1d Fc-coated Maxisorp plates were loaded with lipid and cultured with $5\times10^4$ NKT cells. IFN-γ was analyzed by ELISA after 24 hours. Data represent 3 or 5 independent experiments.

FIG. 8A shows purity of sorted NKT from indicated donors, including NKT cells from mock-infected mice (WT NKT), from H3N1-infected mice (vNKT), from Vα14 Tg (Vα14 NKT), from PI57-treated mice (PI57-NKT) or from α-GalCer-treated BALB/c (α-Gal-NKT), that was assessed by FACS. In FIG. 8B, the sorted NKT cells from WT (WT NKT) and Vα14 Tg (Vα14 NKT) mice were assessed by FACS for CD4+, DN NKT cell subsets or for contamination by $T_{Reg}$ cells (CD4$^+$CD25$^+$Foxp3$^+$). FIG. 8C shows sorted NKT cells from H3N1 infected suckling mice 42 days after infection that were assessed by FACS for CD4+ and DN NKT cell subsets FIGS. 9A-9E demonstrate that TLR7 and T-bet affect cytokine production by H3N1 exposed NKT cells in lung cells. In FIG. 9A, percentages of IFN-γ or IL-4 secreting CD4$^+$ NKT and DN NKT subsets in WT or T-bet$^{-/-}$ mice 1 or 14 days post-infection were assessed by FACS. In FIGS. 9B-9D, lung cells were harvested on day 42 after infection and stimulated ex vivo with 10 or 100 ng/ml α-GalCer or vehicle for 96 hrs. Concentration of IFN-γ (9B) and IL-4 (9C) in the supernatant was measured by ELISA. *$p<0.05$,*$p<0.001$, compared to mock or WT group. FIG. 9D shows ratio of IFN-γ/IL-4 secretion from NKT cells with 100 ng/ml α-GalCer that was calculated. *$p<0.001$, compared to the mock group.

In FIG. 10, NKT cells from α-GalCer or vehicle-treated mice were adoptively transferred to OVA-sensitized BALB/c recipients. AHR was measured after OVA challenge. In FIG. 10B, T-bet$^{-/-}$ mice (n=4-6 per group) received 50 μg PI57 or vehicle at 2 wks of age. After sensitization and challenge with OVA, AHR was measured on day 44. These data demonstrate that protective effects of PI57 depends on T-bet expression.

FIG. 11A shows ES-MS negative mode spectrum of AGlc-Chol lipid. FIG. 11B shows $^1$H NMR spectrum of AGlc-Chol lipid recorded in CDCl3-CD3OD (2:1, v/v) at 300K (500.13 MHz). FIG. 11C shows a two-dimensional $^1$H-$^1$H COSY NMR spectrum of AGlc-Chol lipid recorded in CDCl3-CD3OD (2:1, v/v) at 300K (500.13 MHz). FIG. 11D shows a $^1$H NMR spectrum of synthetic PI57 lipid recorded in CDCl3-CD3OD (2:1, v/v) at 300K (300 MHz).

DETAILED DESCRIPTION OF THE INVENTION

Figure 1A:
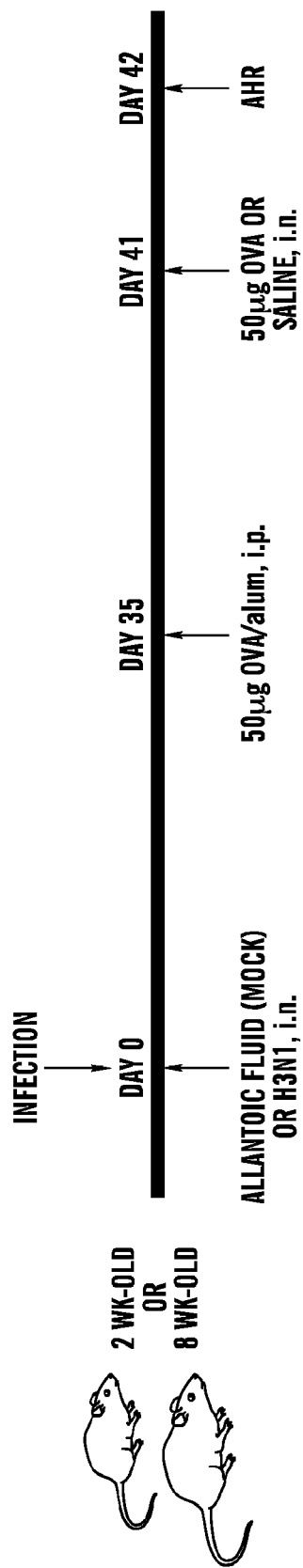
FIGS. 1A-1D demonstrate that infection of suckling mice with H3N1 protects the mice against AHR when adults.

Described herein are novel methods and compositions for the prevention and treatment of inflammatory disorders, such as allergic asthma and autoimmune diseases, based, in part, on the inventors novel discovery that immunological exposure to bacteria or viruses at an early age can modulate the development and function of a subset of innate immune cells known as NKT cells.

The inventors demonstrate for the first time that a population of NKT cells, enriched for a DN, T-bet$^+$ and IFN-γ producing subset, has a potent regulatory role that suppresses the development of AHR, and can influence the development and expansion of other regulatory immune cells, such as Foxp3$^+$ $T_{Reg}$ cells. In contrast to a previous study that described that treatment of mice with α-GalCer, an NKT stimulating glycolipid, inhibits the development of asthma by anergizing NKT cells (52), the studies described herein demonstrate that NKT cells, specifically immature NKT cells as found in young mice or children, responding to viral and bacterial infections undergo phenotypic and functional changes to form a regulatory NKT cell population that can actively suppress subsequent inflammation, such as allergen-induced AHR, without requiring subsequent exposure to exogenous glycolipids.

More specifically, the inventors have discovered that NKT cell-activating glycolipids derived from H. pylori, when administered at a young age, modulate NKT cell development, resulting in the maturation of a specific subset of regulatory NKT cells, that protect against the subsequent development of allergen-induced AHR. This population of NKT cells is associated with the expansion of Foxp3$^+$ $T_{Reg}$ cells. In addition, the inventors further demonstrate herein that pre-treatment of adult mice with NKT cell-activating glycolipids derived from H. pylori can inhibit or suppress airway hyperreactvity and lung inflammation using an ozone-exposure model. The inventors have also shown herein that infection of two-week-old mice with an influenza A virus H3N1 protects against the subsequent development of allergen-induced AHR, and that the protective effect of infection in young mice was associated with the maturation and expansion of a specific subset of NKT cells. The inventors have also shown that suppression of the development of allergen-induced AHR can be transferred into normal allergen-sensitized adult mice by adoptive transfer of these NKT cells. Adoptive transfer of the protective NKT cell population was associated with the expansion of allergen-specific Foxp3$^+$ $T_{Reg}$ cells in the recipient animals, implicating Foxp3$^+$ $T_{Reg}$ cells in mediating the suppressive effect. Accordingly, the aspects described herein provide methods for immunoregulation of inflammatory diseases using NKT cells.

Glycolipid Compositions and Methods

Provided herein are sterol glycosides and derivatives thereof for use in compositions and methods of inhibiting and preventing the development, i.e., "immunoregulation," of inflammatory conditions, such as asthma and autoimmune diseases. The inventors have discovered that glycolipids, such as cholesteryl 6-O-tetradecanoyl-α-D-glucopyranoside) (also referred to herein as cholesteryl-6-O-acyl α-glucoside or AGlc-Chol), derived from the bacterium Helicobacter pylori (H. pylori) can activate the population of immune cells known as NKT cells, and further that direct administration of such glycolipids can modulate in vivo immune responses. In addition, pre-treatment with glycolipids, such as cholesteryl 6-O-tetradecanoyl-α-D-glucopyranoside derived from the bacterium *Helicobacter pylori* (*H. pylori*), prior to ozone-exposure, is shown herein to inhibit or suppress airway hyperreactivity and lung inflammation in adult mice. As described herein, the administration of an effective amount of such glycolipids during the development of the immune system, i.e., at a young age, can be used to modulate NKT cell development such that a specific subset of double-negative (CD4⁻CD8⁻) NKT cells with suppressive functions, such as the production of IFN-γ, is expanded. Such NKT cells can also be adoptively transferred into a recipient subject in need thereof.

Accordingly, provided herein for use with the various aspects, compositions, uses, and methods described herein are compounds of formula (I):

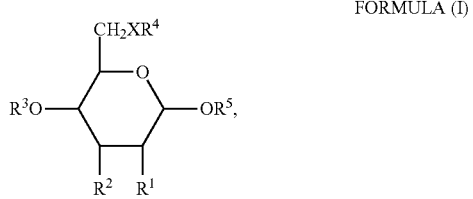

FORMULA (I)

wherein:
$R^1$ is $OR^3$, $NH_2$, or NHC(O)-alkyl, or together with $R^2$ forms a second bond between the carbons they are attached to;
$R^2$ is $OR^3$ or together with $R^1$ forms a second bond between the carbons they are attached to;
$R^3$ and $R^4$ are independently H, alkyl, alkenyl, alkynyl, acyl, $PO_3^{2-}$, each of which may be optionally substituted;
$R^5$ is

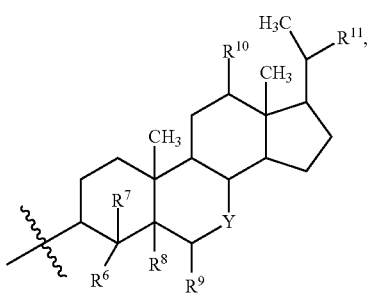

alkyl, alkenyl, alkynyl, or acyl, each of which may be optionally substituted;
$R^6$ and $R^7$ are both H or both alkyl;
$R^8$ is H or together with $R^9$ forms a second bond between the carbons to which they are attached;
$R^9$ is H, $OR^3$, or together with $R^8$ forms a second bond between the carbons to which they are attached;
$R^{10}$ is H, OH, alkyl, or O-alkyl, each of which may be optionally substituted;
$R^{11}$ is alkyl, alkenyl, or alkynyl, each of which may be optionally substituted;
X is O, or NH;
Y is $CH_2$, C(O), or $CHOR^3$; and
pharmaceutically acceptable salts thereof.

In some embodiments of the aspects described herein, a compound of formula (I) is selected from the group consisting of: cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside; 7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate-α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O-tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6- bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside.

In some embodiments of the aspects described herein, the compound of formula (I) is cholesteryl 6-O-tetradecanoyl-α-D-glucopyranoside.

In some embodiments of the aspects described herein, the compound of formula (I) is cholesteryl 6-O-acyl α-glucocoside.

In some embodiments of the aspects described herein, $R^1$ is OH, $NH_2$, $NH(CO)CH_3$, or $OPO_3^{2-}$.

In some embodiments of the aspects described herein, $R^2$ is OH, O-alkyl or O-acyl. Preferred alkyls for $R^2$ include, but are not limited to, $C_1$-$C_6$ alkyls such as methyl, ethyl, propyl, butyl, iso-propyl, t-butyl, pentyl and hexanyl, each of which may be optionally substituted. Preferred acyls for $R^2$ include, but are not limited to, ethanoyl, propanoyl, butanoyl, iso-propanoyl, t-buanotyl, pentanoyl and hexanoyl.

In some embodiments of the aspects described herein, $R^1$ and $R^2$ together form a second bond between the carbons they are attached to.

In some embodiments of the aspects described herein, $R^3$ is H, $CH_3$ or $C(O)CH_3$.

In some embodiments of the aspects described herein, $R^4$ is H, alkyl, alkenyl, alkynyl, acyl, or $PO_3^2$. Exemplary alkyls for $R^4$ include, but are not limited to methyl, ethyl, propyl, butyl, t-butyl, hexanyl, and tetradecanyl (myristyl), pentadecanyl, hexadecanyl (cetyl), heptadecanyl, octadecanyl (stearyl), 16-methylheptadecanyl (isotearyl). Preferred alkenyls for $R^4$ include, but are not limited to, $C_{12}$-$C_{20}$ alkenyls comprising 1, 2, or 3 double bonds, e.g., 9Z,12Z-octadecadien-yl (linoleyl); 9Z,12Z,15Z-octadecatrienyl (linolenyl); gamma-linolenyl; 9-hexadecenyl (palmitoleyl); 9E-octadecenyl (elaidyl); cis-9-octadecenyl (oleyl); 9E,12E-octadecadienyl (elaidolinoleyl); 9E,12E,15E-octadecatrienyl (elaidolinolenyl); 12-hydroxy-9-octadecenyl (ricinoleyl); 1-eicosanyl (arachidyl); myrsitoleyl; sapienyl; archidonyl; eicosapentaenyl; erucyl; docosahexanyl; 15Z-tetracosenyl; 2-amino-4-octadecene-3-olyl; and 2-amino-9-methyl-nonadec-4,8-diene-3-olyl. Preferred alkynyls for $R^4$ include, but are not limited to, $C_{12}$-$C_{20}$ alkynyls comprising 1, 2, or 3 double bonds. In some embodiments, $R^4$ is a $C_{12}$-$C_{20}$ alkyl comprising 1, 2, or 3 double and/or triple bonds.

Exemplary acyls for $R^4$ include, but are not limited to, ethanoyl; propanoyl; butanoyl; t-butanoyl; hexanoyl; heptanoyl; octanoyl; nonanoyl; tetradecanoyl; pentadecanoyl; hexadecanoyl; heptadecanoyl; octadecanoyl; 16-methylheptadecanoyl; 9Z,12Z-octadecadienoyl; 9Z,12Z,15Z-octadecatrienoyl; gamma-linolenoyl; 9-butadecenoyl; 9-hexadecenoyl; 6-hexadecenoyl; 9E-octadecenoyl; cis-9-octadecenoyl; 9E,12E-octadecadienoyl; 9E,12E,15E-octadecatrienoyl; 2-hydroxy-9-octadecenoyl; 1-eicosanoyl; 15Z-tetracosenoyl myrsitolenoyl; sapienoyl; archidonoyl; eicosapentaenoyl; erucoyl; and docosahexanoyl.

In some embodiments $R^4$ is

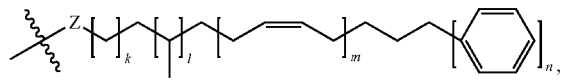

wherein Z is $CH_2$ or $C(O)$; k is 2, 4, 6, 8, 10, 12, or 16; l is 0, 1, 2, 3, or 4; n is 0 or 1; and m is 0 or 1.

The $OR^5$ substituent on the sugar of a compound of formula (I) can be in the α or β relative to the sugar. Accordingly, in some embodiments, the $OR^5$ substituent is in the α configuration relative to the sugar. In some other embodiments, the $OR^5$ substituent is in the β configuration relative to the sugar.

In some embodiments, $R^5$ is

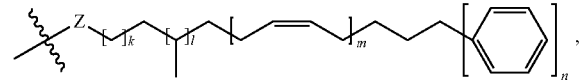

wherein Z is $CH_2$ or $C(O)$; k is 2, 4, 6, 8, 10, 12, or 16; l is 0, 1, 2, 3, or 4; n is 0 or 1; and m is 0 or 1.

In some embodiments of the aspects described herein both $R^6$ and $R^7$ are H. In some other embodiments of compounds of formula (I), both $R^6$ and $R^7$ are alkyl, e.g., methyl, or ethyl.

In some embodiments of the aspects described herein, both $R^8$ and $R^9$ are H. In some other embodiments of the aspects described herein, $R^8$ and $R^9$ together form a second bond between the carbons to which they are attached.

In some embodiments of the aspects described herein, Y is $CH_2$, $C(O)$, or $CHOH$.

In some embodiments of the aspects described herein, $R^{10}$ is preferably H, or OH.

In some embodiments of the aspects described herein, $R^{11}$ is alkyl or alkenyl. Preferred alkyls and alkenyls for $R^{11}$ include, but are not limited to, 4-methylpentyl; 3,4-dimetnylpentyl, 3-ethyl-4-methylpentyl; 3-ethyl-4-methyl-1-pentenyl; 3,4-dimethyl-1-pentenyl; and 3-propanoic acid.

In some embodiments of the aspects described herein, $R^{11}$ is

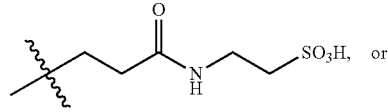

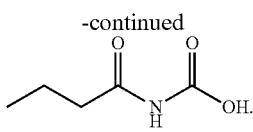

The sugar component of the compounds of formula (I) can be selected from the group consisting of allose, glucose, mannose, gulose, idoes, galactose, talose, and derivatives and analogs thereof, each of which may be optionally substituted.

In some embodiments, $R^5$ is an alkyl, alkenyl, alkynyl, or acyl, each of which may be optionally substituted. Exemplary alkyl, alkenyl and alkenyl for $R^5$ include, but are not limited to, methyl; tetradecanyl (myristyl); pentadecanyl; hexadecanyl(cetyl); heptadecanyl, octadecanyl (stearyl); 16-methylheptadecanyl (isotearyl); 9Z,12Z-octadecadien-yl (linoleyl); 9Z,12Z,15Z-octadecatrienyl (linolenyl); gamma-linolenyl; 9-hexadecenyl (palmitoleyl); 9E-octadecenyl (elaidyl); cis-9-octadecenyl (oleyl); 9E,12E-octadecadienyl (elaidolinoleyl); 9E,12E,15E-octadecatrienyl (elaidolinolenyl); 12-hydroxy-9-octadecenyl (ricinoleyl); and 1-eicosanyl (arachidyl).

Exemplary acyls for $R^5$ include, but are not limited to, ethanoyl; propanoyl; butanoyl; t-butanoyl; hexanoyl; heptanoyl; octanoyl; nonanoyl; tetradecanoyl; pentadecanoyl; hexadecanoyl; heptadecanoyl; octadecanoyl; 16-methylheptadecanoyl; 9Z,12Z-octadecadienoyl; 9Z,12Z,15Z-octadecatrienoyl; gamma-linolenoyl; 9-butadecenoyl; 9-hexadecenoyl; 6-hexadecenoyl; 9E-octadecenoyl; cis-9-octadecenoyl; 9E,12E-octadecadienoyl; 9E,12E,15E-octadecatrienoyl; 2-hydroxy-9-octadecenoyl; 1-eicosanoyl; 15Z-tetracosenoyl myrsitolenoyl; sapienoyl; archidonoyl; eicosapentaenoyl; erucoyl; and docosahexanoyl.

In some embodiments of the aspects described herein, $R^5$ is selected from the group consisting of bile acids (such as cholic acid, deoxycholic acid, chenodeoxycholic acid, glycocholic acid, taurocholic acid, deoxychlolic acid, lithocholic acid), cholesterol, 7-beta-hydroxycholesterol, 7-ketocholesterol, 6,7-dihydroxy-cholesterol, 5,6,-epoxy-cholesterol, stigmasterol, lanosterol, beta-sitosterol, ergosterol, campesterol, brassicasterol, and derivatives and analogs thereof, each of which may be optionally substituted.

In some embodiments of the aspects described herein, the compound of formula (I) is of formula (II):

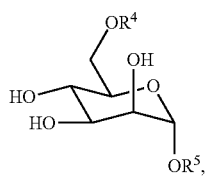

FORMULA (II)

wherein $R^4$ and $R^5$ are as defined for formula (I).

In some embodiments of the compounds of formula (II), $R^4$ is H or acyl. In some compounds of formula (II), $R^4$ is

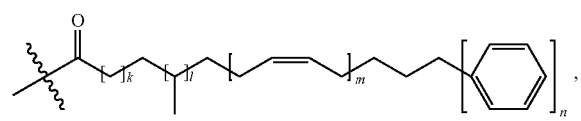

wherein k is 2, 4, 6, 8, 10, 12, or 16; l is 0, 1, 2, 3, or 4; n is 0 or 1; and m is 0 or 1.

In some embodiments of the compounds of formula (II), $R^5$ is cholesterol.

In some embodiments of the aspects described herein, the compound of formula (I) is of formula (III):

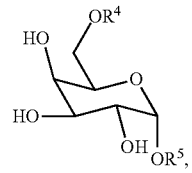

FORMULA (III)

wherein $R^4$ and $R^5$ are as defined for formula (I).

In some embodiments of the compounds of formula (III), $R^4$ is H, or acyl. In some compounds of formula (III), $R^4$ is

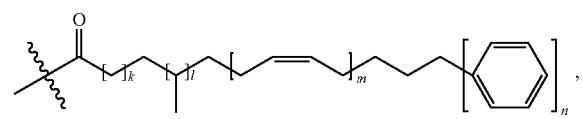

wherein k is 2, 4, 6, 8, 10, 12, or 16; l is 0, 1, 2, 3, or 4; n is 0 or 1; and m is 0 or 1.

In some embodiments of the compounds of formula (III), $R^5$ is cholesterol.

In some embodiments of the aspects described herein, the compound of formula (I) is of formula (IV):

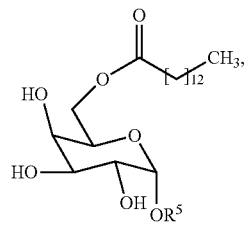

FORMULA (IV)

wherein $R^5$ is as defined above for formula (I).

In some embodiments of the compounds of formula (IV), $R^5$ is sterol or alkyl.

In some embodiments of the compounds of formula (IV), $R^5$ is

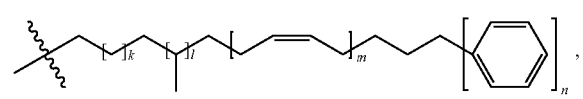

wherein k is 2, 4, 6, 8, 10, 12, or 16; l is 0, 1, 2, 3, or 4; n is 0 or 1; and m is 0 or 1.

In some embodiments of the aspects described herein, the compound of formula (I) is of formula (V):

FORMULA (V)

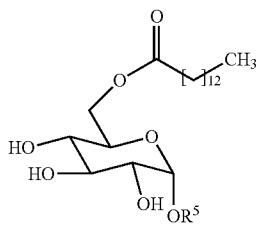

wherein R$^5$ is as defined above for formula (I).

In some embodiments of the compounds of formula (V), R$^5$ is sterol or alkyl.

In some embodiments of the compounds of formula (V), R$^5$ is

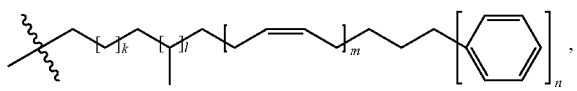

wherein k is 2, 4, 6, 8, 10, 12, or 16; l is 0, 1, 2, 3, or 4; n is 0 or 1; and m is 0 or 1.

In some embodiments of the aspects described herein, in the compound of formula (I), R$^5$ substituent is not ceramide.

In some embodiments of the aspects described herein, the compound of formula (I) is not α-galactosyl-ceramide (ceramide-α-D-galactoside).

Also provided herein are C-glycoside analogs and derivatives thereof of α-galactosyl ceramides, for use in inhibiting and preventing the development, i.e., the "immunoregulation," of inflammatory conditions, such as asthma and autoimmune diseases. The inventors have further discovered that direct administration of α-C-GalCer (α-C-galactosyl ceramide), a C-glycoside analog of α-galactosyl ceramide, and derivatives thereof can modulate in vivo immune responses, and inhibit or suppress airway hyperreactivity and lung inflammation. Further, the inventors have found that the administration of an effective amount of such glycolipids during the development of the immune system, i.e., at a young age, can be used to prevent airway inflammation and hyperreactivity upon subsequent allergen exposure, and that these effects are dependent upon IFN-γ production.

Accordingly, provided herein for use with the various aspects, compositions, uses, and methods described herein are compounds of compound of formula (VI):

FORMULA (VI)

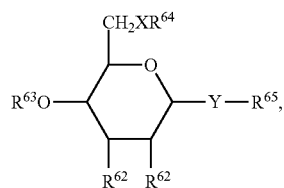

wherein:
R$^{61}$ is OR$^{63}$, NH$_2$, or NHC(O)-alkyl, or together with R$^{62}$ forms a second bond between the carbons they are attached to;
R$^{62}$ is OR$^{63}$ or together with R$^{61}$ forms a second bond between the carbons they are attached to;
R$^{63}$ and R$^{64}$ are independently H, alkyl, alkenyl, alkynyl, acyl, PO$_3^{2-}$, each of which may be optionally substituted;
R$^{65}$ is alkyl, alkenyl, alkynyl, acyl, fatty acid, or lipid each of which may be optionally substituted;
X is O, or NH;
Y is absent, or a linker; and
pharmaceutically acceptable salts thereof.

In some embodiments of the aspects described herein, R$^{61}$ is OH, NH$_2$, NH(CO)CH$_3$, or OPO$_3^{2-}$.

In some embodiments of the aspects described herein, R$^{62}$ is OH, O-alkyl or O-acyl. Preferred alkyls for R$^{62}$ include, but are not limited to, C$_1$-C$_6$ alkyls such as methyl, ethyl, propyl, butyl, iso-propyl, t-butyl, pentyl and hexanyl, each of which may be optionally substituted. Preferred acyls for R$^{62}$ include, but are not limited to, ethanoyl, propanoyl, butanoyl, iso-propanoyl, t-buanotyl, pentanoyl and hexanoyl.

In some embodiments of the aspects described herein, R$^{61}$ and R$^{62}$ together form a second bond between the carbons they are attached to.

In some embodiments of the aspects described herein, R$^{63}$ is H, CH$_3$ or C(O)CH$_3$.

In some embodiments of the aspects described herein, R$^{64}$ is H, alkyl, alkenyl, alkynyl, acyl, or PO$_3^2$. Exemplary alkyls for R$^{64}$ include, but are not limited to methyl, ethyl, propyl, butyl, t-butyl, hexanyl, and tetradecanyl (myristyl), pentadecanyl, hexadecanyl (cetyl), heptadecanyl, octadecanyl (stearyl), 16-methylheptadecanyl (isotearyl). Preferred alkenyls for R$^4$ include, but are not limited to, C$_{12}$-C$_{20}$ alkenyls comprising 1, 2, or 3 double bonds, e.g., 9Z,12Z-octadecadien-yl (linoleyl); 9Z,12Z,15Z-octadecatrienyl (linolenyl); gamma-linolenyl; 9-hexadecenyl (palmitoleyl); 9E-octadecenyl (elaidyl); cis-9-octadecenyl (oleyl); 9E,12E-octadecadienyl (elaidolinolenyl); 9E,12E,15E-octadecatrienyl (elaidolinolenyl); 12-hydroxy-9-octadecenyl (ricinoleyl); 1-eicosanyl (arachidyl); myrsitoleyl; sapienyl; archidonyl; eicosapentaenyl; erucyl; docosahexanyl; 15Z-tetracosenyl; 2-amino-4-octadecene-3-olyl; and 2-amino-9-methyl-nonadec-4,8-diene-3-olyl. Preferred alkynyls for R$^{64}$ include, but are not limited to, C$_{12}$-C$_{20}$ alkynyls comprising 1, 2, or 3 double bonds. In some embodiments, R$^{64}$ is a C$_{12}$-C$_{20}$ alkyl comprising 1, 2, or 3 double and/or triple bonds.

Exemplary acyls for R$^{64}$ include, but are not limited to, ethanoyl; propanoyl; butanoyl; t-butanoyl; hexanoyl; heptanoyl; octanoyl; nonanoyl; tetradecanoyl; pentadecanoyl; hexadecanoyl; heptadecanoyl; octadecanoyl; 16-methylheptadecanoyl; 9Z,12Z-octadecadienoyl; 9Z,12Z,15Z-octadecatrienoyl; gamma-linolenoyl; 9-butadecenoyl; 9-hexadecenoyl; 6-hexadecenoyl; 9E-octadecenoyl; cis-9-octadecenoyl; 9E,12E-octadecadienoyl; 9E,12E,15E-octadecatrienoyl; 2-hydroxy-9-octadecenoyl; 1-eicosanoyl; 15Z-tetracosenoyl myrsitolenoyl; sapienoyl; archidonoyl; eicosapentaenoyl; erucoyl; and docosahexanoyl.

In some embodiments R$^{64}$ is

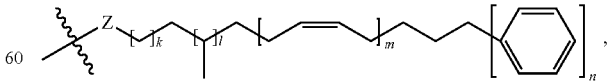

wherein Z is CH$_2$ or C(O); k is 2, 4, 6, 8, 10, 12, or 16; l is 0, 1, 2, 3, or 4; n is 0 or 1; and m is 0 or 1.

The —Y—R$^{65}$ substituent on the sugar of a compound of formula (VI) can be in the α or β relative to the sugar. Accordingly, in some embodiments, the —Y—R$^{65}$ substituent is in the α configuration relative to the sugar. In some other embodiments, the —Y—$R^{65}$ substituent is in the β configuration relative to the sugar.

In some embodiments, $R^{65}$ is a lipid. In some embodiments of this, $R^{65}$ is selected from the group consisting of fatty acyls, glycerolipids, glycerophospholipids, sphingolipids, saccharolipids and polyketides, sterol lipids and prenol lipids.

In some embodiments, $R^{65}$ is selected from the group consisting of ceramides, diacylphosphatidylcholine, diacylphosphatidylethanolamine, ceramide, sphingomyelin, cephalin, cerebrosides, cardiolipim, diacylphosphatidylserine and diacylphosphatidic acid.

In one embodiment, $R^{65}$ is ceramide.

As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^{101})_2$, C(O), cleavable linking group, substituted or unsubstituted aryl, substituted or unsubstituted heteroaryl, substituted or unsubstituted heterocyclic; where $R^{101}$ is hydrogen, acyl, aliphatic or substituted aliphatic.

In some embodiments, the linker is an optionally substituted $C_1$-$C_{10}$ alkylene.

In one embodiment, the linker is —$(CH_2)_m$—, wherein m an integer from 1, 2, 3, 4, 5, 6, 7, 8, 9, or 10. Preferably m is 1, 2 or 3.

The sugar component of the compounds of formula (VI) can be selected from the group consisting of allose, glucose, mannose, gulose, idoes, galactose, talose, and derivatives and analogs thereof, each of which may be optionally substituted.

In some embodiments, the compound of formula (VI) is of formula (VIa):

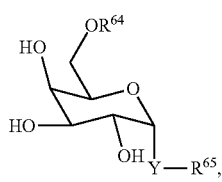

FORMULA (VIa)

wherein $R^{64}$, $R^{65}$ and Y are as defined for formula (VI).

In some embodiments of compounds of formula (VIa), $R^{64}$ is H.

In some embodiments, the compound of formula (VI) is of formula (IVIb):

FORMULA (VIb)

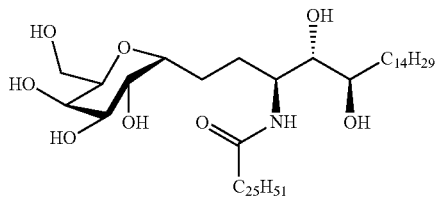

wherein $R^{64}$, $R^{65}$ and Y are as defined for formula (VI).

In some embodiments of compounds of formula (VIa), $R^{64}$ is H.

In one embodiment, a compound of formula (VI) is α-C-Galactosylceramide (α-C-GalCer).

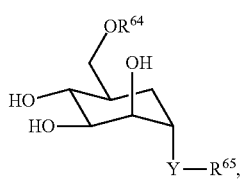

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. The term "lipid" as used herein also includes vegetable oils, seed oils, triglycerides, waxes of triglycerides, and phospholipids. Accordingly, the term "lipid" includes fatty acyls, glycerolipids, glycerophospholipids, sphingolipids, saccharolipids and polyketides, sterol lipids and prenol lipids. Exemplary lipids include, but are not limited to, diacylphosphatidylcholine, diacylphosphatidylethanolamine, ceramides, sphingomyelin, cephalin, cerebrosides, cardiolipim, diacylphosphatidylserine and diacylphosphatidic acid. Generally, the acyl groups in these lipids are acyl groups derived from fatty acids having $C_{10}$-$C_{24}$ carbon chains. For example, the acyl groups can be lauroyl, myristoyl, palmitoyl, stearoyl or oleoyl.

The compounds of formula (I) can be synthesized starting from the respective sugar and $R^5$ (e.g., sterol, alkyl, alkenyl, alkynyl, or acyl) components utilizing methods well known to the skilled artisan for glycoside synthesis. Such methods can include, for example, the Fischer glycosylation. Synthesis of sterol components of formula (I) is shown for example in U.S. Pat. Nos. 5,496,806; 5,338,837; and 4,402,948, the contents of each of which are herein incorporated by reference.

The compounds of formula (I) can be easily synthesized starting from the respective sugar and sterol components utilizing methods well known to the skilled artisan for glycoside synthesis. Such methods can include, for example, the Fischer glycosylation. Synthesis of sterol components of formula (I) is shown for example in U.S. Pat. Nos. 5,496,806; 5,338,837; and 4,402,948, the contents of each of which are herein incorporated by reference.

The synthesis of compounds of formula (I) can be carried out using methods well known to the skilled artisan. In one non-limiting example, compounds of formula (I) can be obtained by the stereospecific conjugation of an appropriately protected of glycopyranosyl unit with an appropriately protected $R^5OH$ using the methods described, for example, in Bols, M., *Chem. Comm.* 12:913-914 (1992); Bols, M. *Tetrahedron* 49:10049-1005 (1993); and Crich, D. and Smith M. *J. Am. Chem. Soc.* 123:9015-9020 (2001), contents of all which are herein incorporated by reference. Accordingly, the cholesteryl 6-O-acyl-α-D-glucopyranoside can be synthesized utilizing the methods described herein for the synthesis of the exemplary compound 1. In general, compound 1 can be obtained from the reaction between compound 2 or its protected derivatives and a desired electrophile (acid chloride or acid anhydride).

Scheme 1

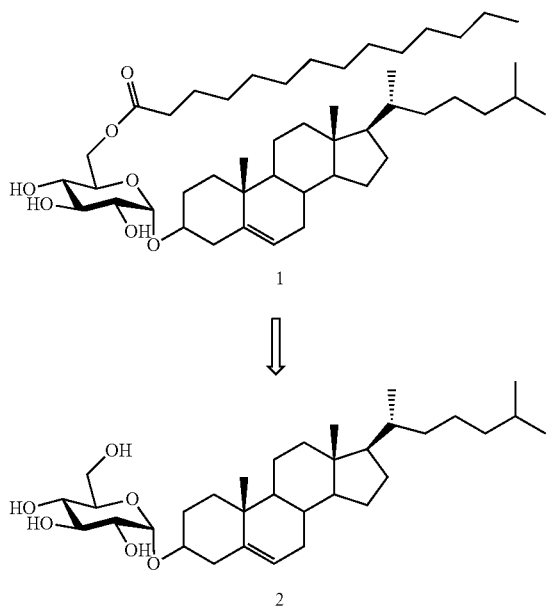

The synthesis of compound 2 can be carried out, in some embodiments, as follows. The phenyl thioglucoside (3) is prepared using the procedure described in Bols M., *Chem. Com.* 12, 913 (1992). For stereospecific introduction of saccharide unit into target molecule is accomplished using the high efficient "silicon tethered intramolecular glycosidation" method described in Bols, M et al. *Tetrahedron*, 49, 10049 (1993). The intramolecular α-glycosidation is achieved by carrying out the reaction with cholesterol (4) tethered to the 2-position of the glucosyl donor (3) by silicon linkage (compound 5), using the thioglycoside activation method reported by Crich and Smith *J. Am. Chem. Soc.* 123: 9015 (2001). O-acetyl protection groups from 6 are removed by MeONa/MeOH treatment in dichloromethane giving 2. Compound 2 is first per-trimethylsilylated by trimethylsilyl chloride/triethylamine in dichloromethane followed by selective deprotection of 6-position of glucose to give 7 (Fernandez, et al., *Carbohydrate Res.* 327: 353-365 (2000), content which is herein incorporated by reference). Reaction of 7 with acyl anhydride and 4-dimethylaminopyridine followed by removal of trimethylsilyl protection groups with methanol/aq.$KHSO_4$ provides reasonable yields of cholesteryl 6-O-acyl-α-D-glucopyranosides. The synthesized cholesteryl 6-O-acyl-α-D-glucopyranoside can be separated from a reaction mixture and further purified by a method such as column chromatography, high pressure liquid chromatography.

The compounds described herein contain one or more asymmetric centers and thus can give rise to enantiomers, diastereomers, and other stereoisomeric forms that can be defined, in terms of absolute stereochemistry, as (R)- or (S)-, or α or β. Included herein are all such possible isomers, as well as their racemic and optically pure forms. Accordingly, the sugar component of the compounds includes, but is not limited to, allose, glucose, mannose, gulose, idoes, galactose, talose, and derivatives and analogs thereof. Similarly, the sterol component includes, but is not limited to, bile acids (such as cholic acid, deoxycholic acid, chenodeoxycholic acid, glycocholic acid, taurocholic acid, deoxychlolic acid, lithocholic acid), cholesterol, 7-beta-hydroxycholesterol, 7-keto-cholesterol, 6,7-dihydroxy-cholesterol, 5,6,-epoxy-cholesterol, stigmasterol, lanosterol, beta-sitosterol, ergosterol, campesterol, brassicasterol, and derivatives and analogs thereof.

Optical isomers can be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

CHEMICAL DEFINITIONS

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene."

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, formyl, acetyl, propionyl, butyryl, valeryl, caproyl, t-butylacetyl.

The term "alkyl" refers to saturated non-aromatic hydrocarbon chains that may be a straight chain or branched chain, containing the indicated number of carbon atoms (these include without limitation methyl, ethyl, propyl, butyl, pentyl, hexanyl, which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, l-methyl-2-buten-1-yl and the like.

The term "alkynyl" refers to an alkyl that comprises at least one triple bond.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like. The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "optionally substituted" means that the specified group or moiety, such is unsubstituted or is substituted with one or more (typically 1-4 substituents) independently selected from the group of substituents listed below in the definition for "substituents" or otherwise specified.

The term "substituents" refers to a group that replaces a hydrogen at any atom of the substituted group or moiety. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

Therapeutic Applications

Certain aspects of the invention described herein are based, in part, on the discovery by the inventors that glycolipids purified from the bacterium *H. pylori*, such as the cholesterol derivative cholesteryl 6-O-tetradecanoyl-α-D-glucopyranoside, also referred to herein as 6-O-acyl α-glucoside, specifically activate NKT cells in vitro by a CD1d-restricted mechanism. Further, the inventors determined that direct administration of such glycolipids to a subject increases the total number of NKT cells, and in particular the double-negative (DN) subset of NKT cells. The inventors have found that the DN subset of NKT cells contacted with such glycolipids have immunoregulatory or regulatory properties and can suppress the subsequent development of asthma, and that this effect is active and can be transferred by such immunoregulatory NKT cells to another subject. In addition, the inventors have found that the immunoregulatory NKT cells are associated with the development and expansion of other immunoregulatory immune cells, such as Foxp3$^+$ T$_{reg}$ cells.

Accordingly, provided herein are methods for the treatment and prevention of inflammatory diseases, such as asthma or autoimmune diseases, in a subject in need thereof. Some of these methods involve administering to a subject a therapeutically effective amount of one or more of the compounds of formula (I) described herein. Other such methods involve administering to a subject a therapeutically effective amount of a population of NKT cells that have been contacted with one or more of the compounds of formula (I) described herein. In some embodiments of these methods, the compound of formula (I) is a compound of formula (II), formula (III), formula (IV), formula (V), or a cholesteryl 6-O-tetradecanoyl-α-D-glucopyranoside (also referred to herein as 6-O-acyl α-glucoside). These methods described herein are particularly aimed at therapeutic and prophylactic treatments of human subjects having or at risk for an inflammatory disease.

In one aspect, a method is provided for the prevention or treatment of an inflammatory disease in a subject in need thereof, comprising administering to a subject an effective amount of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside).

In other such aspects, a methods is provided for the prevention or treatment of an inflammatory disease in a subject in need thereof, comprising administering to a subject an effective amount of a compound of formula (VI), such as a compound of formula (VIa), formula (VIb), or α-C-Galactosylceramide.

In another aspect, provided herein is the use of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside) for preventing or treating an inflammatory disease in a subject in need thereof.

In other such aspects, provided herein is the use of a compound of formula (VI), such as a compound of formula (VIa), formula (VIb), or α-C-Galactosylceramide, for preventing or treating an inflammatory disease in a subject in need thereof.

The terms "subject" and "individual" are used interchangeably herein, and refer to an animal, for example a human, from whom the immune cells and NKT cells for use in the methods described herein can be isolated and collected from. A subject can also be the recipient of the isolated and contacted immune cells and NKT cells, or the recipient to whom an effective amount of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, is administered. For treatment of disease states that are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

The inventors have discovered that administration of a compound of formula (I), such as such as a compound of formula (II), formula (III), formula (IV), formula (V), or cholesteryl 6-O-tetradecanoyl-α-D-glucopyranoside (also referred to herein as 6-O-acyl α-glucoside), in a young subject having an immature or developing immune system can prevent the development of an inflammatory disorder in the same adult subject. In addition, the inventors have found that an immune cell population, or substantially pure or enriched NKT cell population contacted with a compound of formula (I), such as cholesteryl 6-O-tetradecanoyl-α-D-glucopyranoside, or a compound of formula (VI), such as α-C-Galactosylceramide, that is isolated from a young subject having an immature or developing immune system, when administered to an a recipient adult subject can protect that adult subject from an inflammatory disease, such as asthma. Without wishing to be bound or limited by a theory, this protection is believed to be mediated by the modulation of the properties of the developing NKT cells in the young subject, such that they develop a regulatory phenotype. In some embodiments, such regulatory NKT cells have a DN phenotype. The regulatory NKT cells are believed, without wishing to be bound or limited by a theory, to mediate this effect by further modulating the development, maturation, and/or expansion of other immune cells in the subject, including, but not limited to Foxp3$^+$ T$_{reg}$ cells. Such Foxp3$^+$ T$_{reg}$ cells can be antigen-specific or naturally occurring Foxp3$^+$ T$_{reg}$ cells.

Accordingly, for the various embodiments of the methods described herein, a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, can be administered to a subject of any age, i.e., a subject less than 100 years, less than 90 years, less than 80 years, less than 70 years, less than 60 years, less than 50 years, less than 45 years, less than 40 years, less than 35 years, less than 30 years, less than 25 years, less than 20 years, less than 15 years, or less than 10 years.

In some preferred embodiments of the aspects described herein, the subject is less than 10 years, less than 9 years, less than 8 years, less than 7 years, less than 6 years, less than 5 years, less than 4 years, less than 3 years, less than 2 years, less than 1 year, less than 11 months, less than 10 months, less than 9 months, less than 8 months, less than 7 months, less than 6 months, less than 5 months, less than 4 months, less than 3 months, less than 2 months, or less than 1 month of age. As used herein, a "young subject" can be a subject less than 10 years of age, and an "infant subject" is less than 2 years of age. In some embodiments of the aspects described herein, an infant subject being treated with the compositions and methods described herein has not been completely weaned from maternal breast milk, i.e., the infant still nurses and drinks maternal breast milk for some or all his/her nutritional requirements. In some embodiments of the aspects described herein, an infant subject being treated with the compositions and methods described herein requires breast milk, or a formula solution replicating breast milk, for some or all of his/her nutritional requirements.

In some embodiments of the aspect, a subject, such as a young subject, or an infant subject, is administered a compound of formula (I) selected from the group consisting of: cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside; 7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate-α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O- tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6-bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside. In some embodiments of the aspect, a subject, such as a young or an infant subject, is administered cholesteryl 6-O-tetradecanoyl-α-D-glucopyranoside (also referred to herein as 6-O-acyl α-glucoside).

In other aspects, an NKT cell population or a biological sample comprising NKT cells for use in the different methods of treating or preventing inflammatory diseases described herein are contacted with an effective amount of one or more compounds of formula (I), such as a compound of formula (II), formula (III), formula (IV), formula (V), or cholesteryl 6-O-tetradecanoyl-α-D-glucopyranoside) (also referred to herein as 6-O-acyl α-glucoside), or one or more compounds of formula (VI), such as a compound of formula (VIa), formula (VIb), or α-C-galactosylceramide. This contacting can be performed in vitro, ex vivo, or in vivo, as described herein.

NKT Cells and Foxp3$^+$ Regulatory T Cells

NKT cells comprise a small (0.2%) subset of T lymphocytes that share characteristics with NK cells and conventional T cells, with potent functions in modulating immunity (33). NKT cells are classified based on their TCR (T cell receptor) repertoire and the molecule by which they are presented antigen, and these cells express a relatively unique transcription factor, PLZF, that is specific for NKT cells (34) and other innate or activated T cells (35). As used herein, an "NKT cell" or "NKT cell population" includes those NKT cells that express an invariant TCR (i.e., Vα14Jα18 TCR in mice and Vα24 in humans) and have antigen presented to them by, i.e., are "restricted by," the MHC class I-like molecule, CD1d. The CD1d molecule is widely expressed by airway and intestinal epithelial cells, B cells, macrophages and dendritic cells, all of which can act as antigen presenting cells (APCs) for NKT cells. The conservation of the invariant TCR across many mammalian species indicates that it acts as a pattern recognition receptor, and that NKT cells play an important role in innate immunity, i.e., the initial immune response to pathogens. In addition, different subsets of NKT cells can be differentiated on the basis of the expression of different cell-surface markers, such as CD4 and CD8. Accordingly, NKT cells can be classified into further subsets, such as "CD4$^+$CD8$^-$" (also referred to herein as "CD4$^+$ NKT cells"), CD4$^-$CD8$^-$ (also referred to herein as "double-negative" or "DN NKT cells"), and CD4$^-$CD8$^+$ (also referred to herein as "CD8$^+$ NKT cells") based on the expression of specific cell-surface markers. In other embodiments of the aspects described herein, an NKT cell can be one that does not express an invariant TCR.

NKT cells can also be classified according to their functional properties. These functional properties include, but are not limited to, the expression or lack of expression of one or more cell-surface molecules (i.e., CD4$^-$CD8$^-$ NKT cells), the production of a specific cytokine or combination of cytokines by an NKT cell population or a subset of an NKT cell population (e.g., IFNγ, IL-4, IL-17, or any combination therein), or by the ability of an NKT cell population or a subset of an NKT cell population to modulate or induce another population(s) of immune cells (e.g., induction or expansion of a Foxp3+ regulatory T cell ($T_{reg}$) population). Accordingly, in some embodiments of the aspects described herein, a population of NKT cells can be classified as "regulatory" or "immunoregulatory," if administration or modulation of such an NKT population protects against the development or progression of a disease condition, either through a direct mechanism, an indirect mechanism, or a combination of such mechanisms. For example, in some embodiments, a regulatory population of NKT cells is a population of DN NKT cells generated using the compositions and methods described herein.

NKT cells comprise only a small proportion of the total hematopoietic cells or immune cells in a subject. "Hematopoietic cells" or "immune cells," as described herein, (also known as white blood cells (WBCs), or leukocytes) refer to cells of the immune system that defend the body against both infectious disease and foreign materials. Hematopoietic cells are all produced and derived from a multipotent cell in the bone marrow known as a hematopoietic stem cell (HSC). Hematopoietic cells or immune cells are found throughout the body, including the blood and lymphatic system, and as used herein, refer to all types of hematopoietic cells throughout their differentiation from self-renewing HSCs through immature precursors of the various hematopoietic lineages to and including mature function hematopoietic cells, as would be understood by one of skill in the art. Mature hematopoietic cell lineages include, but are not limited to, neutrophils, basophils, eosinophils, lymphocytes (CD4 and CD8 T cells, B cells, NKT cells), NK (natural killer) cells, monocytes, macrophages, and dendritic cells. Accordingly, NKT cells for use with the compositions and methods described herein can be obtained by a variety of methods and from any biological sample comprising such immune cells.

The term "biological sample" as used herein refers to a cell or population of cells or a quantity of tissue or fluid from a subject comprising one or more NKT cells. Most often, the biological sample has been removed from a subject, but the term "biological sample" can also refer to cells or tissue analyzed in vivo, i.e. without removal from the subject. Biological samples include, but are not limited to, whole blood, bone marrow, cord blood, tissue sample, e.g., lung, spleen or lymph node sample, or biopsies, scrapes (e.g. buccal scrapes), plasma, serum, urine, saliva, cell culture, or cerebrospinal fluid. A biological sample or tissue sample can refer to a sample of tissue or fluid isolated from a subject, including but not limited to, for example, peripheral blood, bone marrow, thymus, lymph nodes, splenic tissue, liver tissue, lung tissue, cord blood, plasma, sputum, serum, lung lavage fluid, tumor biopsy, urine, stool, spinal fluid, pleural fluid, nipple aspirates, lymph fluid, the external sections of the skin, respiratory, intestinal, and genitourinary tracts, tears, saliva, milk, cells (including but not limited to hematopoietic cells), tumors, organs, and also samples obtained from in vitro cell cultures. Such in vitro cell cultures include NKT cells that have been cultured in vitro after isolation from a subject, NKT cells that have been generated ex vivo or in vitro from a non-NKT cell population, such as a hematipoietic progenitor cell populations, or other multi- and pluripotent stem cell populations, including but not limited to human embryonic stem cells and induced pluripotent stem cells.

In some embodiments of the aspects described herein, a biological sample comprising NKT cells refers to a sample isolated from a subject, such as a peripheral blood sample, thymus sample, bone marrow sample, splenic sample, lung tissue sample, cord blood sample, or liver sample, which is then further processed, for example, by cell sorting, to obtain a population of haematopoietic cells comprising NKT cells. In other embodiments of the aspects described herein, a biological sample comprising NKT cells refers to an in vitro culture of expanded NKT cells. In some embodiments, the sample is from a resection, bronchoscopic biopsy, or core needle biopsy. In some embodiments, a biological sample comprises a stem cell population, including an induced pluripotent stem cell population. In addition, fine needle aspirate samples are used. Samples can be either paraffin-embedded or frozen tissue. The sample can be obtained by removing a sample of cells from a subject, but can also be accomplished by using previously isolated cells (e.g., isolated from another subject), or by using the compositions and performing the methods described herein in vivo.

Activation of an NKT cell through the invariant TCR results in the rapid production of large amounts of cytokines, such as IL-4 and IFN-γ, particularly from mature NKT cells found in adult mice and humans. In contrast, activation of NKT cells in neonates or in cord blood, which are immature, results in only relatively small amounts of cytokines (36, 37). Activation of an NKT cell population can also lead to expansion of that NKT cell population by proliferation. Depending on the agent used to activate an NKT cell population, a specific subset of an NKT cell population can be preferentially expanded, e.g., only DN NKT cells undergo expansion. Activation of an NKT cell can also lead to modulation of cell-surface phenotypes, such as up-regulation or down-regulation of one or more cell-surface markers. For example, activation of an NKT cell can lead to down-regulation of the invariant TCR. Accordingly, as used herein "activation" of an NKT cell, an NKT cell population, or a biological sample comprising NKT cells includes, but is not limited to, any change or modulation, such as an increase in, cytokine production by, changes in expression of cell-surface markers on, expansion of/proliferation of, or any combination therein, one or more NKT cells in an NKT cell population, or biological sample comprising NKT cells.

Regulatory T cells or $T_{reg}$ cells play an important role for the maintenance of immunological tolerance by suppressing the action of autoreactive effector cells and have been shown to be critically involved in preventing the development of autoimmune reactions (S. Sakaguchi, Nat Immunol 6:345-352, (2005)). While a number of cell surface molecules are used to characterize and define $T_{reg}$ cells, the most common being $CD4^+CD25^{hi}$ expression, the transcription factor FOXP3 is specifically expressed in these cells and has been shown to be a critical factor for the development and function of $T_{reg}$ cells. Accordingly, as described herein, a "regulatory T cell" or "$T_{reg}$" refers to those T cells that have immunoregulatory properties and the ability to suppress the proliferation and/or effector function of other T cell populations, and that, in some embodiments, express the transcription factor Foxp3.

Accordingly, in one aspect, methods are provided for the treatment or prevention of an inflammatory disease in a subject in need thereof, comprising administering to a subject an effective amount of an NKT cell population contacted with a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide.

In some embodiments of this aspect and all such aspects described herein, the NKT cell population being contacted with a compound of formula (I) or a compound of formula (VI) and being administered to a subject, is obtained or isolated from a second subject of any age. In some such embodiments, the NKT cell population is contacted in vivo in a donor subject prior to being isolated and administered to the subject in need thereof. The donor subject can be of any age. In some preferred embodiments, the donor subject is less than 10 years, less than 9 years, less than 8 years, less than 7 years, less than 6 years, less than 5 years, less than 4 years, less than 3 years, less than 2 years, less than 1 year, less than 11 months, less than 10 months, less than 9 months, less than 8 months, less than 7 months, less than 6 months, less than 5 months, less than 4 months, less than 3 months, less than 2 months, or less than 1 month of age. In some embodiments, the subject is a young subject or an infant subject. In some embodiments, the infant has not been completely weaned from breast milk, i.e., the infant still nurses and drinks breast milk from a mother for some or all his/her nutritional requirements. In some embodiments of the aspects described herein, the infant requires breast milk or a formula solution replicating breast milk for some or all of his/her nutritional requirements.

In some embodiments of the aspects described herein, a compound of formula (I) selected from the group consisting of: cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside; 7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate-α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O-tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6-bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside. In some embodiments of the aspect, a subject is administered cholesteryl 6-O-tetradecanoyl-α-D-glucopyranoside (also referred to herein as 6-O-acyl α-glucoside).

In some embodiments of this aspect, the contacting of the NKT cell population can be in vitro, ex vivo, or in vivo. As used herein, in vivo (Latin for "within the living") refers to those methods using a whole, living organism, such as a human subject. For example, in some embodiments, an NKT cell population is contacted by direct administration of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, to a subject, such as an infant or young subject. Administration for the methods described herein include, but are not limited to, injection, infusion, instillation, inhalation, ingestion, rectal, and topical (including buccal and sublingual) administration, and are discussed in further detail below.

As used herein, "ex vivo" (Latin: out of the living) refers to those methods that are performed outside the body of a subject, and refers to those procedures in which an organ, cells, or tissue are taken from a living subject for a procedure, e.g., contacting a biological sample comprising NKT cells with a compound of formula (I), such as cholesteryl 6-O-tetradecanoyl-α-D-glucopyranoside) (also referred to herein as 6-O-acyl α-glucoside), or a compound of formula (VI), such as α-C-Galactosylceramide, and then returning the contacted sample to a subject. As used herein, "in vitro" refers to those methods performed outside of a subject, such as an in vitro cell culture experiment. For example, NKT cells being cultured in vitro can be contacted with a compound of formula (I), such as cholesteryl 6-O-tetradecanoyl-α-D-glucopyranoside (also referred to herein as 6-O-acyl α-glucoside), or a compound of formula (VI), such as α-C-Galactosylceramide, and then returned to an incubator for expansion or growth in the presence of the compound of formula (I) or formula (VI) prior to being used or administered according to the methods described herein.

In some such embodiments of the aspects described herein, contacting an NKT cell population or a biological sample comprising NKT cells with an effective amount of one or more compounds of formula (I), such as cholesteryl 6-O-tetradecanoyl-α-D-glucopyranoside (also referred to herein as 6-O-acyl α-glucoside), or one or more compounds of formula (VI), such as α-C-Galactosylceramide, "activates" the NKT cells of the NKT cell population or biological sample relative to a comparable, control NKT cell population or biological sample that is not contacted with one or more compounds of formula (I) or formula (VI). It is preferred that the degree of activation of NKT cells in the NKT cell population or biological sample comprising NKT cells is at least 10% higher, at least 20% higher, at least 30% higher, at least 40% higher, at least 50% higher, at least 60% higher, at least 70% higher, at least 80% higher, at least 90% higher, at least 95% higher, at least 2-fold higher, at least 3-fold higher, at least 4-fold higher, at least 5-fold higher, at least 6-fold higher, at least 7-fold higher, at least 7-fold higher, at least 9 fold higher, at least 10 fold higher, at least 25-fold higher, at least 50-fold higher, at least 100-fold higher, at least 1000-fold higher, or more, than a comparable control treated NKT cell population or a biological sample comprising NKT cells, which have been treated identically except for the addition of the compound(s) of formula (I) or formula (VI).

In some embodiments of this aspect, the NKT cell population being contacted or used in the methods described herein, comprises allogeneic NKT cells obtained from one or more donors. As used herein, "allogeneic" refers to NKT cells or biological samples comprising NKT cells obtained from one or more different donors of the same species, where the genes at one or more loci are not identical. For example, an NKT cell population being administered to a subject may be obtained from one more unrelated donors, or from one or more non-identical siblings. In some embodiments, syngeneic NKT cell populations can be used, such as those obtained from genetically identical animals, or from identical twins. In other embodiments of this aspect, the NKT cells are autologous NKT cells. As used herein, "autologous" refers to NKT cells or biological samples comprising NKT cells obtained or isolated from a subject and being administered to the same subject, i.e., the donor and recipient are the same.

In some embodiments of this aspect, the contacting of the NKT cell population occurs in the presence of one or more antigen-presenting cells (APCs). An antigen-presenting cell (APC), as used herein, refers to those cells that can present a compound of formula (I), such as cholesteryl 6-O-tetradecanoyl-α-D-glucopyranoside (also referred to herein as 6-O-acyl α-glucoside), to the TCR of an NKT cell, preferably such that the NKT cell becomes activated as defined herein, and include, but are not limited to, dendritic cells (DCs), macrophages, B-cells, and epithelial cells. Preferably, the APCs use CD1d to present the compound of formula (I) to the NKT cell population or biological sample comprising NKT cells.

Other aspects described herein provide methods for the treatment or prevention of an inflammatory disease in a subject in need thereof. In such aspects, the method comprises: (a) isolating a plurality of immune cells from a first subject, wherein the immune cells comprise an NKT population; (b) contacting said isolated immune cells with an effective amount of a compound of formula (I) or formula (VI; and (c) administering to a second subject an effective amount of the plurality of isolated immune cells contacted with a compound of formula (I) or formula (VI), wherein said second subject has or is at risk for an inflammatory disease.

Another such aspect provides a method of treating or preventing an inflammatory disease in a subject in need thereof, comprising: (a) administering an effective amount of a compound of formula (I) or formula (VI); (b) isolating a plurality of immune cells from the first subject, wherein the immune cells comprise an NKT population; and (c) administering to a second subject an effective amount of the plurality of immune cells isolated from the first subject administered a compound of formula (I) or formula (VI), wherein said second subject has or is at risk for an inflammatory disease.

In some embodiments of these aspects, the first subject is of any age. In some preferred embodiments, the first subject is less than 10 years, less than 9 years, less than 8 years, less than 7 years, less than 6 years, less than 5 years, less than 4 years, less than 3 years, less than 2 years, less than 1 year, less than 11 months, less than 10 months, less than 9 months, less than 8 months, less than 7 months, less than 6 months, less than 5 months, less than 4 months, less than 3 months, less than 2 months, or less than 1 month of age. In some embodiments, the first subject is a young subject or an infant subject. In some embodiments of the aspects described herein, an infant subject being treated with the compositions and methods described herein has not been completely weaned from breast milk, i.e., the infant still nurses and drinks breast milk from a mother for some or all his/her nutritional requirements. In some embodiments of the aspects described herein, an infant subject being treated with the compositions and methods described herein requires breast milk or a formula solution replicating breast milk for some or all of his/her nutritional requirements.

In some embodiments of these aspects and all such aspects described herein, the compound of formula (I) can be a compound of formula (II), formula (III), formula (IV), or formula (V). In other embodiments of these aspects, a compound of formula (VI), can be a compound of formula (VIa) or formula (VIb).

In some embodiments of these aspects, a compound of formula (I) selected from the group consisting of: cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside;

7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate-α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O-tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6-bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside. In some embodiments of these aspects, the compound of formula (I) is cholesteryl 6-O-tetradecanoyl-α-D-glucopyranoside) (also referred to herein as 6-O-acyl α-glucoside).

Immune cells, or hematopoietic cells, for use with the compositions and methods described herein can be obtained from any suitable biological sample as is described herein. A variety of methods and techniques can be used for obtaining the immune cells, as is known to one of skill in the art. Suitable methods by which a plurality of immune cells can be obtained include, but are not limited to, cell isolation techniques such as magnetic sorting, or flow cytometric based sorting techniques.

In some embodiments of the aspects described herein, NKT cells for use with the compositions and methods described herein can be generated ex vivo or in vitro from a non-NKT cell population, such as a hematipoietic progenitor cell population, or other multi- and pluripotent stem cell populations, including but not limited to human embryonic stem cells and induced pluripotent stem (iPS) cells. Such non-NKT cell populations can be autologous cell populations or donor-derived cell populations.

As used herein, the term "pluripotent" refers to a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). The term "multipotent" when used in reference to a "multipotent cell" refers to a cell that has the developmental potential to differentiate into cells of one or more germ layers, but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white (e.g., T cells, NKT cells), platelets, etc. . . . ), but it cannot form neurons.

The term "stem cell" as used herein refers to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. The term "embryonic stem cell" as used herein refers to naturally occurring pluripotent stem cells of the inner cell mass of the embryonic blastocyst (see, for e.g., U.S. Pat. Nos. 5,843,780; 6,200,806; 7,029,913; 7,584,479, which are incorporated herein by reference). Embryonic stem cells are pluripotent and give rise during development to all derivatives of the three primary germ layers: ectoderm, endoderm and mesoderm. In some embodiments, induced pluripotent stem cells can be generated using any method known to one of skill in the art, for use in generating NKT cells suitable for use with the methods and compositions described herein.

The terms "isolate, "isolation techniques," and "methods of isolation," as used herein, refers to a process or processes whereby a cell or population of cells is removed from a subject or biological sample in which it was originally found, or a descendant of such a cell or cells. The term "isolated population" with respect to an isolated population of cells, as used herein, refers to a population of cells that has been removed and separated from a biological sample, or a mixed or heterogeneous population of cells found in such a sample. Such a mixed population includes, in one embodiment, a population of peripheral blood cells obtained from isolated blood. In another embodiment, an isolated population of immune cells is obtained from the bone marrow. In another embodiment, an isolated population of immune cells is obtained from a cell suspension of a tissue sample comprising immune cells, such as a lymph node, or a thymus or spleen sample. In some embodiments, an isolated population is a substantially pure population of cells as compared to the heterogeneous population from which the cells were isolated or enriched from. In some embodiments of this aspect and all such aspects described herein, the isolated population comprises a population of immune or hematopoietic cells. In other embodiments of this aspect and all aspects described herein, the isolated population is an population enriched for NKT cells or a subset of NKT cells, or is a substantially pure population of NKT cells or a subset of NKT cells.

In some embodiments of this aspect and all such aspects described herein, the isolated immune cell population comprises a substantially pure population of NKT cells as compared to a heterogeneous population of immune cells comprising various immune cell types from which the NKT cells were derived or isolated. In some embodiments, an isolated immune cell population, is further cultured in vitro, e.g., in the presence of growth factors or cytokines, to further expand the number of NKT cells in the isolated immune cell population or substantially pure NKT cell population. The isolated immune cells or NKT cells can be put into such cultures before or after contacting with a compound of formula (I). Such culture can be performed using any method known to one of skill in the art, for example, those methods described in the Examples section. In some embodiments, an isolated immune cell population or substantially pure NKT cell population obtained by the methods disclosed herein are later introduced into a second different subject, or re-introduced into the same subject from which the cell population was originally isolated, i.e., the first and second subject are the same.

The term "substantially pure," with respect to an isolated immune cell population or NKT cell population, refers to a population of cells that is at least about 75%, at least about 80%, at least about 85%, at least about 90%, at least about 95%, at least about 98%, or at least about 99% pure, with respect to the immune cells or NKT cells making up the total cell population. In other words, the terms "substantially pure" or "essentially purified," with regard to a population of NKT cells isolated for use in the methods as disclosed herein, refers to a population of NKT cells that contain fewer than about 25%, fewer than about 20%, fewer than about 15%, fewer than about 10%, fewer than about 9%, fewer than about 8%, fewer than about 7%, fewer than about 6%, fewer than about 5%, fewer than about 4%, fewer than about 4%, fewer than about 3%, fewer than about 2%, fewer than about 1%, or less than 1%, of cells that are not NKT cells as defined by the terms herein.

The terms "enriching" or "enriched" are used interchangeably herein and mean that the yield (fraction) of cells of one type, such as NKT cells or a particular subset of NKT cells, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

Some embodiments of these aspects further encompass methods to expand a population of immune cells or a population of substantially pure or enriched NKT cells, wherein the expanded population of NKT cells is a substantially pure or enriched population of NKT cells. In some embodiments of the aspect, a population of immune cells or a population of substantially pure or enriched NKT cells is contacted with a compound of formula (I), such as cholesteryl 6-O-tetradecanoyl-α-D-glucopyranoside (also referred to herein as 6-O-acyl α-glucoside), or a compound of formula (VI), such as α-C-Galactosylceramide, in an amount and time sufficient to activate the NKT cells in the plurality of immune cells or the population of substantially pure or enriched NKT cells. In some embodiments, the activation of the NKT cells in the plurality of immune cells or the population of substantially pure or enriched NKT cells causes an expansion of the NKT cells, changes the cytokine production by the NKT cells, alters cell-surface marker expression of the NKT cells, or any combination thereof.

As used herein, the terms "expanding", "expansion," "proliferating," and "proliferation", refer to an increase in the number of cells in a population (growth) by means of cell division. Cell proliferation is generally understood to result from the coordinated activation of multiple signal transduction pathways in response to the environment, including growth factors and other mitogens. For example, in some embodiments, a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, is contacted with a population of immune cells or a substantially pure or enriched NKT cell population to cause NKT cell proliferation or expansion. These expanded NKT cells can then be used in the methods described herein. Cell proliferation can also be promoted by release from the actions of intra- or extracellular signals and mechanisms that block or negatively affect cell proliferation.

In some embodiments of this aspect and all such aspects described herein, the method further comprises purifying or enriching for an NKT cell population from the contacted immune cells prior to the administration of the immune cells to the second subject.

A variety of methods to isolate an immune cell population, or a substantially pure or enriched population of NKT cells for use in the methods described herein, are available to a skilled artisan, including immunoselection techniques, such as high-throughput cell sorting using flow cytometric methods, affinity methods with antibodies labeled to magnetic beads, biodegradable beads, non-biodegradable beads, and antibodies panned to surfaces including dishes and combination of such methods.

"Flow cytometry" refers to a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. A common variation of flow cytometric techniques is to physically sort particles based on their properties, so as to purify populations of interest, using "fluorescence-activated cell sorting." As defined herein, "fluorescence-activated cell sorting" refers to a flow cytometric method for sorting a heterogeneous mixture of cells from a biological sample into two or more containers, one cell at a time, based upon the specific light scattering and fluorescent characteristics of each cell and provides fast, objective and quantitative recording of fluorescent signals from individual cells as well as physical separation of cells of particular interest. Accordingly, fluorescence-activated cell sorting can be used with the methods described herein to isolate or enrich for immune cell or NKT cell populations.

In other embodiments of this aspect and all aspects described herein, isolation and enrichment for immune cell or NKT cell populations can be performed using bead based sorting mechanisms, such as magnetic beads. In such methods, the sample of cells to be isolated or enriched is contacted with magnetic beads coated with antibodies or other agents, such as tetramers, against one or more specific cell-surface antigens, such as, for example, TCRβ, CD4, and CD8. Using such methods, cells can be separated positively or negatively with respect to the particular cell-surface markers. As defined herein, "positive selection" refers to techniques that result in the isolation or enrichment of cells expressing specific cell-surface markers, while "negative selection" refers techniques that result in the isolation or enrichment of cells not expressing specific cell-surface markers. In some embodiments, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select NKT cells or a subset of NKT cells. Accordingly, in some embodiments of the aspect, the purified or enriched for NKT cell population is a purified DN (CD4⁻CD8⁻) NKT cell population or an NKT cell population enriched for DN (CD4⁻CD8⁻) NKT cells.

Modes of Administration

The compounds of formula (I), such as a compound of formula (II), formula (II), formula (IV), formula (V), or cholesteryl 6-O-tetradecanoyl-α-D-glucopyranoside (also referred to herein as 6-O-acyl α-glucoside), or the compounds of formula (VI), such as a compound of formula (VIa), formula (VIb), or α-C-Galactosylceramide; or the isolated immune cells, substantially pure NKT cells, or enriched NKT cells contacted with a compound of formula (I) or formula (VI), as described herein, can be administered to a subject in need thereof by any appropriate route which results in an effective treatment in the subject. As used herein, the terms "administering," and "introducing" are used interchangeably and refer to the placement of the isolated immune cells, substantially pure NKT cells, or enriched NKT cells, isolated and contacted using the methods as disclosed herein, into a subject by a method or route which results in at least partial localization of such cells at a desired site, such as a site of inflammation, such that a desired effect(s) is produced. For example, in some embodiments of the aspects described herein, a substantially pure population of NKT cells contacted with a compound of formula (I), such as cholesteryl 6-O-tetradecanoyl-α-D-glucopyranoside (also referred to herein as 6-O-acyl α-glucoside), or a compound of formula (VI), such as α-C-Galactosylceramide is administered to the lungs during or following an asthma attack.

Exemplary modes of administration include, but are not limited to, injection, infusion, instillation, inhalation, ingestion, rectal, and topical (including buccal and sublingual) administration. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compounds of formula (I) or formula (VI), or the isolated immune cells, substantially pure NKT cells, or enriched NKT cells contacted with a compound of formula (I) or formula (VI), for use in the methods described herein are administered by intravenous infusion or injection.

The phrases "parenteral administration" and "administered parenterally" as used herein, refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein refer to the administration of the compounds of formula (I) or population of cells contacted with compounds of formula (I) other than directly into a target site, tissue, or organ, such as the lung, such that it enters the subject's circulatory system and, thus, is subject to metabolism and other like processes.

For the clinical use of the methods described herein, administration of the compounds of formula (I), such as a compound of formula (II), formula (II), formula (IV), formula (V), or cholesteryl 6-O-tetradecanoyl-α-D-glucopyranoside (also referred to herein as 6-O-acyl α-glucoside), or the compounds of formula (VI), such as a compound of formula (VIa), formula (VIb), or α-C-Galactosylceramide; or the isolated immune cells, substantially pure NKT cells, or enriched NKT cells contacted with a compound of formula (I), such as a compound of formula (II), formula (II), formula (IV), formula (V), or cholesteryl 6-O-tetradecanoyl-α-D-glucopyranoside, or contacted with a compound of formula (VI), such as a compound of formula (VIa), formula (VIb), or α-C-Galactosylceramide described herein can include formulation into pharmaceutical compositions or pharmaceutical formulations for parenteral administration, e.g., intravenous; mucosal, e.g., intranasal; enteral, e.g., oral; topical, e.g., transdermal; ocular, or other mode of administration. In some embodiments of the aspects described herein, the compounds of formula (I), or the isolated immune cells, substantially pure NKT cells, or enriched NKT cells contacted with a compound of formula (I) described herein can be administered along with any pharmaceutically acceptable compound, material, or composition which results in an effective treatment in the subject. Thus, a pharmaceutical formulation for use in the methods described herein can contain a compound of formula (I), such as a compound of formula (II), formula (III), formula (IV), formula (V), or cholesteryl 6-O-tetradecanoyl-α-D-glucopyranoside) (also referred to herein as 6-O-acyl α-glucoside), or a cell population contacted with a compound of formula (I) of the invention in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the activity of, carrying, or transporting the compounds of formula (I), or the isolated immune cells, substantially pure NKT cells, or enriched NKT cells contacted with a compound of formula (I), from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

As described herein, the compounds of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, can be specially formulated for administration of the compound to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, a compound of formula (I) can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Further embodiments of the formulations and modes of administration of the compounds of formula (I), or the isolated immune cells, substantially pure NKT cells, or enriched NKT cells contacted with a compound of formula (I), such as cholesteryl 6-O-tetradecanoyl-α-D-glucopyranoside (also referred to herein as 6-O-acyl α-glucoside), that can be used in the methods of the invention described herein are illustrated below.

Aerosol Formulations.

A compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, can be administered directly to the airways in the form of an aerosol or by nebulization. For use as aerosols, a compound of formula (I), such as a cholesteryl 6-O-tetradecanoyl-α-D-glucopyranoside, can be packaged in a pressurized aerosol container together with suitable propellants, for example, hydrocarbon propellants like propane, butane, or isobutane with conventional adjuvants. A compound of formula (I), such as a cholesteryl 6-O-tetradecanoyl-α-D-glucopyranoside (also referred to herein as 6-O-acyl α-glucoside), can also be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases to date being those which are chemically inert to a compound of formula (I), such as a cholesteryl 6-O-tetradecanoyl-α-D-glucopyranoside (also referred to herein as 6-O-acyl α-glucoside). Exemplary gases including, but are not limited to, nitrogen, argon or helium can be used.

A compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, can also be administered directly to the airways in the form of a dry powder. For use as a dry powder, a compound of formula (I), such as a cholesteryl 6-O-tetradecanoyl-α-D-glucopyranoside (also referred to herein as 6-O-acyl α-glucoside), can be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume. Dry powder aerosols for inhalation therapy are generally produced with mean diameters primarily in the range of <5 µm. As the diameter of particles exceeds 3 µm, there is increasingly less phagocytosis by macrophages. However, increasing the particle size also has been found to minimize the probability of particles (possessing standard mass density) entering the airways and acini due to excessive deposition in the oropharyngeal or nasal regions.

Suitable powder compositions include, by way of illustration, powdered preparations of a compound of formula (I), such as cholesteryl 6-O-tetradecanoyl-α-D-glucopyranoside (also referred to herein as 6-O-acyl α-glucoside), thoroughly intermixed with lactose, or other inert powders acceptable for intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, *J. Pharm. Res.,* 1: 565-569 (1990); Zanen, P. and Lamm, J.-W. J. *Int. J. Pharm.,* 114: 111-115 (1995); Gonda, I. "Aerosols for delivery of therapeutic an diagnostic agents to the respiratory tract," in *Critical Reviews in Therapeutic Drug Carrier Systems,* 6:273-313 (1990); Anderson et al., *Am. Rev. Respir. Dis.,* 140: 1317-1324 (1989)) and have potential for the systemic delivery of peptides and proteins as well (Patton and Platz, *Advanced Drug Delivery Reviews,* 8:179-196 (1992)); Timsina et. al., *Int. J. Pharm.,* 101: 1-13 (1995); and Tansey, I. P., *Spray Technol. Market,* 4:26-29 (1994); French, D. L., Edwards, D. A. and Niven, R. W., *Aerosol Sci.,* 27: 769-783 (1996); Visser, J., *Powder Technology* 58: 1-10 (1989)); Rudt, S. and R. H. Muller, J. *Controlled Release,* 22: 263-272 (1992); Tabata, Y, and Y. Ikada, *Biomed. Mater. Res.,* 22: 837-858 (1988); Wall, D. A., *Drug Delivery,* 2: 10 1-20 1995); Patton, J. and Platz, R., *Adv. Drug Del. Rev.,* 8: 179-196 (1992); Bryon, P., *Adv. Drug. Del. Rev.,* 5: 107-132 (1990); Patton, J. S., et al., *Controlled Release,* 28: 15 79-85 (1994); Damms, B. and Bains, W., *Nature Biotechnology* (1996); Niven, R. W., et al., *Pharm. Res.,* 12(9); 1343-1349 (1995); and Kobayashi, S., et al., *Pharm. Res.,* 13(1): 80-83 (1996), contents of all of which are herein incorporated by reference in their entirety.

Parenteral Dosage Forms.

Parenteral dosage forms of compounds of formula (I), such as a compound of formula (II), formula (III), formula (IV), formula (V), or cholesteryl 6-O-tetradecanoyl-α-D-glucopyranoside (also referred to herein as 6-O-acyl α-glucoside), or compounds of formula (VI), such as a compound of formula (VIa), formula (VIb), or α-C-Galactosylceramide; or the isolated immune cells, substantially pure NKT cells, or enriched NKT cells contacted with a compound of formula (I) or formula (VI), can also be administered to a subject with a inflammatory disorder by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Oral Dosage Forms.

Pharmaceutical compositions comprising a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or compounds of formula (VI), such as a compound of formula (VIa), formula (VIb), or α-C-Galactosylceramide, can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and can be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

Typical oral dosage forms of the compositions described herein are prepared by combining the pharmaceutically acceptable salt of a compound of formula (I), such as a cholesteryl 6-O-tetradecanoyl-α-D-glucopyranoside (also referred to herein as 6-O-acyl α-glucoside), in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition.

Disintegrants are used in the pharmaceutical compositions described herein to provide tablets that disintegrate when exposed to an aqueous environment. A sufficient amount of disintegrant that is neither too little nor too much to detrimentally alter the release of the active ingredient(s) should be used to form solid oral dosage forms of the compounds of formula (I) described herein. The amount of disintegrant used varies based upon the type of formulation and mode of administration, and is readily discernible to those of ordinary skill in the art. Disintegrants that can be used to form pharmaceutical compositions of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions described herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Plano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The compositions and methods described herein further encompass lactose-free pharmaceutical formulations and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The formulations of the compounds of formula (I) described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms.

In some embodiments of the aspects described herein, a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the compounds of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, described herein. Examples include, but are not limited to, those described in U.S. Pat. Nos. 3,845,770; 3,916,899; 3,536, 809; 3,598,123; 4,008,719; 5,674,533; 5,059,595; 5,591, 767; 5,120,548; 5,073,543; 5,639,476; 5,354,556; 5,733, 566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

A particular and well-known osmotic drug delivery system is referred to as OROS® (Alza Corporation, Mountain View, Calif. USA). This technology can readily be adapted for the delivery of compounds of formula (I) and compositions thereof of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds of formula (I) and compositions thereof of the disclosure include, but are not limited to, the OROS® Push-Pull™, Delayed Push-Pull™, Multi-Layer Push-Pull™, and Push-Stick™ Systems. Additional OROS® systems that can be used for the controlled oral delivery of compounds and compositions of the disclosure include OROS®-CT and L-OROS®; see, Delivery Times, vol. 11, issue II (Alza Corporation).

In some embodiments of the aspects described herein, a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the inflammatory disorder occurs continuously in the subject, for example where the subject has continuous or chronic symptoms of a respiratory disorder. Each pulse dose can be reduced and the total amount of a compound of, for example, formula (I), administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Topical, Transdermal and Mucosal Dosage Forms.

Topical dosage forms of the compounds of formula (I) or formula (VI) described herein include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990). and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer compounds of formula (I) or formula (VI) described herein include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. In addition, depending on the specific tissue to be treated, additional components may be used prior to, in conjunction with, or subsequent to treatment with a compound of formula (I). For example, penetration enhancers can be used to assist in delivering the active ingredients to or across the tissue.

Administration of Cells.

A variety of means for administering cells, such as autologous or donor-derived populations of isolated NKT cells, substantially pure NKT cells, or enriched NKT cells contacted with a compound of formula (I), such as a compound of formula (II), formula (II), formula (IV), formula (V), or cholesteryl 6-O-tetradecanoyl-α-D-glucopyranoside, or contacted with a compound of formula (VI), such as a compound of formula (VIa), formula (VIb), or α-C-Galactosylceramide described herein, to subjects, are known to those of skill in the art. Such methods can include systemic injection, for example i.v. injection, or implantation of cells into a target site in a subject. Cells can be inserted into a delivery device which facilitates introduction by injection or implantation into the subject. Such delivery devices can include tubes, e.g., catheters, for injecting cells and fluids into the body of a recipient subject. In one preferred embodiment, the tubes additionally have a needle, e.g., through which the cells can be introduced into the subject at a desired location. The cells can be prepared for delivery in a variety of different forms. For example, the cells can be suspended in a solution or gel or embedded in a support matrix when contained in such a delivery device. Cells can be mixed with a pharmaceutically acceptable carrier or diluent in which the cells remain viable.

Pharmaceutically acceptable carriers and diluents include saline, aqueous buffer solutions, solvents and/or dispersion media. The use of such carriers and diluents is well known in the art. The solution is preferably sterile and fluid. Preferably, prior to the introduction of cells as described herein, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

It is preferred that the mode of cell administration is relatively non-invasive, for example by intravenous injection, pulmonary delivery through inhalation, topical, or intranasal administration. However, the route of cell administration will depend on the tissue to be treated and may include implantation. Methods for cell delivery are known to those of skill in the art and can be extrapolated by one skilled in the art of medicine for use with the methods and compositions described herein.

Direct injection techniques for cell administration can also be used to stimulate transmigration of cells through the entire vasculature, or to the vasculature of a particular organ, such as for example the lung, liver, or kidney or any other organ. This includes non-specific targeting of the vasculature. One can target any organ by selecting a specific injection site, e.g., a liver portal vein. Alternatively, the injection can be performed systemically into any vein in the body. If so desired, a mammal or subject can be pre-treated with an agent, for example an agent is administered to enhance cell targeting to a tissue (e.g., a homing factor) and can be placed at that site to encourage cells to target the desired tissue.

Treatment of Inflammatory Disorders

Inflammatory diseases or disorders, as used herein, refer to those diseases or abnormalities associated with aberrant or excessive inflammatory responses, and comprise a large, group of disorders which underlie a vast variety of human diseases. The immune system is often involved with inflammatory disorders, as demonstrated in allergic reactions, autoimmune diseases, and some myopathies, with many immune system disorders resulting in abnormal inflammation. Non-immune diseases with etiological origins in inflammatory processes can include cancer, atherosclerosis, and ischaemic heart disease.

As used herein, inflammation refers to the complex biological response of vascular tissues to harmful stimuli, such as pathogens, damaged cells, or irritants. Inflammation is a protective attempt by the organism to remove the injurious stimuli as well as initiate the healing process for the tissue. Inflammation is not a synonym for infection, though inflammation can be caused by an infection. Examples of inflammatory disorders associated with inflammation include, but are not limited to asthma, autoimmune diseases, chronic inflammation, chronic prostatitis, glomerulonephritis, hypersensitivities, inflammatory bowel diseases, pelvic inflammatory disease, reperfusion injury, rheumatoid arthritis, transplant rejection, vasculitis, an interstitial cystitis.

Accordingly, inflammatory diseases that can be treated or prevented using the methods described herein include, but are not limited to, inflammatory diseases of the respiratory system, allergic disorders, and autoimmune diseases.

In the methods of treatment and prevention of inflammatory diseases described herein, the administration of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide; or the isolated immune cells, substantially pure NKT cells, or enriched NKT cells contacted with a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, can be for either "prophylactic" or "therapeutic" purposes.

When provided prophylactically, a compound of formula (I) or formula (VI) or the isolated immune cells, substantially pure NKT cells, or enriched NKT cells contacted with a compound of formula (I) or formula (VI) can be administered to a subject in advance of any symptom, e.g. asthma attack. The prophylactic administration of a compound of formula (I) or formula (VI), or the isolated immune cells, substantially pure NKT cells, or enriched NKT cells contacted with a compound of formula (I) or formula (VI) serves to prevent an inflammatory disorder, as disclosed herein.

When provided therapeutically, a compound of formula (I), such as cholesteryl 6-O-tetradecanoyl-α-D-glucopyranoside (also referred to herein as 6-O-acyl α-glucoside), or formula (VI) or the isolated immune cells, substantially pure NKT cells, or enriched NKT cells contacted with a compound of formula (I) or formula (VI), is provided at (or after) the onset of a symptom or indication of an inflammatory disorder, e.g., upon the onset of an allergic respiratory disorder.

Accordingly, as used herein, the terms "treat," "treatment," "treating," "prevention" or "amelioration" refer to both therapeutic treatment and prophylactic or preventative measures, wherein the object is to prevent, delay the onset, reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with an inflammatory disease, such as, but not limited to, asthma. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment). For example, any reduction in inflammation, bronchospasm, bronchoconstriction, shortness of breath, wheezing, lower extremity edema, ascites, productive cough, hemoptysis, or cyanosis in a subject suffering from a respiratory disorder, such as asthma, no matter how slight, would be considered an alleviated symptom. In some embodiments of the aspects described herein, the symptoms or a measured parameter of a disease or disorder are alleviated by at least 5%, at least 10%, at least 20%, at least 30%, at least 40%, at least 50%, at least 60%, at least 70%, at least 80%, at least 90%, or at least 100%, upon administration of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, or isolated immune cells, substantially pure NKT cells, or enriched NKT cells contacted with a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, as compared to a control or non-treated subject. Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated. "Treatment" can also mean prolonging survival as compared to expected survival if not receiving treatment.

The term "effective amount" as used herein refers to the amount of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide; or isolated immune cells, substantially pure NKT cells, or enriched NKT cells contacted with a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide, needed to alleviate at least one or more symptom of the disease or disorder, and relates to a sufficient amount of pharmacological composition to provide the desired effect, i.e., prevent the development of allergic asthma. The term "therapeutically effective amount" therefore refers to an amount of a compound of formula (I), such as cholesteryl 6-O-tetradecanoyl-α-D-glucopyranoside (also referred to herein as 6-O-acyl α-glucoside), or isolated immune cells, substantially pure NKT cells, or enriched NKT cells contacted with a compound of formula (I) using the compositions and methods as described herein, that is sufficient to effect a particular effect when administered to a typical subject, such as one who has or is at risk for asthma. An effective amount as used herein would also include an amount sufficient to prevent or delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage may vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose may be formulated in animal models to achieve a circulating plasma concentration range that includes the IC50 (i.e., the concentration of the compound of formula (I), such as cholesteryl 6-O-tetradecanoyl-α-D-glucopyranoside (also referred to herein as 6-O-acyl α-glucoside), which achieves a half-maximal inhibition of symptoms) as determined in cell culture, or in an appropriate animal model. Levels in plasma may be measured, for example, by high performance liquid chromatography. The effects of any particular dosage can be monitored by a suitable bioassay. The dosage may be determined by a physician and adjusted, as necessary, to suit observed effects of the treatment.

The administration of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide; or isolated immune cells, substantially pure NKT cells, or enriched NKT cells contacted with a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide; or contacting NKT cells with a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside), or a compound of formula (VI), such as a compound of formula (VIa), formula (VIb), or α-C-Galactosylceramide; are useful for methods of treating and preventing inflammatory respiratory diseases, as described herein.

The terms "respiratory disorder" and "respiratory disease" are used interchangeably herein and refer to any condition and/or disorder relating to respiration and/or the respiratory system, including the lungs, airways, or other components of the respiratory system. A respiratory disorder can be allergic or non-allergic. Respiratory diseases and disorders suitable for treatment or prevention using the methods described in the various aspects herein include, but are not limited to, asthma, airway hyperreactivity, lung inflammation, chronic obstructive pulmonary disease (COPD), pneumonia, sinusitis, hypersensitivity pneumonitis, pulmonary infiltrate with eosinophilia, environmental lung disease, bronchiectasis, cystic fibrosis, interstitial lung disease, primary pulmonary hypertension, pulmonary thromboembolism, disorders of the pleura, acute respiratory distress syndrome, mesothelioma, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary venoocclusive disease, rheumatoid lung disease, sarcoidosis, and Wegener's granulomatosis. In some embodiments, the respiratory disorder to be treated or prevented is characterized by increased responsiveness of the tracheas and bronchi to various stimuli, for example, allergens, resulting in a widespread narrowing of the airways.

As used herein, "airway hyperreactivity" refers to the narrowing of air passages of the lungs ("airways") in response to stimuli such as pollen, grains in the air, changes of temperature, emotional shock, or exercise. Airway hyperreactivity (AHR) is a cardinal feature of asthma, and is observed in all forms of asthma, including asthma induced with allergen and non-allergen such as ozone exposure.

The term "COPD" is generally applied to chronic respiratory disease processes characterized by the persistent obstruction of bronchial air flow. Typical COPD patients are those suffering from conditions such as bronchitis, cystic fibrosis, asthma or emphysema.

Asthma refers to a chronic inflammatory disease of the respiratory system in which the airway occasionally constricts, becomes inflamed, and is lined with excessive amounts of mucus, often in response to one or more triggers. Asthma can be defined simply as reversible airway obstruction in an individual over a period of time. Asthma can be allergic/atopic or non-allergic. Asthma is characterized by the presence of cells such as eosinophils, mast cells, basophils, and activated T lymphocytes in the airway walls. With chronicity of the process, secondary changes occur, such as thickening of basement membranes and fibrosis. The disease is characterized by increased airway hyperresponsiveness to a variety of stimuli, and airway inflammation and constriction. This airway narrowing causes symptoms such as wheezing, shortness of breath, chest tightness, and coughing. The airway constriction responds to bronchodilators. Between episodes, most patients feel well but can have mild symptoms and they can remain short of breath after exercise for longer periods of time than the unaffected individual. The symptoms of asthma can range from mild to life threatening.

Asthma can be triggered by such things as exposure to an allergen (allergic asthma), or non-allergens (non-allergic asthma) such as cold air, pollution (e.g., ozone), warm air, moist air, exercise or exertion, or emotional stress. In children, the most common triggers are viral illnesses such as those that cause the common cold (Zhao J., et. al., 2002, *J Pediatr. Allergy Immunol.* 13: 47-50).

Common allergens that trigger the allergic asthma include "seasonal" pollens, year-round dust mites, molds, pets, and insect parts, foods, such as fish, egg, peanuts, nuts, cow's milk, and soy, additives, such as sulfites, work-related agents, such as latex. Approximately 80% of children and 50% of adults with asthma also have allergies.

Common irritants that can trigger asthma in airways that are hyperreactive include respiratory infections, such as those caused by viral "colds," bronchitis, and sinusitis, medication drugs, such as aspirin, other NSAIDs (nonsteroidal antiinflammatory drugs), and beta blockers (used to treat blood pressure and other heart conditions), tobacco smoke, outdoor factors such as ozone, smog, weather changes, and diesel fumes; indoor factors such as paint, detergents, deodorants, chemicals, and perfumes; nighttime GERD (gastroesophageal reflux disorder); exercise, especially under cold dry conditions; work-related factors such as chemicals, dusts, gases, and metals; emotional factors, such as laughing, crying, yelling, and distress; and hormonal factors, such as in premenstrual syndrome.

Regardless of the trigger, asthma is associated with reversible airway obstruction and airway hyperreactivity (AHR), an increased sensitivity of the airways to nonspecific stimuli such as cold air or respiratory irritants, and can be quantitated by responsiveness to methacholine or histamine. A patient diagnosed as asthmatic will generally have multiple indications over time, including wheezing, asthmatic attacks, and a positive response to methacholine challenge, i.e., a PC20 on methacholine challenge of less than about 4 mg/ml. The basic diagnosis and measurement of asthma is peak flow rates and the following diagnostic criteria are used by the British Thoracic Society (Pinnock H., and Shah R., 2007, *Br. Med. J.* 334 (7598): 847-50): ≥20% difference on at least three days in a week for at least two weeks; ≥20% improvement of peak flow following treatment, for example: 10 minutes of inhaled β-agonist (e.g., salbutamol), six week of inhaled corticosteroid (e.g., beclometasone), and 14 days of 30 mg prednisolone; and ≥20% decrease in peak flow following exposure to a trigger (e.g., exercise). Further guidelines for diagnosis may be found, for example, in the National Asthma Education Program Expert Panel Guidelines for Diagnosis and Management of Asthma, National Institutes of Health, 1991, Pub. No. 91-3042.

The term "allergic respiratory disorder" or "hypersensitivity disease" refers to allergic diseases and/or disorders of the lungs or respiratory system. Allergic disorders are characterized by hypersensitivity to an allergen.

As used herein, "allergy" shall refer to those inflammatory disorders caused by acquired hypersensitivity to a substance (allergen). Allergic conditions include eczema, allergic rhinitis or coryza, hay fever, bronchial asthma, urticaria (hives) and food allergies, and other atopic conditions. A "subject having an allergy" is a subject that has or is at risk of developing an allergic reaction in response to an allergen. An "allergen" refers to a substance that can induce an allergic or asthmatic response in a susceptible subject. The term "atopic" as used herein refers to a state of atopy or allergy to an allergen or a state of hypersensitivity to an allergen. Typically, atopic refers to Type I hypersensitivity which results from release of mediators (e.g., histamine and/or leukotrines) from IgE-sensitized basophils and mast cells after contact with an antigen (allergen). An example of atopic is atopic asthma, which is allergic asthma and is characterized by an IgE response.

Other atopic conditions suitable for use with the compositions and methods described herein include allergic rhinitis, gastrointestinal allergies, including food allergies, eosinophilia, conjunctivitis, and glomerulonephritis, as well as certain pathogen susceptibilities such as helminthic (e.g., leishmaniasis) and certain viral infections, including human immunodeficiency virus (HIV), and certain bacterial infections, including tuberculosis and lepromatous leprosy.

Allergens of interest include antigens found in food, such as strawberries, peanuts, milk polypeptides, egg whites, etc. Other allergens of interest include various airborne antigens, such as grass pollens, animal danders, house mite feces, etc. Molecularly cloned allergens include *Dermatophagoides pteryonyssinus* (Der Pl); LoI pl-V from rye grass pollen; a number of insect venoms, including venom from jumper ant *Myrmecia pilosula; Apis mellifera* bee venom phospholipase A2 (PLA2 and antigen 5S; phospholipases from the yellow jacket *Vespula maculifrons* and white faced hornet *Dolichovespula maculata*; a large number of pollen polypeptides, including birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., *gramineae*, etc. Other allergens of interest are those responsible for allergic dermatitis caused by blood sucking arthropods, e.g. Diptera, including mosquitos (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order Siphonaptera, including the genera *Xenopsylla, Pulex* and *Ctenocephalides felis*. The specific allergen may be a polysaccharide, fatty acid moiety, polypeptide, etc.

The term "allergic rhinitis" as used herein is characterized by any of the following symptoms: obstruction of the nasal passages, conjuctival, nasal and pharyngeal itching, lacrimation, sneezing, or rhinorrhea. These symptoms usually occur in relationship to allergen exposure.

The term "non-allergic inflammatory disorder" as used herein refers to an inflammatory disorder that is not a result from or caused by an allergen. Thus, a non-allergic respiratory disorder is caused by other mechanisms not relating to hypersensitivity to an innocuous agent or allergen.

The methods using the compounds of formula (I), such as a compound of formula (II), formula (III), formula (IV), formula (V), or cholesteryl 6-O-tetradecanoyl-α-D-glucopyranoside (also referred to herein as 6-O-acyl α-glucoside), or compounds of formula (VI), such as a compound of formula (VIa), formula (VIb), or α-C-Galactosylceramide; or cells contacted with compound (I), such as a compound of formula (II), formula (III), formula (IV), formula (V), or cholesteryl 6-O-tetradecanoyl-α-D-glucopyranoside (also referred to herein as 6-O-acyl α-glucoside), or with a compound of formula (VI), such as a compound of formula (VIa), formula (VIb), or α-C-Galactosylceramide, as described in the various aspects herein, may also be particularly beneficial for the treatment or prevention autoimmune diseases in a subject. "Autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include cancer cells.

Accordingly, in some embodiments, the autoimmune diseases to be treated or prevented using the methods described herein, include, but are not limited to: rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., *pemphigus vulgaris*), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In one embodiment of the aspects described herein, the autoimmune disease is selected from the group consisting of multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

In other embodiments of the methods described herein, the inflammatory disease or disorder is host versus graft disease (HVGD). In a further such embodiment, the subject being treated with the methods described herein is an organ or tissue transplant recipient. In another embodiment, the methods described herein are used for increasing transplantation tolerance in a subject, comprising administering to the subject a therapeutically effective amount of a compound of formula (I), such as a compound of formula (II), formula (III), formula (IV), formula (V), or cholesteryl 6-O-tetradecanoyl-α-D-glucopyranoside (also referred to herein as 6-O-acyl α-glucoside); or a compound of formula (VI), such as a compound of formula (VIa), formula (VIb), or α-C-Galactosylceramide; or a cell population contacted with a compound of formula (I) or formula (VI). In one such embodiment, the subject is a recipient of an allogenic transplant. The transplant can be any organ or tissue transplant, including but not limited to heart, kidney, liver, skin, pancreas, bone marrow, skin or cartilage. "Transplantation tolerance," as used herein, refers to a lack of rejection of the donor organ by the recipient's immune system.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

Materials and Methods

Mice.

Wild-type BALB/c ByJ and T-bet$^{-/-}$ (C.129S6-Tbx21tm1Glm/J) mice were purchased from The Jackson Laboratory. Jα18$^{-/-}$ mice were gifts from M. Taniguchi and T. Nakayama (Chiba University, Chiba, Japan). TLR7$^{-/-}$ mice were generated by Dr. Shizuo Akira (Chiba University, Chiba, Japan), and the Vα14 Tg mice were provided by Dr. Albert Bendelac (University of Chicago, Chicago, Ill., USA). These strains were backcrossed to BALB/c for more than 10 generations. DO11.10 X Rag$^{-/-}$ mice were provided by Dr. Abul Abbas (UCSF, San Francisco). For studies in suckling mice, BALB/c, TLR7$^{-/-}$ and T-bet$^{-/-}$ mice were bred, and the offspring were infected at 2 wks of age, then weaned at 3 wks. The Animal Care and Use Committee at Children's Hospital Boston approved all animal protocols.

Influenza A Infection.

Two-week-old mice (suckling mice) or 8-week-old (adult mice) were anesthetized with 3% isoflurane and inoculated intranasally (i.n.) with influenza A virus (strain Mem/71 [H3N1]) in 20 µl PBS for suckling mice, or 50 µl PBS for adult mice. The virus is a reassortant influenza virus strain carrying the hemagglutinin of A/Memphis/1/71 (H3) and the neuraminidase of A/Bellamy/42 (N1). The virus was grown and harvested from 10-day embryonated chicken eggs as described[59]. The dose of virus used ($1.2 \times 10^4$ PFU/mouse) causes nonlethal pneumonia of both suckling and adult mice with complete virus clearance around day 7 after infection. Control (mock infected) mice were treated with i.n. allantoic fluid (A.F) diluted 1:500 in PBS.

Reagents.

α-GalCer was synthesized by P. B. Savage (Brigham Young University, Provo, Utah, USA). *H. pylori* glycolipids were extracted and purified as described herein. Chemical synthesis of *H. pylori* glycolipid PI57 (Cholesteryl 6-O-tetradecanoyl-α-D-glucopyranoside, 1) is described below and was based on 1H, 13C NMR spectrometry, TLC analysis, ES-mass spectrometry of lipids from *H. pylori* SS1 and a human *H. pylori* S strains (FIGS. 11A-11D), and on data reported for purified *H. pylori* glycolipids (30). An analogue of α-C-GalCer, called GCK151, which has activity with mouse and human NKT cells (27), was synthesized by Dr. Richard W. Franck, Hunter College of CUNY. Compound PI57 has been characterized by $^1$H, $^{13}$C NMR spectrometry, TLC analysis, ES-mass spectrometry. These data are in a good agreement with analytical ones reported for purified *H. pylori* glycolipids.

*H. pylor* glycolipid PI57 (cholesteryl-6-O-tetradecanoyl-α-D-glucoside, 1) was synthesized as shown in scheme 2.

Scheme 2

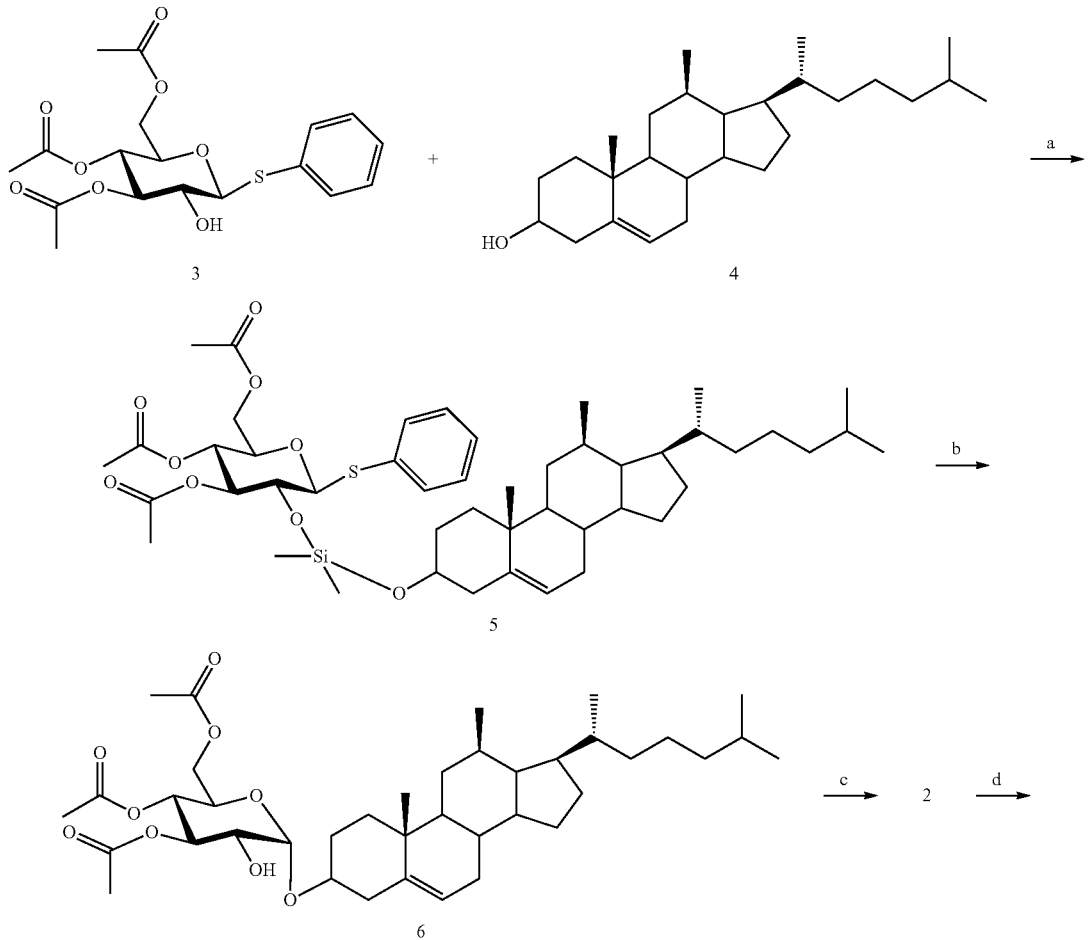

-continued

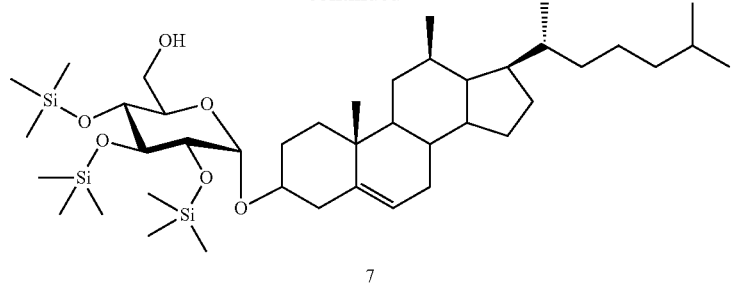

7

Reagents (yields in parentheses): (a) Cl₂SiMe₂, pyridine, CH₂Cl₂, imidazole, (90%). (b) benzensulfinylpiperidine/trifloromethanesulfonic anhydride, di-tretBu-Py, CH₂Cl₂, -70° C., (82%). (c) NaOMe/MeOH, CH₂Cl₂, (quant). (d) TMSCl, N₃Et, CH₂Cl₂, (quant); acetone/MeOH/AcOH, (e) myristic anhydride, DMAP, CH₂Cl₂; MeOH/KHSO₄ aq., (62%).

Preparation of Compound 5

Compound 3 was prepared using the procedure of Bols, M. *Chem. Comm.* 12:913-914 (1992). To compound 3 (2.0 g, 5.06 mmol) in dry toluene (30 ml) and dry pyridine (7 ml) under Ar was added dimethylsilyldichloride (3 ml, 5 eq), and the mixture was stirred for 1 h at 25° C. The reaction mixture was concentrated under reduced pressure to 12 ml and solution of cholesterol (4) (1.54 g, 4.0 mmol), imidazole (320 mg, 4.75 mmol) in CH₂Cl₂ (8 ml) was added. The reaction mixture was stirred for 6 h and saturated aqueous sodium hydrogencarbonate (1 ml) was added. The product was extracted with CH₂Cl₂ (3×15 ml). The combined extract was washed with water (2×20 ml), dried over Na₂SO₄ and concentrated under reduced pressure. The product 5 (3.02 g, 90% yield) was obtained as a clear oil after chromatography (SiO₂, hexane:EtOAc 20:1). NMR ($^1$H, CDCl₃) δ 7.51 (m, 1H), 7.32-7.16 (m, 4H), 5.31 (brs, 1H), 5.13 (t, J=9.6 Hz, 1H), 4.94 (t, J=9.6 Hz, 1H), 4.62 (d, J=8.6 Hz, 1H), 4.20 (dd, J=3.4, J=11.0 Hz, 1H), 4.12 (dd, J=2.1, J=11.0 Hz, 1H), 3.78 (t, J=9.2 Hz, 1H), 3.70-3.56 (m, 2H), 2.21 (m, 2H), 2.06 (s, 3H), 2.01 (s, 3H), 1.98 (s, 1H), 1.90-1.01 (27H), 0.91 (s, 3H), 0.88 (d, J=5.6 Hz, 3H), 0.81 (d, J=5.6 Hz, 6H), 0.64 (s, 1H), 0.21 (s, 3H), 0.11 (s, 1H). ES-MS m/e ([M+Na]⁺) 863.7.

Preparation of cholesteryl 3,4,6-tri-O-acetyl-α-D-glucopyranoside (6)

The triflic anhydride (0.660 mL, 3.93 mmol) was added to a solution of compound 5 (3 g, 3.57 mmol), di-tert-Bu-pyridine (0.890 g, 4.64 mmol) and benzensulfinylpiperidine (0.875 g, 3.93 mmol) in CH₂Cl₂ (20 mL) at −70° C. The reaction mixture was stirred for 1 h and saturated aqueous sodium hydrogencarbonate (1 mL) was added. The product was extracted with CH₂Cl₂ (3×10 ml), and the combined extracts were dried over Na₂SO₄ and concentrated under reduced pressure. The product 6 (1.97 g, 82% yield) was obtained as a solid foam after chromatography (SiO₂, hexane:EtOAc 4:1). NMR ($^1$H, CDCl₃) 5.41 (brs, 1H), 5.19 (t, J=9.6 Hz, 1H), 5.01 (d, J=3.4, 1H), 4.92 (t, J=9.6 Hz, 1H), 4.21 (dd, J=3.4, J=11.0 Hz, 1H), 4.11 (m, 2H), 3.61 (m, 1H), 3.48 (m, 1H), 2.21 (m, 2H), 2.06 (s, 6H), 2.01 (s, 3H), 1.90-1.01 (27H), 0.91 (s, 3H), 0.88 (d, J=5.6 Hz, 3H), 0.81 (d, J=5.6 Hz, 6H), 0.64 (s, 1H). NMR ($^{13}$C, CDCl₃) δ 170.2, 169.8, 168.8, 139.3, 121.5, 96.2, 78.4, 72.7, 69.8, 67.3, 66.9, 61.3, 55.3, 41.5, 39.2, 38.8, 38.6, 36.1, 35.8, 34.9, 31.1, 30.0, 27.3, 27.2, 27.1, 23.4, 23.0, 20.0, 19.8, 19.7, 18.5, 11.0. ES-MS m/e ([M+Na]⁺) 697.6.

Preparation of cholesteryl-α-glucopyranoside (2)

To a solution of 6 (1 g, 1.48 mmol) in CH₂Cl₂-MeOH (6 mL, 1:1, v/v) was added NaOMe (1 mL, 1M sol. In MeOH) with vigorous stirring. The reaction mixture was stirred at 20° C. for 3 h and HCl (1 mL, 1M) was added. The organic phase was washed with water (2×2 ml), dried over Na₂SO₄ and concentrated under reduced pressure. The product 2 (0.81 g, 100% yield) was obtained as a solid and was employed in the next step without further purification. NMR ($^1$H, CD₃OD:CDCl₃ 1:1) δ 5.32 (brs, 1H), 4.81 (d, J=3.4, 1H), 3.80 (t, J=9.6 Hz, 1H), 3.75-3.62 (m, 5H), 3.48 (m, 1H), 3.39 (dd, J=2.4, 11.0 Hz, 1H), 2.21 (m, 2H), 1.90-1.01 (27H), 0.91 (s, 3H), 0.88 (d, J=5.6 Hz, 3H), 0.81 (d, J=5.6 Hz, 6H), 0.64 (s, 1H). NMR ($^{13}$C, d₆-DMSO:CDCl₃ 4:1) δ 139.2, 119.7, 95.6, 75.1, 71.7, 71.3, 70.3, 68.9, 59.5, 40.4, 39.1, 38.8, 38.5, 38.2, 37.9, 37.7, 37.4, 35.3, 34.8, 28.2, 10.2. ES-MS m/e ([M+Na]⁺) 571.4.

Preparation of cholesteryl 6-O-tetradecanoyl-α-D-glucopyranoside (1)

To a solution of 2 (400 mg, 0.73 mmol) in CH₂Cl₂ (3 mL) and NEt₃ (0.44 mL, 3.64 mmol) TMSCl (0.46 mL, 3.64 mmol) was added with vigorous stirring. The reaction mixture was stirred at 20° C. for 4 h and saturated aqueous sodium hydrogencarbonate (3 mL) was added. The product was extracted with CH₂Cl₂ (3×8 ml), and the combined extracts were dried over Na₂SO₄ and concentrated under reduced pressure. The crude compound was employed in the next step without further purification.

A solution of compound in acetone-MeOH-AcOH (1.6: 2.2:0.2, v/v/v, 4 mL) was stirred at 20° C. for 2 h and saturated aqueous sodium hydrogencarbonate (3 mL) was added. The product was extracted with CH₂Cl₂ (3×4 ml), and the combined extracts were dried over Na₂SO₄ and concentrated under reduced pressure. The crude compound 7 was employed in the next step without further purification.

To a solution of compound 7 in CH₂Cl₂ (3 mL) myristic anhydride (0.19 g, 0.88 mmol) and DMAP (10 mg) were added with vigorous stirring. The reaction mixture was stirred at 24° C. for 4 h. MeOH (1 mL) and KHSO₄ (0.5 mL. 1M sol. in H₂O) were added and stirring continue for 1 h. The product was extracted with CH₂Cl₂ (3×6 ml), and the combined extracts were dried over Na₂SO₄ and concentrated under reduced pressure.

The product 1 (0.34 g, 62% yield) was obtained as a solid foam after chromatography (SiO$_2$, CHCl$_3$-MeOH, 12:1). NMR ($^1$H, CD$_3$OD:CDCl$_3$ 1:2) δ 5.26 (brs, 1H), 4.82 (d, J=3.84, 1H), 4.36 (dd, J=2.13, 11.95 Hz, 1H), 4.08 (dd, 11.0, 11.95 Hz, 1H), 3.80 (m, 1H), 3.56 (t, J=9.52 Hz, 1H), 3.42 (m, 1H), 3.36 (dd, J=3.84, 9.52, Hz, 1H), 3.20 (t, J=9.50, 1H), 2.21-0.6 (m, 71H). ES-MS m/e ([M+Na]$^+$) 781.7.

Lipid Extraction and Purification.

To extract polar lipids, 20 ml of CHCl$_3$, CH$_3$OH (2:1, v/v) was added to the *H. pylori* pellets and the suspension was stirred for 6 h. Supernatant was removed and the pellets were re-extracted twice with 15 ml of CHCl$_3$, CH$_3$OH (2:1, v/v). The combined organic phases were concentrated and the lipids were re-extracted by Folch method. The lipid extract was dissolved in 15 ml of Folch low phase and washed three times with 4 ml of upper phase.

The final purification of the individual glycolipids was achieved by silica gel (Fluka, 60 mesh) column chromatography using stepwise gradient of chloroform/methanol (40:1 to 4:1, v/v).

The lipid extract was examined by TLC on aluminum-backed plates of silica gel 60 F$_{254}$ (Merck 5554), using CHCl$_3$, CH$_3$OH, H$_2$O (65:25:4, v/v/v) or CHCl$_3$, CH$_3$OH (6:1, v/v). Glycolipids were visualized by spraying plates with α-naphthol/sulfuric acid followed by gentle charring of plates. Other types of lipids were visualized by spraying with 5% ethanolic molybdophosphoric acid and charring, or by using a Dittmer and Lester reagent that is specific for phospholipids.

NMR Analysis.

Deuterated solvents were from Aldrich. Glycolipids NMR spectrum were recorded in CDCl$_3$-CD$_3$OD (2:1, v/v). NMR spectra were recorded on a Bruker DRX500 operating at 500.13 MHz for $^1$H or Bruker AV300 operating at 300 MHz for $^1$H. All spectra were run at 300 K. Data were acquired and processed using XWINNMR version 2.6 software on a Silicon Graphics work station. All two-dimensional NMR data were acquired nonspinning Data points (2048) were used in acquisition for the fast domain (F2), and 512 points were used in the incremented domain (F1).

Mass Spectrometric Analysis.

Glycolipids were dissolved in dichloromethane-methanol (2:1, v/v) and analyzed by Electrospray ionisation mass spectrometry (Micronos LCT) in positive or negative mode.

Results Described in FIGS. 11A-11D.

After fractionation of lipid extracts from SS1 *H. pylori* and *H. pylori* S form by silica gel column chromatography, two major glycolipids were isolated. Glycolipid AGlc-Chol has the same R$_f$ 0.49 for both *H. pylori* strains (TLC, chloroform-methanol (6:1, v/v) as well as MS-spectrum of positive mode ES-MS (781.9 [M+Na]$^+$ m/z) (not shown). The second glycolipid Glc-Chol has equal for both strains R$_f$ 0.26 (TLC, chloroform-methanol (6:1, v/v) as well as MS-spectrum of positive mode ES-MS (571.4 [M+Na]$^+$ m/z).

Figure 4A:
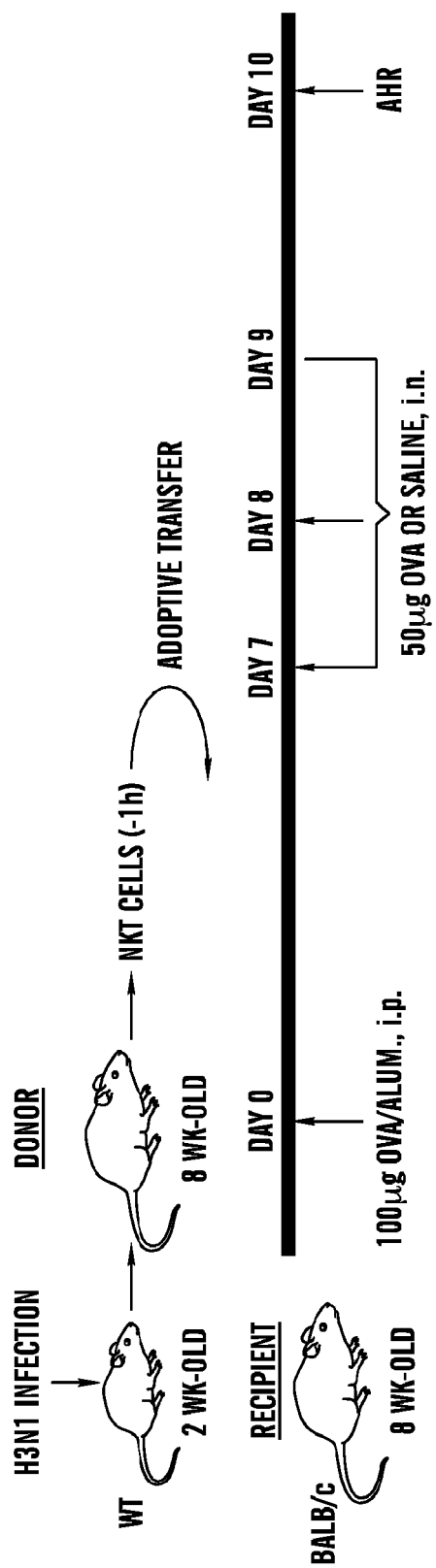
FIGS. 4A-4J demonstrate that H3N1-exposed NKT cells suppress AHR and increase OVA-specific Tregs.

AGlc-Chol lipid ES-MS spectrum in negative mode showed an ion peaks at m/z 757.5 (sup. FIG. 4a) assignable to a [M–H]$^-$ and at m/z 547.3 assignable to a [M–H]$^-$ of glycolipid Glc-Chol. The difference in 210 Da between peaks corresponded the lost of myristic acid (C14:0) fragment.

Figure 4B:
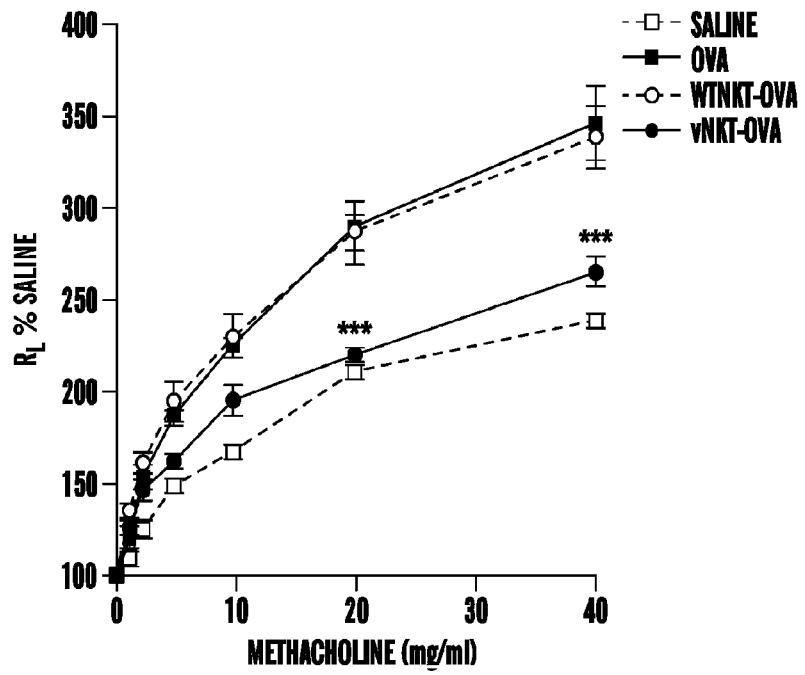

These data are in agreement with reported for *H. pylori* cholesteryl glucosides (67). Indeed, $^1$H NMR spectra of AGlc-Chols recorded in CDCl$_3$-CD$_3$OD (2:1, v/v) (500.13 MHz) were identical (sup. FIG. 4b and data not shown) and in agreement with cholesteryl-6-O-tetradecanoyl-α-glucopyranoside structure. Based on the assignment of AGlc-Chol $^1$H-$^1$H COSY NMR and proton coupling constants, we confirmed the alpha configuration of glucopyranose with fatty acid substitution at position 6 (FIG. 11C). The small J$_{1,2}$ coupling constant (3.84 Hz) of H-1 at 4.82 ppm indicated an α-anomeric configuration. The large coupling constant of H-2 (dd) at 3.36 ppm J$_{2,3}$ (9.52 Hz), H-3 (t) at 3.56 ppm J$_{3,4}$ (9.52 Hz) correlates with gluco-configuration of sugar. The downfield shift of H-6 (dd) at 4.08 ppm and H-6' (dd) at 4.38 ppm protons indicates that fatty acid esterifies the 6 position of glucose. Altogether, these data indicate cholesteryl-6-O-tetradecanoyl-α-glucopyranoside structure.

Figure 11B:
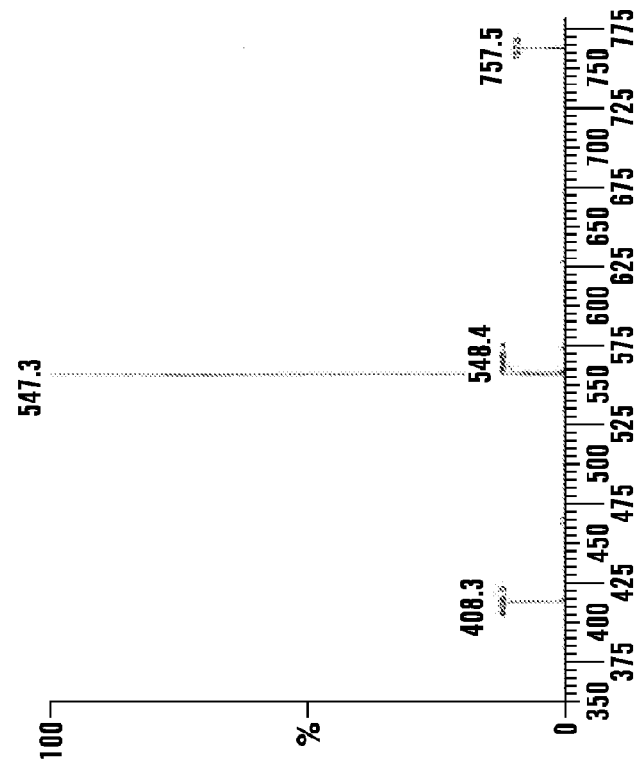
FIGS. 11A-11D demonstrate $^1$H, $^{13}$C NMR spectrometry, TLC analysis, and ES-mass spectrometry data of lipids from H. pylori SS1, a human H. pylori S strains and synthetic PI57 lipid.
Figure 11A:
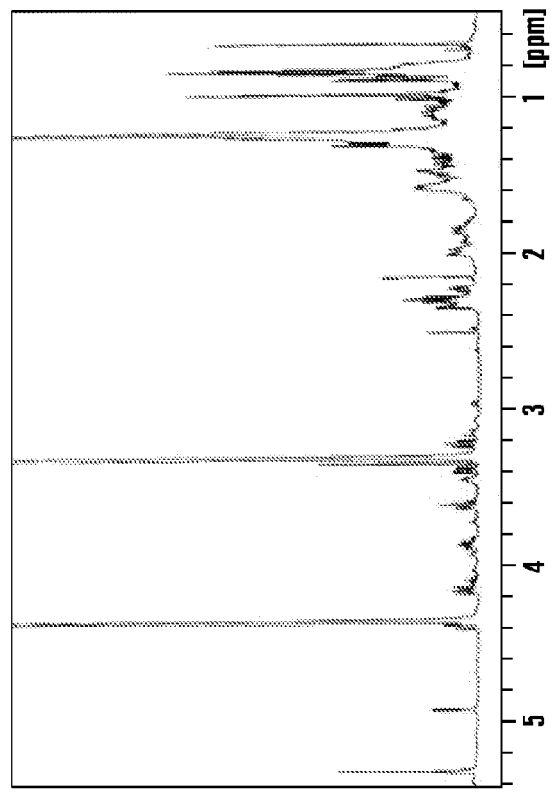
Figure 11D:
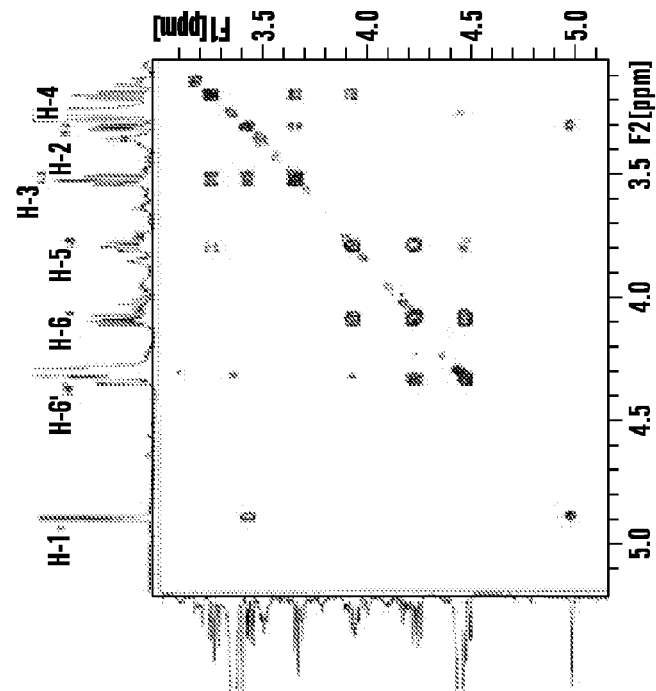
Figure 11C:
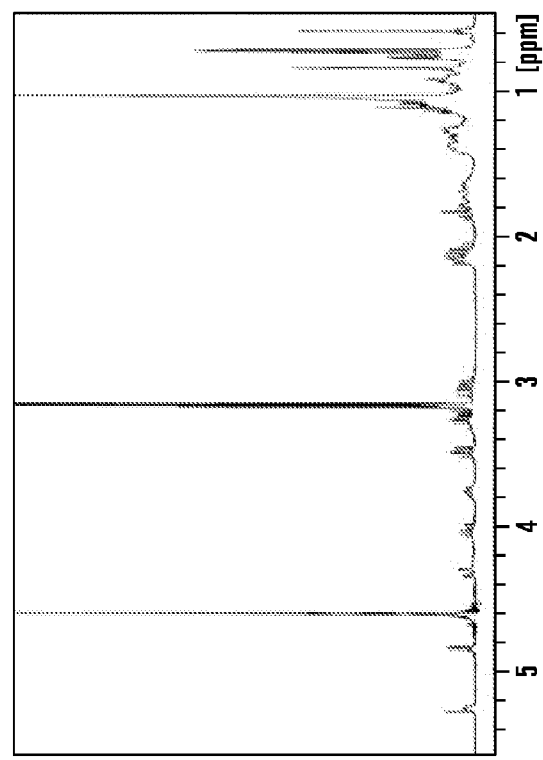

Compound PI57, the synthetic analog of AGlc-Chol, has near identical $^1$H NMR spectrum to the natural glycolipid AGlc-Chol (recorded in CDCl$_3$-CD$_3$OD (2:1, v/v) (300.0 MHz) (FIG. 11D).

The $^1$H NMR spectrum of Glc-Chol and its synthetic analog PI56 corresponds to cholesteryl-α-glucopyranoside (67).

PI57 Loaded CD1d Tetramers.

To generate PI57 loaded mCD1d monomers, a 10-fold molar excess of PI57 in DMSO at 2 mg/ml was incubated with biotinylated-mCD1d (from the NIH Tetramer facility) in 2 mM CHAPS and 20 mM Tris pH7.0 overnight at room temperature. The mCD1d monomers were tetramerized by adding SA-PE (S868, Invitrogen) to the lipid-loaded monomers as previous described (60).

Induction of AHR and measurement of airway responsiveness in the OVA model.

To induce AHR, BALB/c mice were sensitized with 100 μg of OVA (Sigma-Aldrich) in alum administered i.p (on day 0). After sensitization, mice were exposed to intranasal antigen (50 μg OVA/day) or normal saline for 1 day (day 7; single dose challenge protocol), or for 3 consecutive days (days 7, 8, 9). AHR was assessed on the day after last OVA-challenge. Control mice received i.p. injection of PBS and intranasal administrations of normal saline.

Collection and Analysis of Bronchoalveolar Lavage (BAL) Fluid.

Immediately after the AHR measurement, mice were euthanized and the lungs were lavaged twice with 0.5 ml of PBS, and the fluid was pooled. Cells in BAL fluid were counted and analyzed, as previously described[20]. The relative number of different types of leukocytes was determined from slide preparations of BAL fluid stained with Diff-Quik solution (Dade Behring).

Lung and Spleen Cells Isolation.

Whole lungs were flushed with PBS injected into the right ventricle, removed, and rinsed in PBS. The lungs were then diced on a wax board before incubating in 9.6 ml of RPMI 1640 medium with 0.1% DNase I (fraction IX; Sigma-Aldrich) and 1.6 mg/ml collagenase (CSL4; Worthington Biochemicals) at 37° C. on an orbital shaker for 30 min. The digest was passed multiple times through an 18-gauge needle and allowed to incubate for another 30 min before filtered. RBC were removed by 4-min incubation in lysis buffer (Sigma-Aldrich) at room temperature. Single-cell suspensions of spleen lymphocytes were obtained by mechanical disruption and RBC lysis.

Histopathologic Analysis.

The lungs were taken from mice, infused with 10% formalin and embedded in paraffin. Lung sections were cut (5 um thick) and stained with hematoxylin/eosin (HE) for optic microscopy examination.

Flow Cytometry.

Cells were preincubated with anti-Fcγ blocking mAb (2.4G2) and washed before staining. Cells were stained with anti-mouse PE-Texas red-conjugated CD45, PeCy5.5-conjugated CD25, Alexa Fluor 700-conjugated CD8 mAb, and Alexa Fluor 750-conjugated CD4 mAb (clone RM4-5). NKT cells were identified using APC-conjugated TCRβ (clone H57-597; eBioscience) and PE-conjugated, PBS57-loaded, CD1d-tetramers (with empty CD1d tetramers always used as control). Tetramers were provided by the NIAID Major Histocompatibility Complex Tetramer Core Facility, Atlanta, Ga. For intracellular staining, after permeabilization (Cytofix/Cytoperm kit; BD Biosciences), cells were incubated with FITC-conjugated IL-4, FITC-conjugated IFN-γ, or the respective isotype control antibodies, FITC-conjugated rat IgG1κ (eBioscience). Cells were analyzed on a BDCanto flow cytometer (BD Biosciences) using FlowJo 8.3.3 software (Tree Star, Inc.).

Adoptive Transfer of NKT Cells.

Figure 9A:
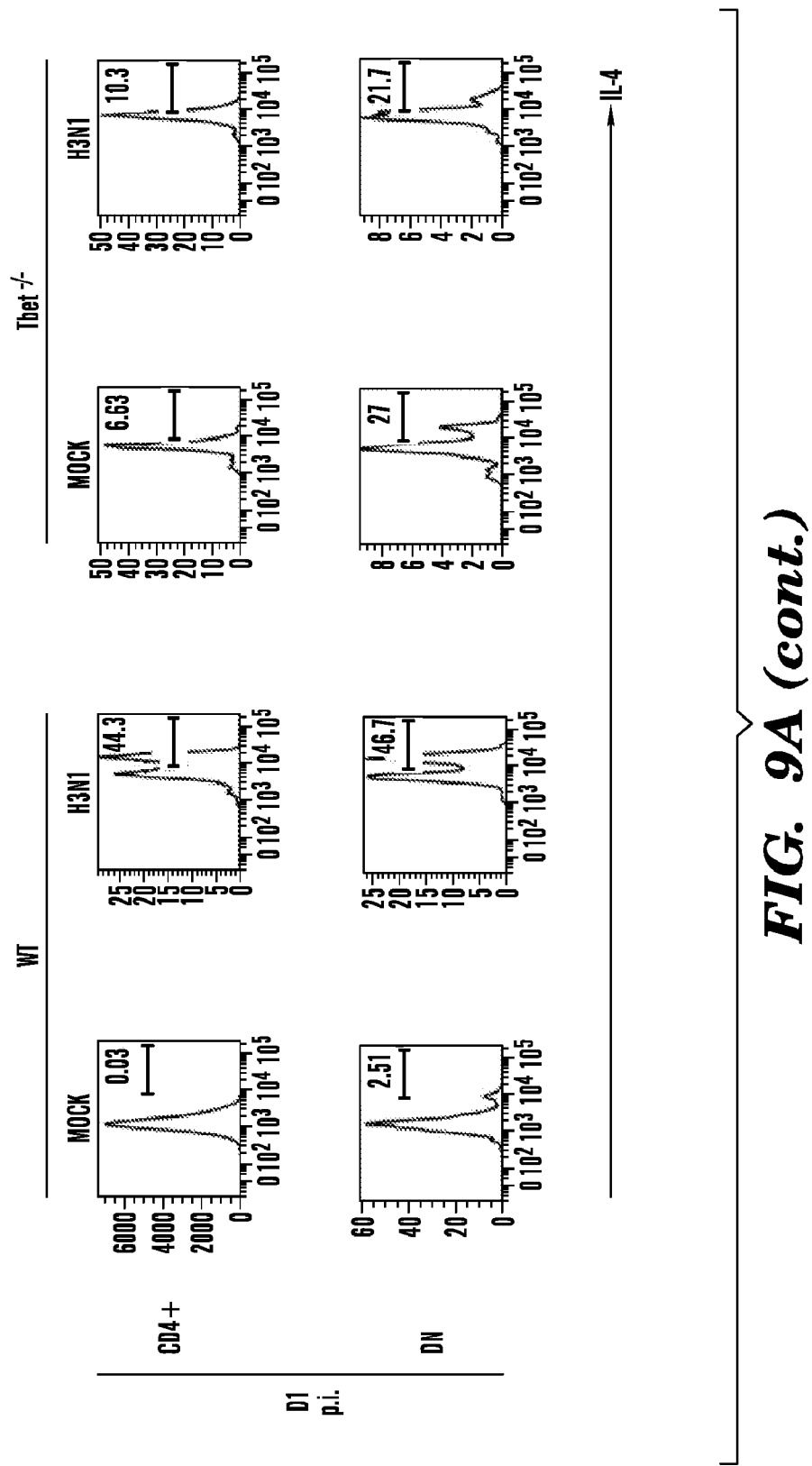
FIGS. 9A-9D show data from 2 wk-old WT, TLR7$^{-/-}$ or T-bet$^{-/-}$ mice that were infected by H3N1 or mock-infected. Lung cells were harvested on day 1, day 14 (9A), or day 42 (9B, 9C, 9D) post-infection.
Figure 9A:
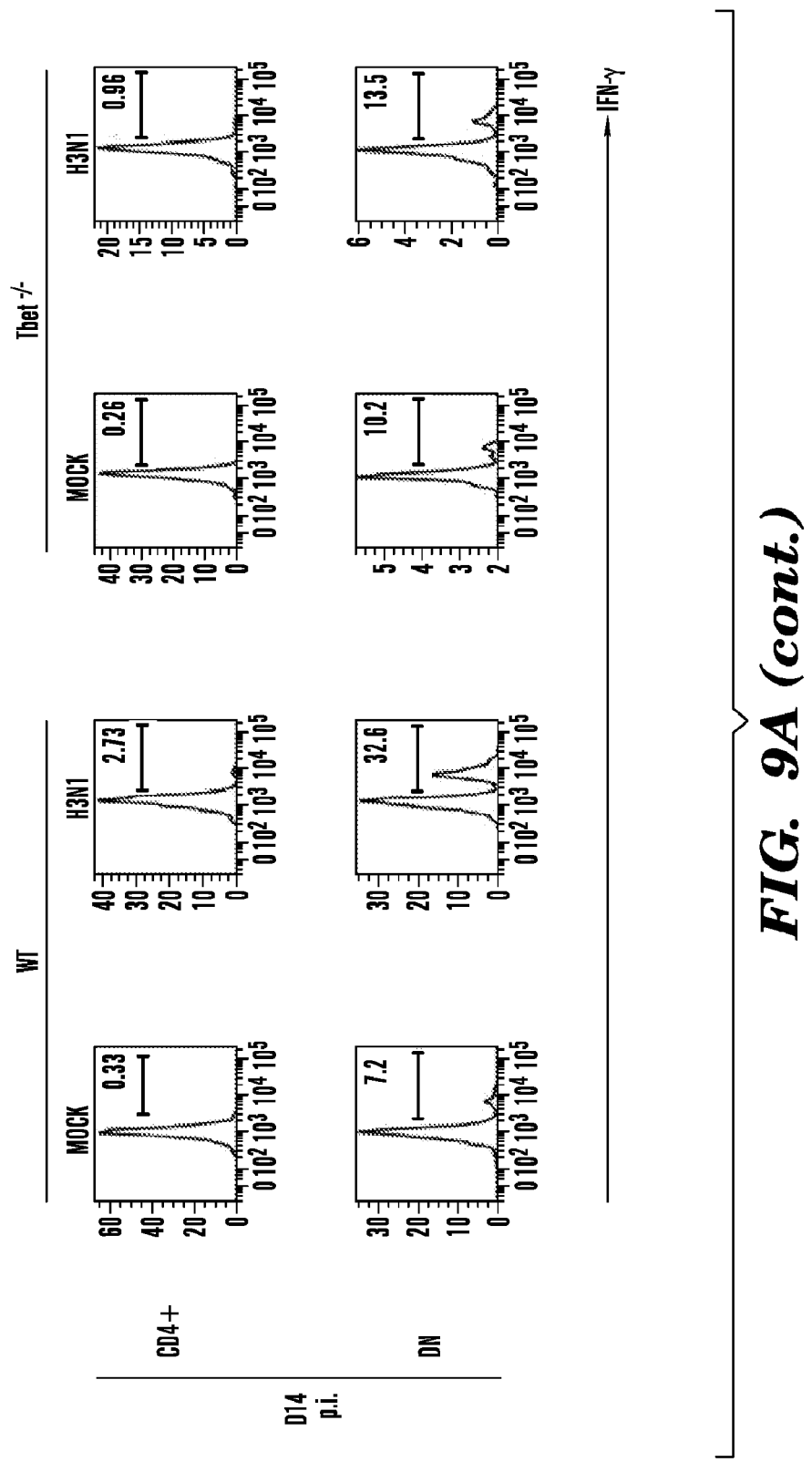
Figure 9A:
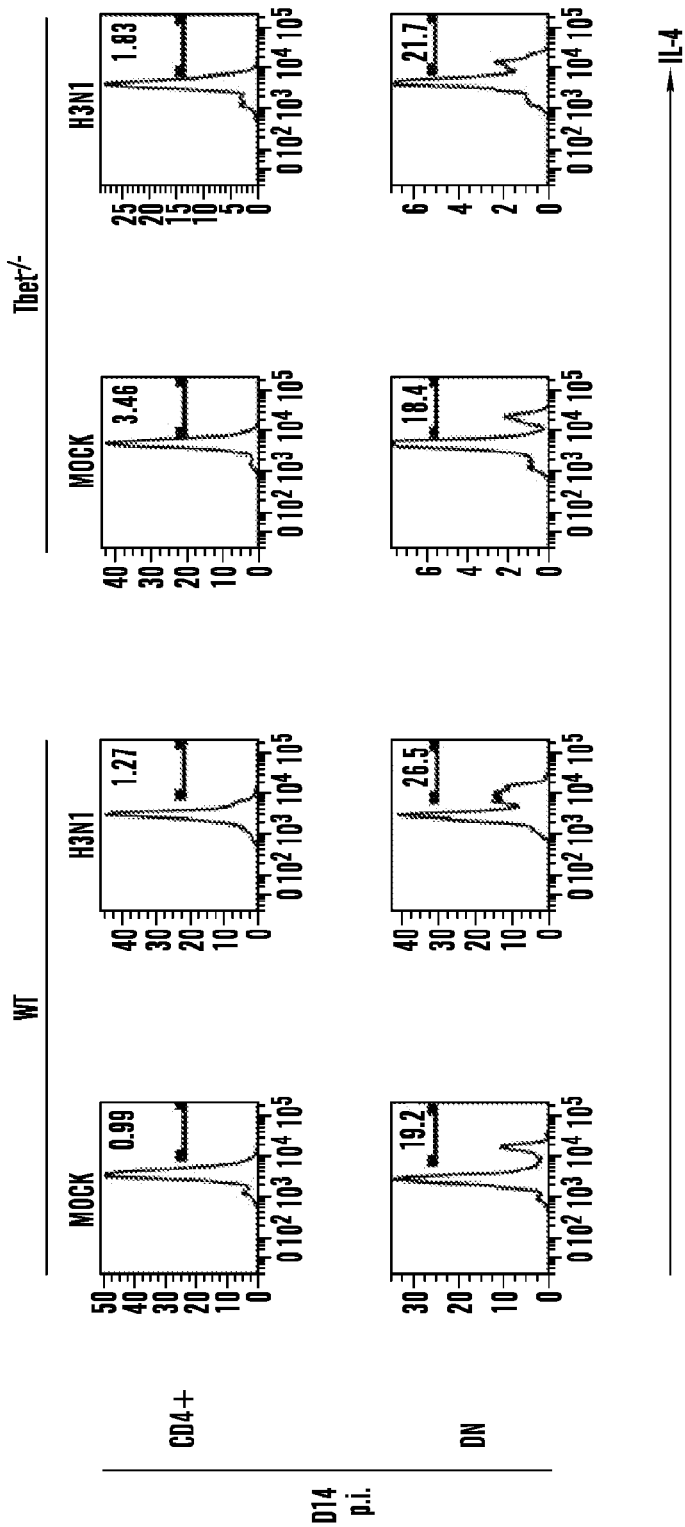
Figure 9C:
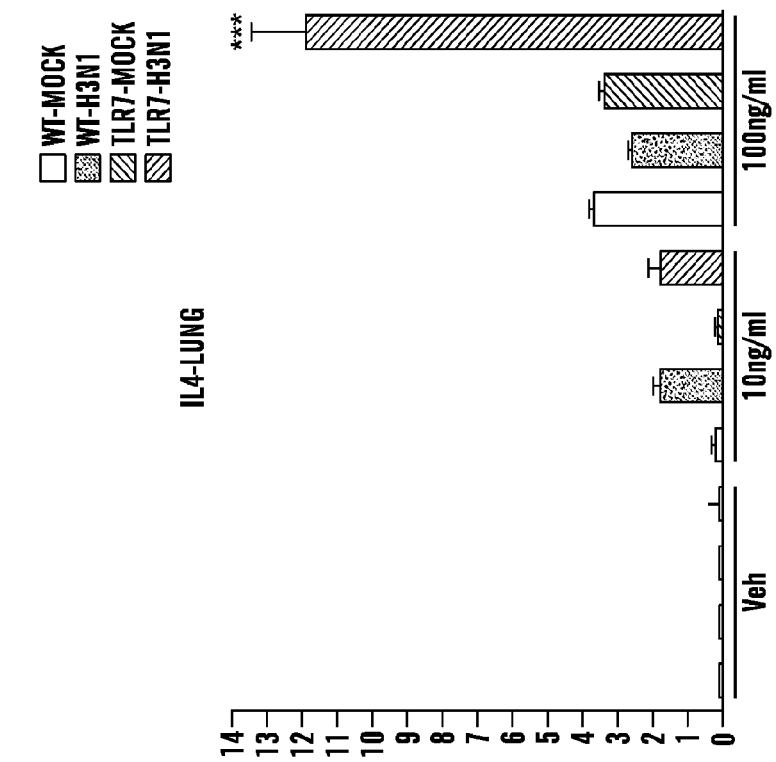
Figure 9B:
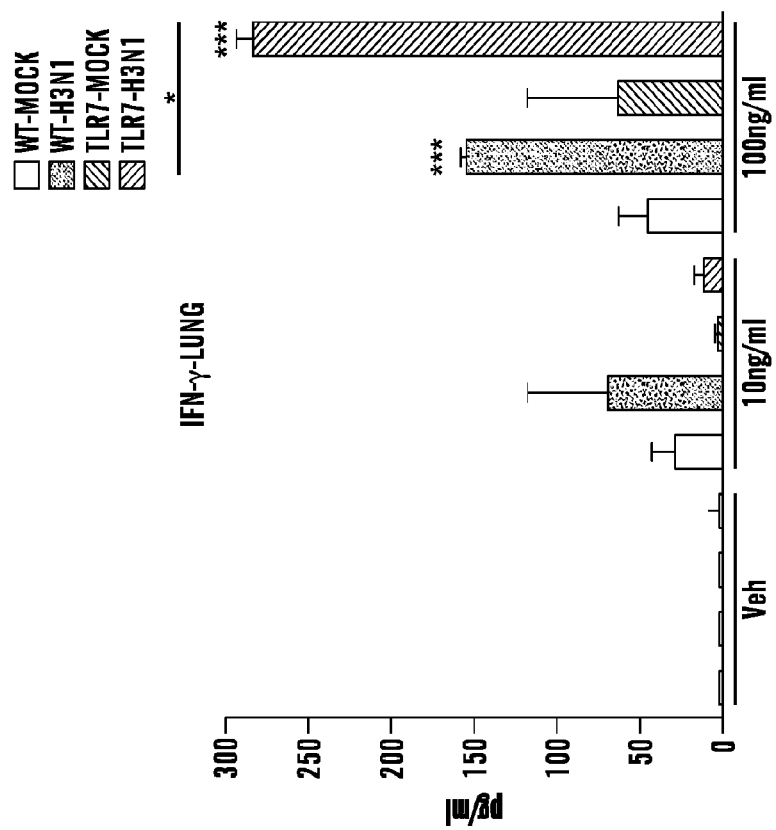

NKT cells were purified from splenocytes of wild-type BALB/c, influenza virus-infected BALB/c, influenza virus-infected TLR7$^{-/-}$, influenza virus-infected Tbet$^{-/-}$, Vα14 TCR transgenic mice, PI57-treated BALB/c, α-GalCer-treated BALB/c mice using magnetic cell sorting (MACS), as previously described (20). Splenic NKT cells were labeled with PE-conjugated CD1d-tetramer, followed by anti-PE microbeads (Miltenyi Biotec), and then sorted with AutoMACS according to the manufacturer's instruction. Purity of NKT cells was approximate 93% (FIG. 9A), and there was no detectable $T_{reg}$ cell contamination (FIG. 9B). Purified NKT cells were adoptively transferred into immunized recipient mice by intravenous injection (106 for Jα18$^{-/-}$; 5×10$^5$ for BALB/c) 1 hr before the first challenge of OVA (day 7). For OVA-specific $T_{Reg}$ cell experiments, 5×10$^4$ DO11.10 CD4$^+$ T cells (from DO11.10 X Rag$^{-/-}$ mice) were adoptively transferred into recipient mice 5 hours before sensitization with OVA/alum (day 0). The recipients later received NKT cells 1 hr before the first challenge of OVA (day 7).

Mouse and Human NKT Cell Lines.

To establish mouse NKT cell lines, NKT cells were purified by a two-step sorting strategy using MACS. Spleen cells from BALB/c or BALB/c Vα14Jα18 Tg mice were depleted of T cells, B cells, granulocytes, macrophages and DCs by AutoMacs, then stained with PE conjugated-CD1d tetramer and FITC conjugated-anti-TCRβ mAb, and sorted using a MoFlo cell sorter (Dako). The purity of the sorted cells was >99%. To propagate the cells, sorted NKT cells were cultured in 96-well flat-bottom plates (1×10$^5$ cells/well) with 5×10$^3$ bone-marrow derived DC in the presence of murine IL-15 (Pepro Tech). Cells were subcultured and restimulated with fresh DCs once a week.

Human NKT cells were isolated from peripheral blood of normal volunteers, using a PE-conjugated anti-human NKT cell antibody (clone 6B11, which recognizes the CDR3 loop of the conserved Vα24 TCR found on iNKT cells) (BD Pharmingen) and anti-PE MACS beads (Miltenyi Biotec). Cells retained on the MACS column were then eluted. CD14$^+$ cells were obtained using anti-CD14 MACS beads and differentiated into dendritic cells (DCs) by culture with GM-CSF (2.5 μg/ml) and rIL-4 (2 μg/ml) for 1 wk. NKT cells and DCs (ratio 10:1) were co-cultured in RPMI 1640 medium containing 10% FCS, 100 U/ml rIL-2 (R&D Systems) and 1 ng/ml rIL-15 (Peprotech).

Mouse NKT Cell Hybridomas.

NKT cell hybridomas were established from C57BL/6 thymic NKT cells by fusion with thymoma BW5147 as previously described (61).

Stimulation of Invariant Vα14 NKT Cell Hybridomas with Glycolipids Coupled with Immobilized CD1/β2m Proteins.

Culture wells were coated with recombinant CD1/β2m dimer proteins (Becton Dickinson) according to the manufacture's protocols. Cholesteryl glycosides dissolved in DMEM were added to the well, incubated for 1 day at 4 C, and then washed with DMEM. Hybridomas derived from invariant Vα14 NKT cells and an irrelevant Vα8+ T cell as a control (61) were cultured for 1 day in the wells. Cytokines in the culture supernatants were determined by ELISA.

Human NKT Cell Clone.

CD1d transfected K562 cells and CD1d restricted human NKT cell clone BM2a.3 were previously described (62). The anti-CD1d antibody (clone 12.1.1.1) experiments have been performed as described (63).

In Vitro Culture of Human NKT Cell Clone with CD1d Coated Plates.

Maxisorp plates (Nunc) were coated with PBS diluted recombinant human CD1d/β2 microglobulin Fc fusion proteins (0.5 μg/well; kindly provided by Dr. Jenny Gumperz (64) and anti-LFA-1 antibodies (0.05 μg/well, AbD Serotec) overnight at 4° C. After washing with PBS, immobilized CD1d was loaded with sonicated lipid antigens diluted in 25% DMSO/dH2O by overnight incubation at 37° C. After washing with PBS and culture media, NKT cells were added (5×104 cells/well) and culture supernatants were analyzed for IFN-γ by ELISA after overnight culture at 37° C.

Helicobacter pylori.

Bacterial strains and growth conditions: Helicobacter pylori SS1 mouse strain and as described earlier isolate 17B/RH of human H. pylori S form strain (65) were grown on solid agar plates with 7% horse blood, at 37° C. under microaerobic conditions (5% O2, 10% CO2 and 85% N2).

Knockout of Hp0421 Glucosyltransferase.

Hp0421 was first amplified by PCR from H. pylori genomic DNA using the primers Hp0421-F (5'-ATG GTT ATT GTT TTA GTC GTG-3') and Hp0421-R (5'-TTA TGA TAA GGT TTT AAA GAG-3'), and the PCR product was subsequently cloned into SmaI-digested pUC19. The resultant plasmid was then linearised using a unique BglII site in the Hp0421 sequence, and BamH1-cut Cm-resistance cassette was cloned into this BglII site. The pUC18 cloned Hp0421 gene was thus disrupted at by position 809 by the CmR cassette. The resultant allelic exchange plasmid pUC18-Hp0421::CmR was then introduced into H. pylori by natural transformation. H. pylori were inoculated on an agar plate on areas of 10-15 mm in diameter, and incubated for 7 hours, 37° C., microaerobic. Aliquots of plasmid pUC19 with insert Hp0421::CmR were spotted directly onto the inoculated agar, (0.7 μg in 7 μl), and incubation was continued overnight. The bacteria were harvested in 1 ml PBS, pelleted and resuspended in 100 μl PBS and were spread on blood agar plate with chlooramphenicol 25 g/ml to select transformants. After incubation for 5 days, single colonies were taken and grown up. Disruptants were confirmed by PCR using the primers F (5'-GAGGGAATGATA-GAAATTG-3') and R (5'-TCCCATAATCATGGACTTC-3'); bonafide mutants yielded a band of size 1.8 kb, 1.1 kb expected from the wild type strain. More details of experiments can be found in paper (66).

ELISA.

Mouse or human IL-4 and IFN-γ levels were measured by ELISA, as previously described (20). Mean values of triplicate cultures were shown. Data are representative of two or three independent experiments.

Statistical Tests.

Differences between groups with parametric distributions were analyzed by Student's 2-tailed t test; otherwise, the Mann-Whitney U test was used. Data represent mean±SEM. P values of 0.05 or less were considered statistically significant.

Introduction

As described herein, we show that influenza A virus infection in suckling mice protected the mice as adults against allergen-induced airway hyperreactivity (AHR), a cardinal feature of asthma. The protective effect was associated with the preferential expansion of CD4$^-$CD8$^-$, but not CD4$^+$, natural killer T (NKT) cells, and required T-bet and TLR7. Adoptive transfer of this population into allergen-sensitized adult mice suppressed the development of allergen-induced AHR, while expanding allergen-specific Foxp3+ TReg cells. The influenza-induced protective effect could be mimicked by treatment of suckling mice with a glycolipid, derived from *Helicobacter pylori* (a bacterium associated with protection against asthma), and which activated NKT cells in a CD1d-restricted fashion. These findings provide novel regulatory pathways and new therapeutic strategies for asthma and other inflammatory conditions.

Bronchial asthma, a complex and heterogeneous trait, is a major public health problem, affecting nearly 10% of the general population, and disproportionately affecting children. Moreover, the prevalence of asthma has increased dramatically over the past three decades, an increase believed to be due to changes in our environment. These environmental changes include reductions in the incidence of infectious diseases that may exert protective effects against asthma, as suggested by the Hygiene Hypothesis (1). While the infectious agents responsible for this relationship, and the precise mechanisms by which infectious microorganisms might protect against asthma are very poorly understood, epidemiological studies suggest that infection with bacteria (e.g., *Helicobacter pylori* (2, 3), endotoxin (4), or *Acinetobacter lwoffii* (5)) or viruses (e.g., hepatitis A virus (6, 7)) may reduce the likelihood of developing asthma.

The role of viral infection in modulating the development of asthma is particularly complex, because many different viruses affect the respiratory tract, some appearing to enhance and some appearing to protect against the development of asthma. For example, infection with human rhinovirus in children before three years of age increases the later risk of developing asthma (8), while other respiratory viral infections have been shown to protect against the later development of asthma (9-14). However, in older individuals with established asthma, respiratory viral infection, particularly with influenza A virus, almost always triggers acute symptoms of asthma (15-17). These discrepancies may be due to the timing of the infection, since infection in very young children could profoundly alter the developing innate immune system in such a way as to protect against the later development of asthma, or to the specific immunological cell types activated by a given infectious agent, as described for the first time herein.

To improve our understanding of the role of respiratory viral infection in children in the development of asthma, we studied a mouse model of asthma, in which suckling mice were infected with the influenza A virus (H3N1), and were subsequently studied as adults for susceptibility to allergen-induced AHR, a cardinal feature of asthma. As described herein, we found that H3N1 infection in suckling mice protected the mice as adults against allergen-induced AHR. The protective effect was associated with the preferential expansion of a subpopulation of suppressive DN NKT cells, and can be mimicked by treatment of suckling mice with several specific glycolipids, including one derived from *H. pylori*, as shown herein.

Infection of Suckling Mice with H3N1 Protects Against AHR.

Figure 1B:
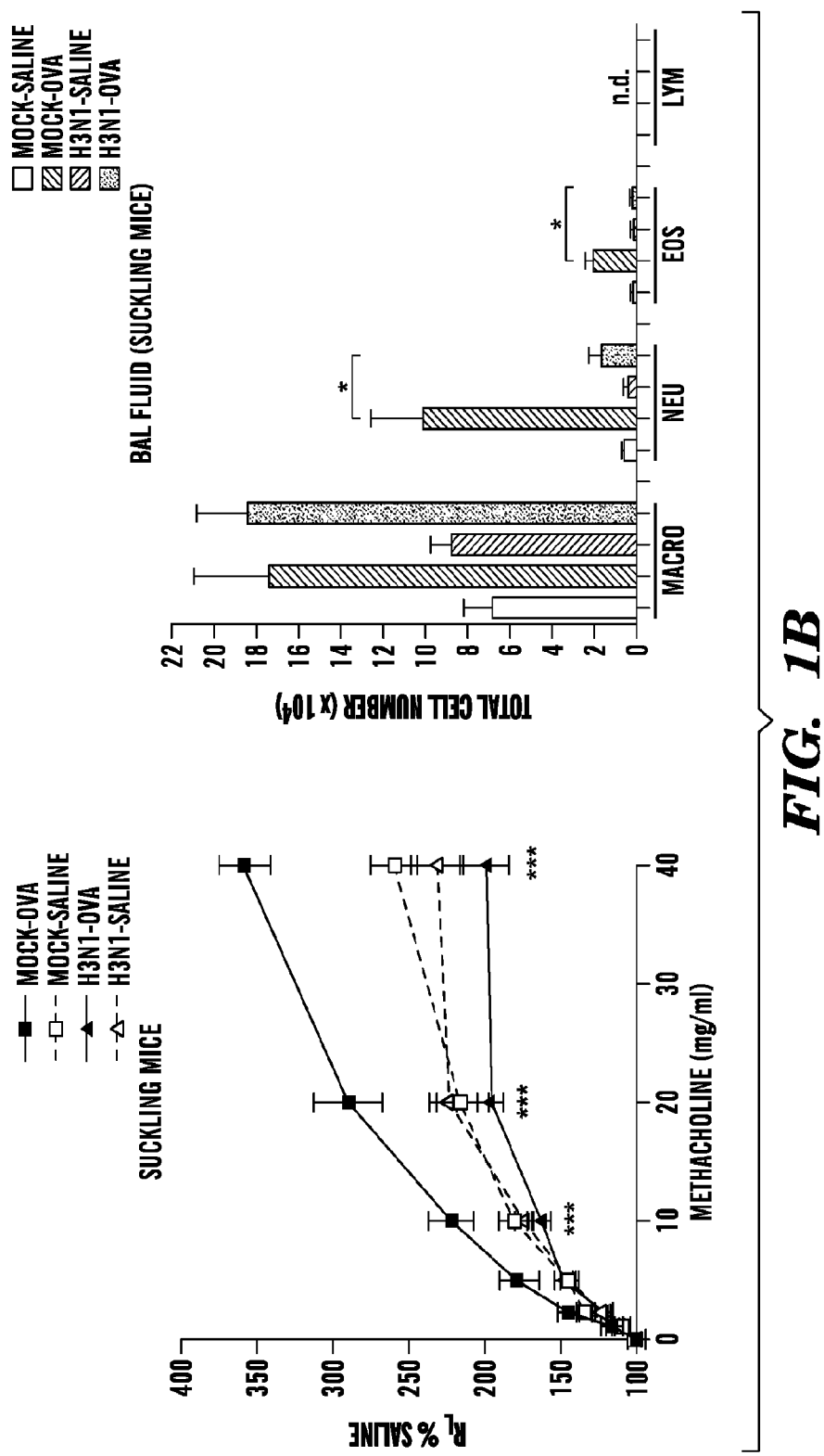
Figure 1C:
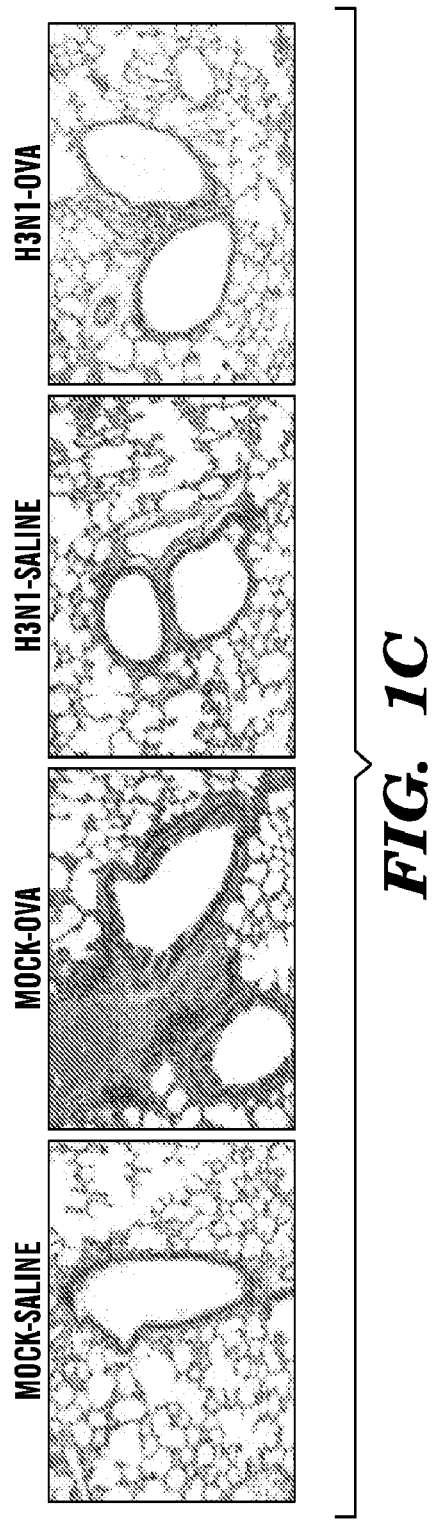
Figure 1D:
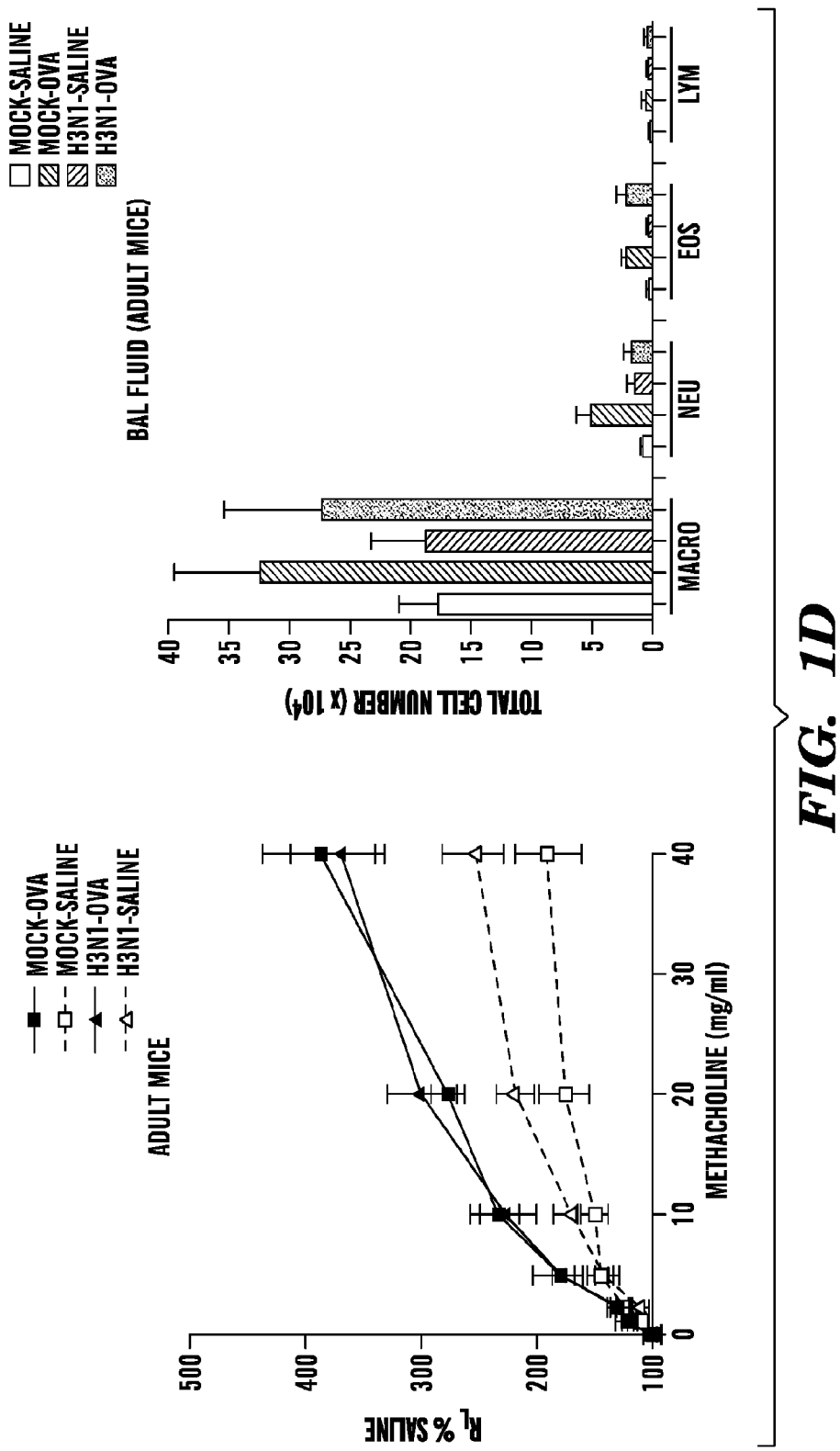

We infected suckling (2 week old pups) or adult (8 week old) mice with the Influenza A/Mem71 (H3N1) virus; 6 weeks later the mice were examined for susceptibility to ovalbumin (OVA)-induced AHR (FIG. 1A). H3N1 infection in 2 wk old mice protected the mice as adults (at 8 wks of age) against OVA-induced AHR (FIG. 1B) and airway inflammation (FIGS. 1B and 1C). In contrast, in the mock-infected mice, at 8 wks of age, severe OVA-induced AHR and airway inflammation developed. Whereas infection in 2 wk-old suckling mice conferred protection, infection in 8 wk-old adult mice with H3N1 did not protect against subsequent OVA-induced AHR or airway inflammation (FIG. 1D).

Figure 2A:
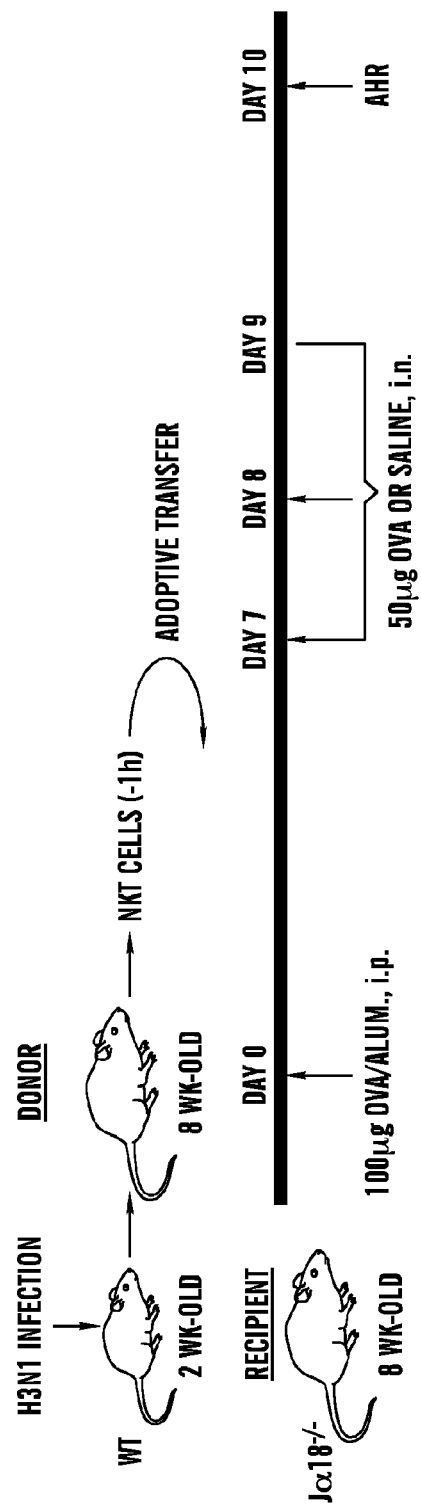
FIGS. 2A-2D demonstrate that adoptive transfer of H3N1-exposed NKT cells fails to reconstitute OVA-induced AHR.
Figure 2B:
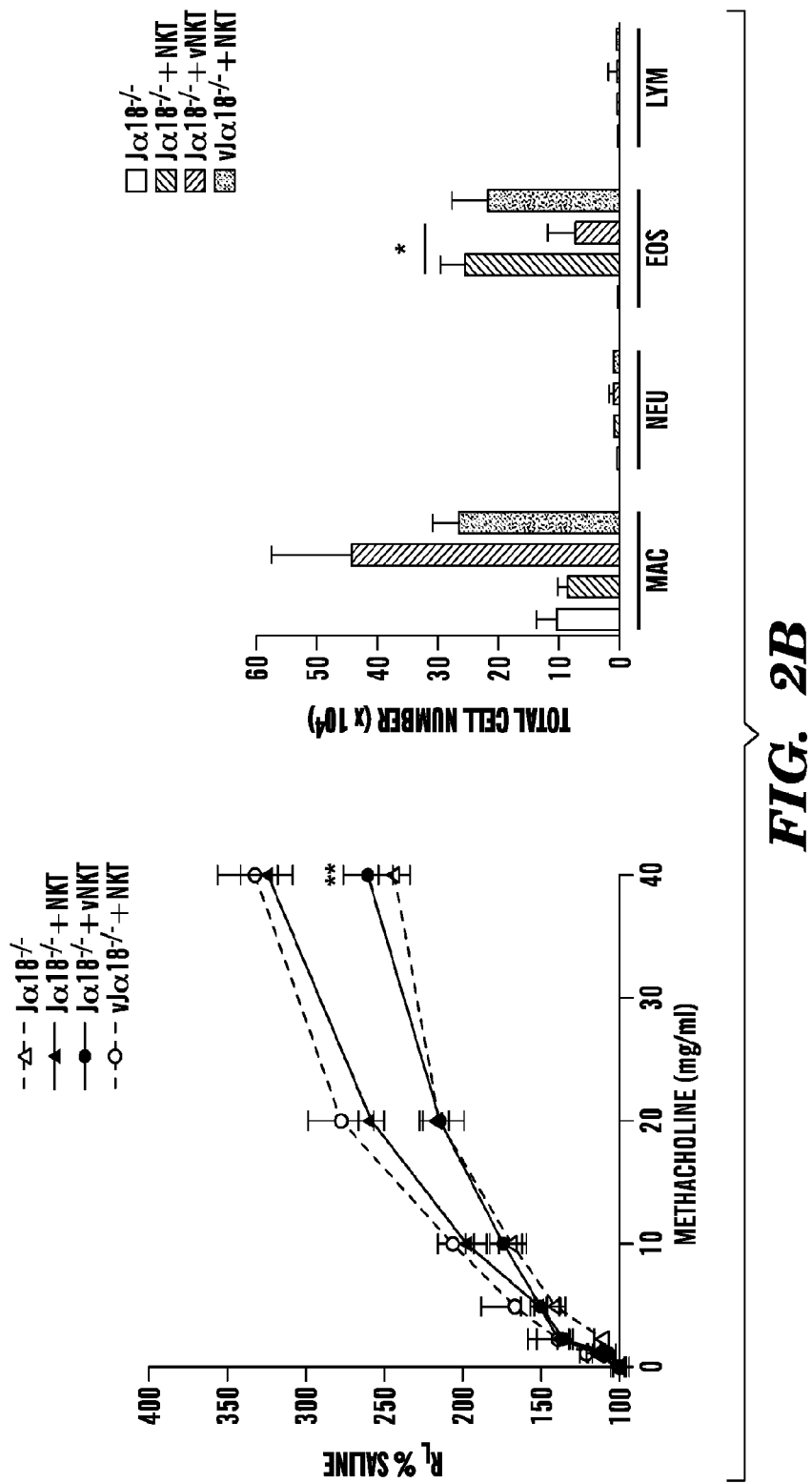
Figure 2C:
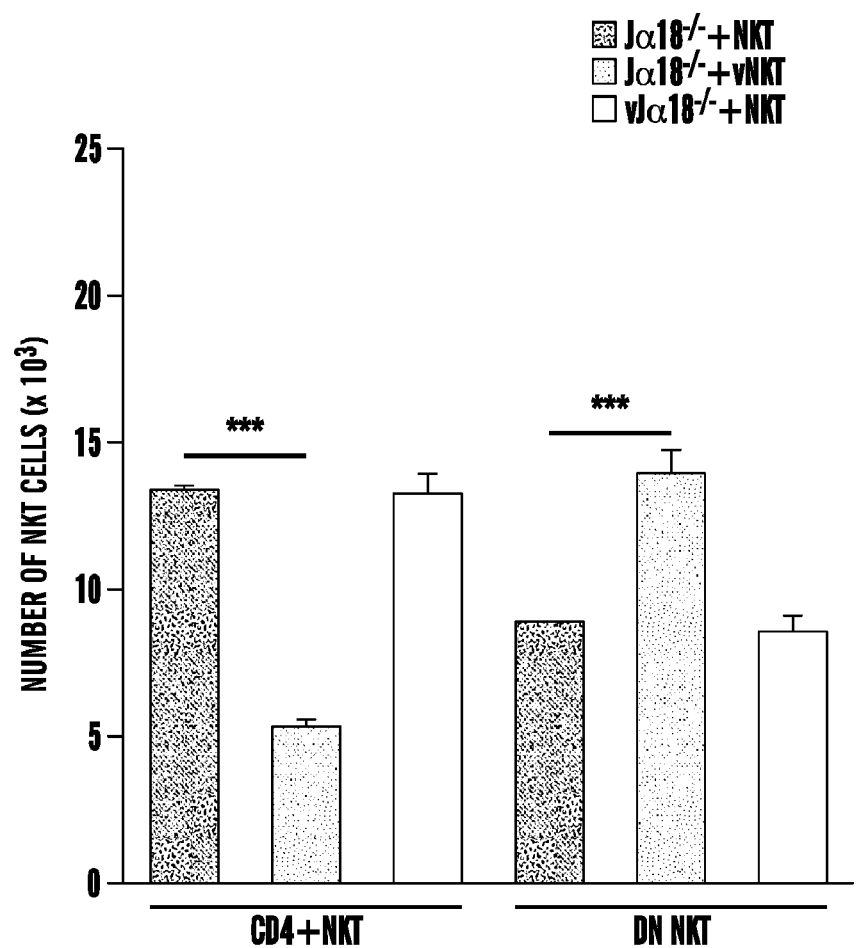
Figure 2D:
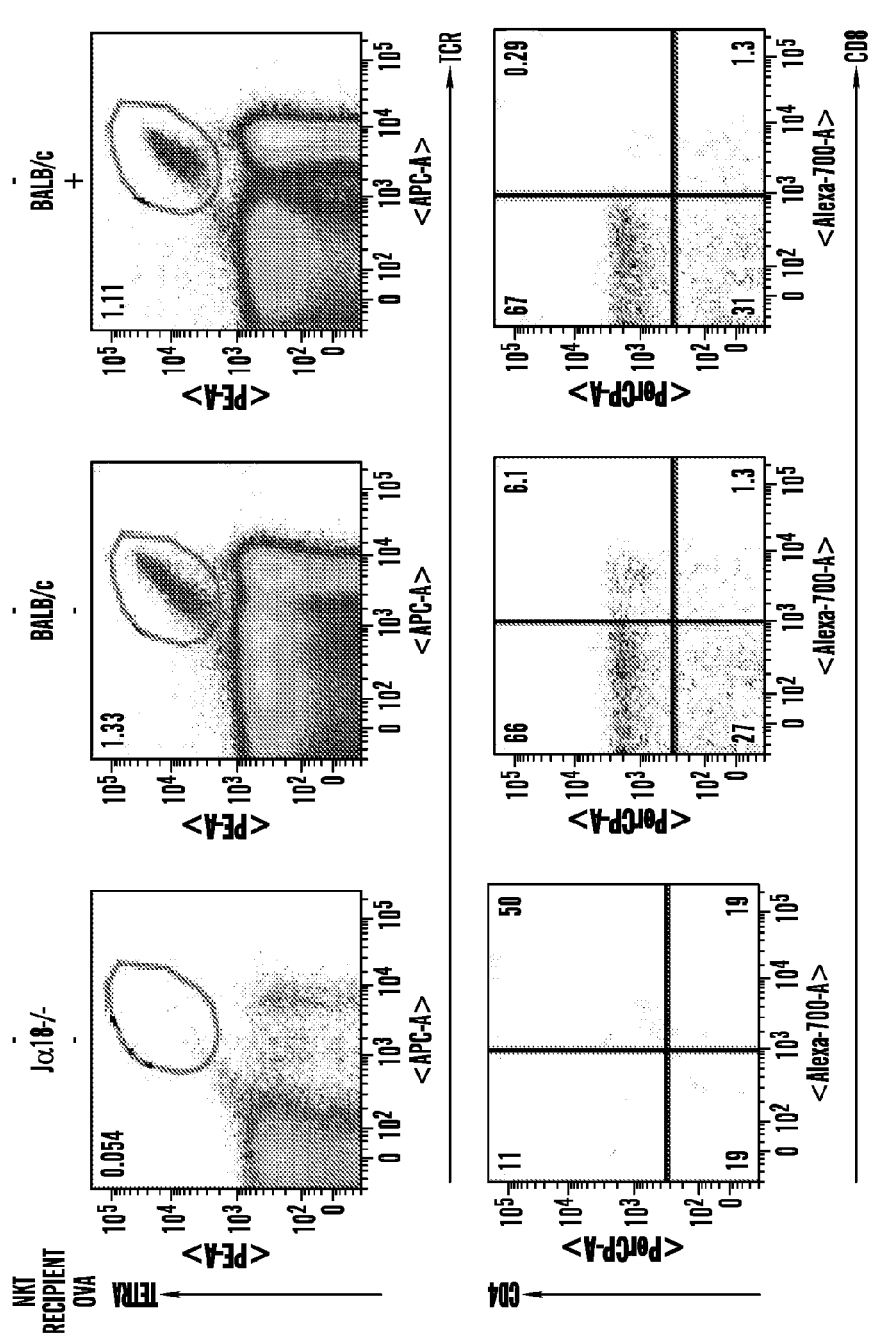
Figure 2D:
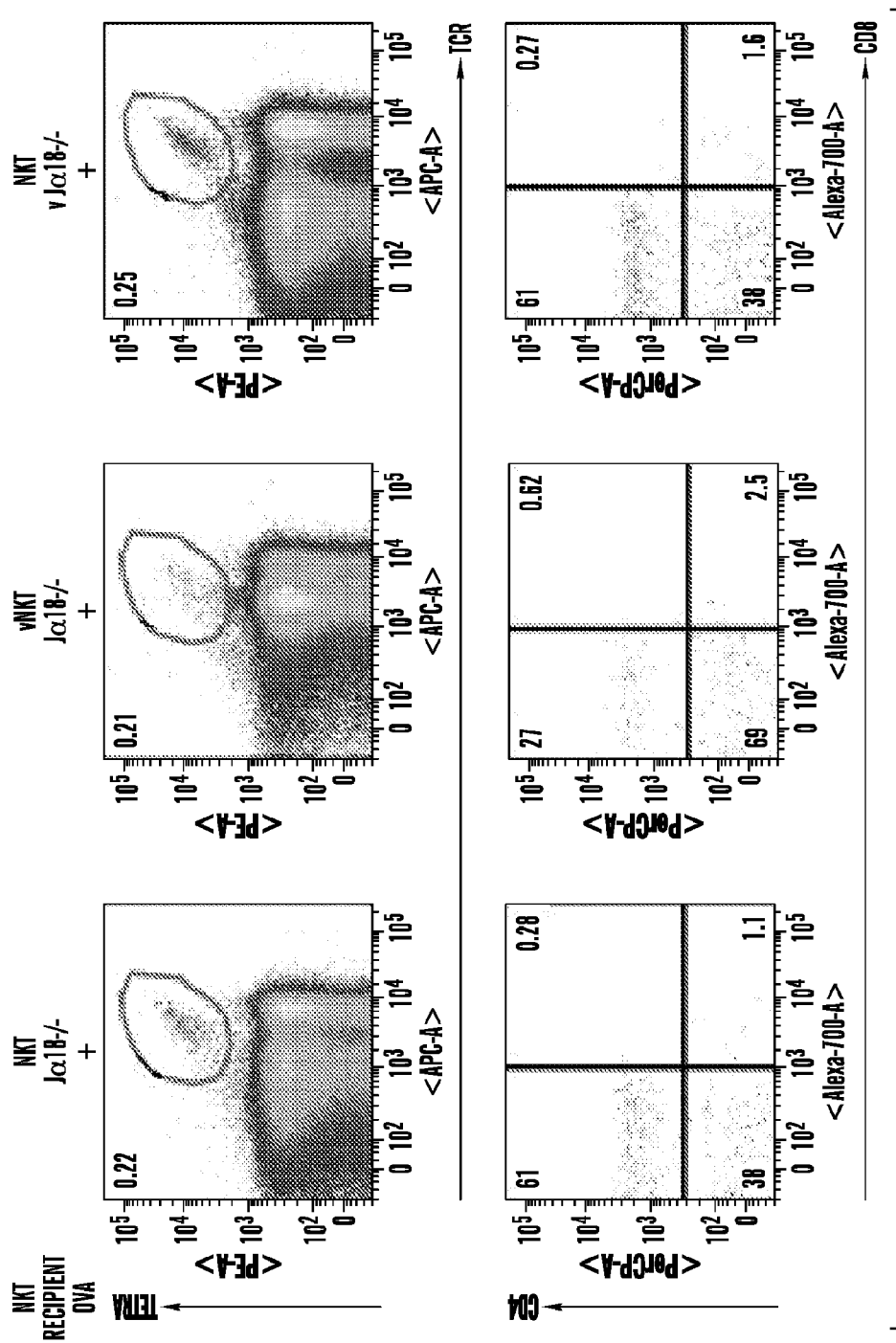
Figure 8A:
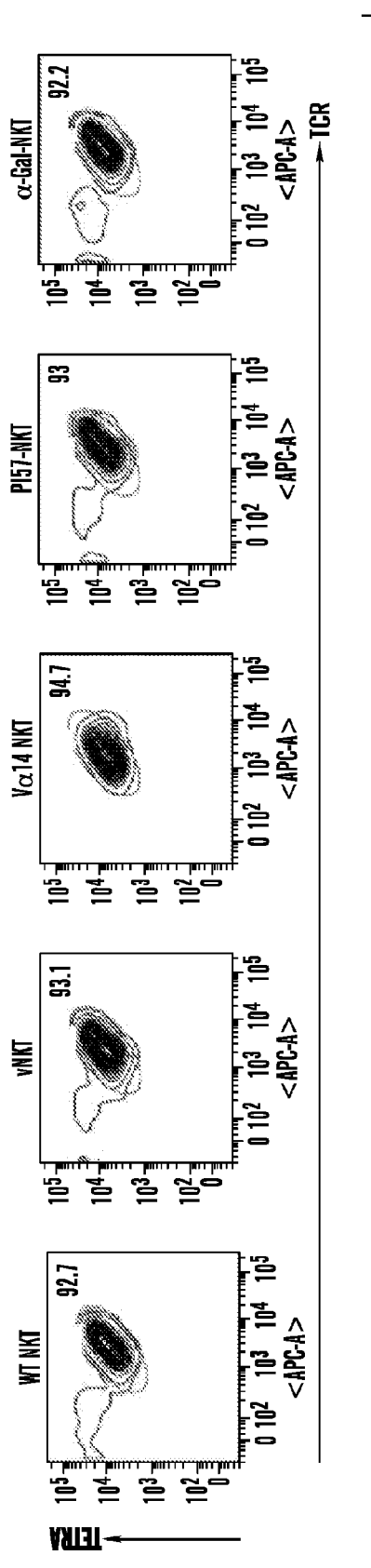
FIGS. 8A-8C demonstrate purity of transferred NKT cells.

Adoptive Transfer of NKT Cells Cannot Reconstitute OVA-Induced AHR in Jα18$^{-/-}$ Mice Infection with a different influenza virus strain (H3N2) enhanced the ability of respiratory tolerance to prevent OVA-induced AHR (11), consistent with the idea that influenza infection is complex and can affect multiple compartments of the immune system. Because infection with influenza A virus has been shown to directly activate NKT cells (18), which play a very important role in asthma (19), we next determined whether infection with the H3N1 virus affected the function of NKT cells. We therefore purified NKT cells from mice infected with H3N1 as sucklings (42 days after infection), and adoptively transferred these cells (92-97% purity, FIG. 8A) into adult, OVA-sensitized, NKT cell-deficient recipients (Jα18$^{-/-}$ mice) (FIG. 2A). After receiving the H3N1-exposed NKT cells, the Jα18$^{-/-}$ mice, which have CD1d restricted non-invariant- but not invariant-TCR NKT cells, and which cannot develop allergen-induced AHR unless reconstituted with functional invariant-TCR NKT cells (20-22), failed to develop OVA-induced AHR (FIG. 2B). In contrast, transfer of NKT cells from mock-infected mice to Jα18$^{-/-}$ mice fully reconstituted AHR. Moreover, H3N1 infection in 2 wk old Jα18$^{-/-}$ suckling mice (vJα18$^{-/-}$ mice) and later reconstitution (at 8 wks of age) with NKT cells from mock-infected mice did not prevent OVA-induced AHR (FIG. 2B), indicating that early exposure of all of the non-NKT cells in Jα18$^{-/-}$ (e.g., conventional CD4+ and CD8+ T cells) to H3N1 was not effective in preventing AHR. Finally, in the lungs of mice receiving the H3N1 virus-exposed NKT cells (42 days after infection), significantly greater CD4$^-$CD8$^-$ (DN), and significantly fewer CD4$^+$, NKT cells were present (FIGS. 2C and 2D), indicating that H3N1 infection of 2 wk old suckling mice reduced the inflammatory function of the NKT cells, possibly by altering the CD4$^+$ versus DN NKT cell subset proportions.

Figure 3A:
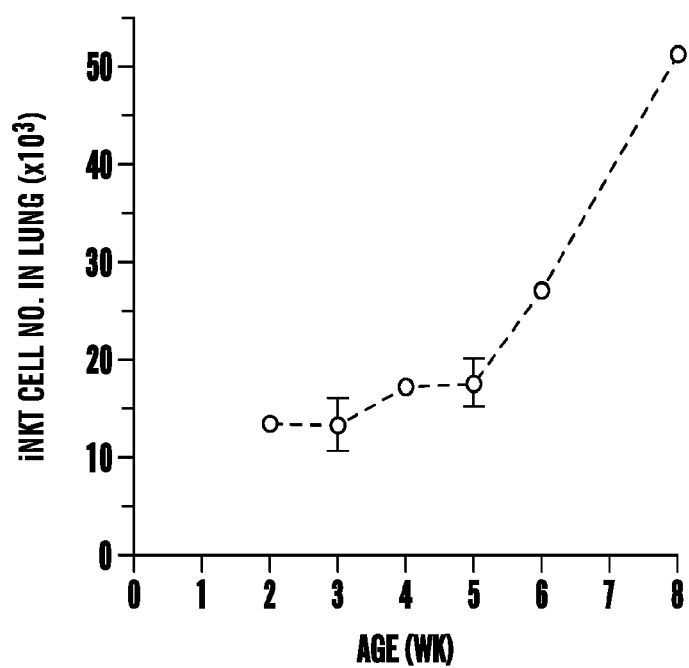
Figure 3A:
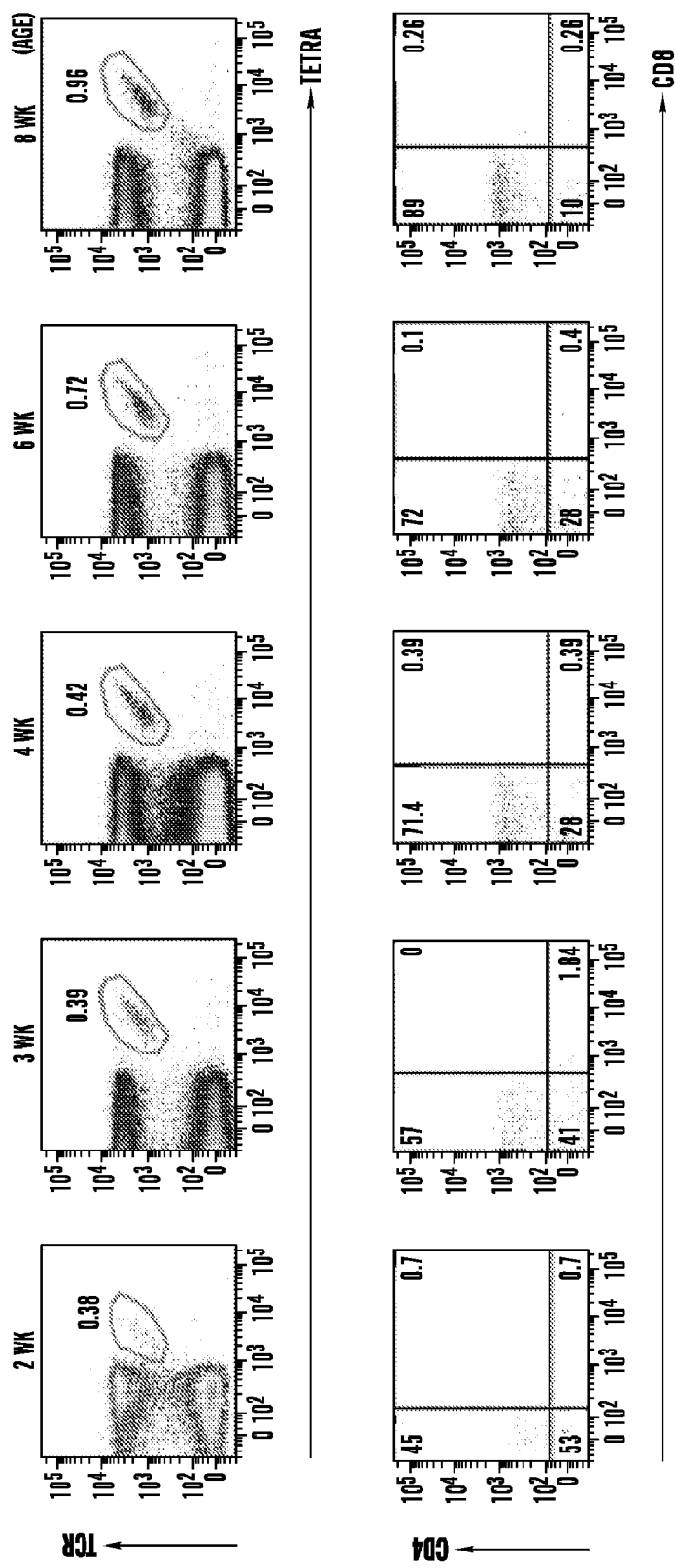
Figure 3B:
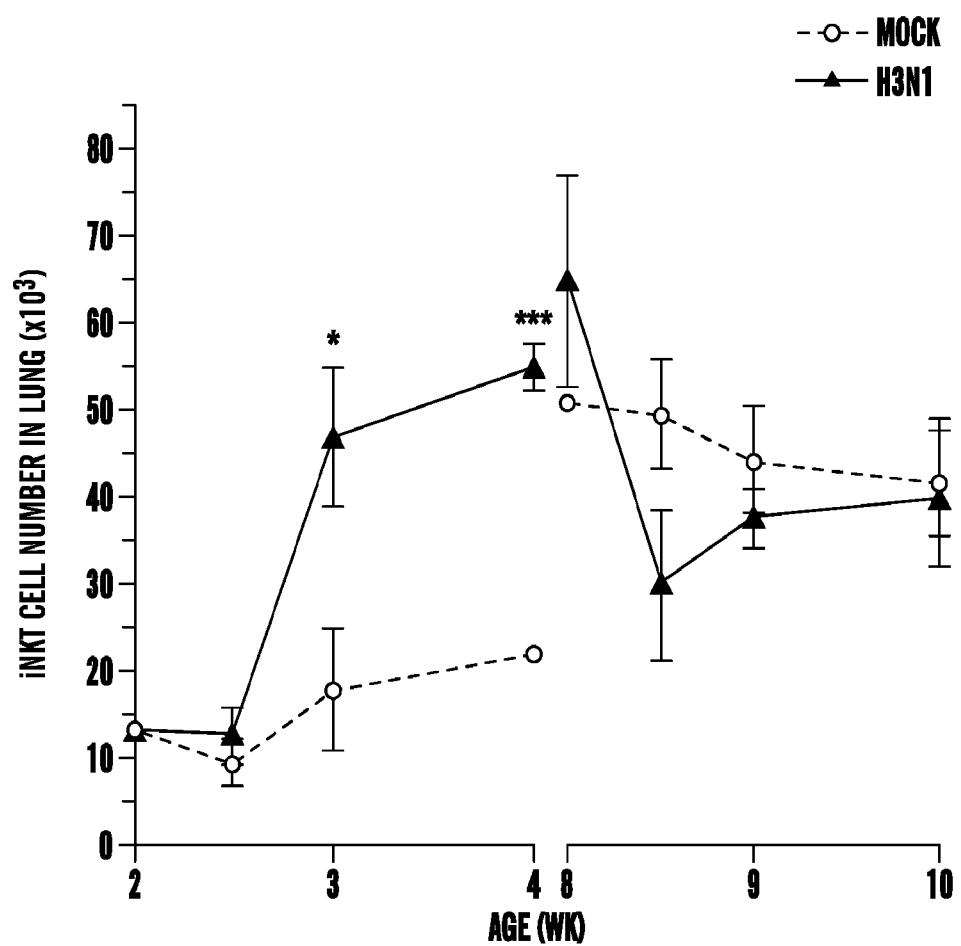
Figure 3B:
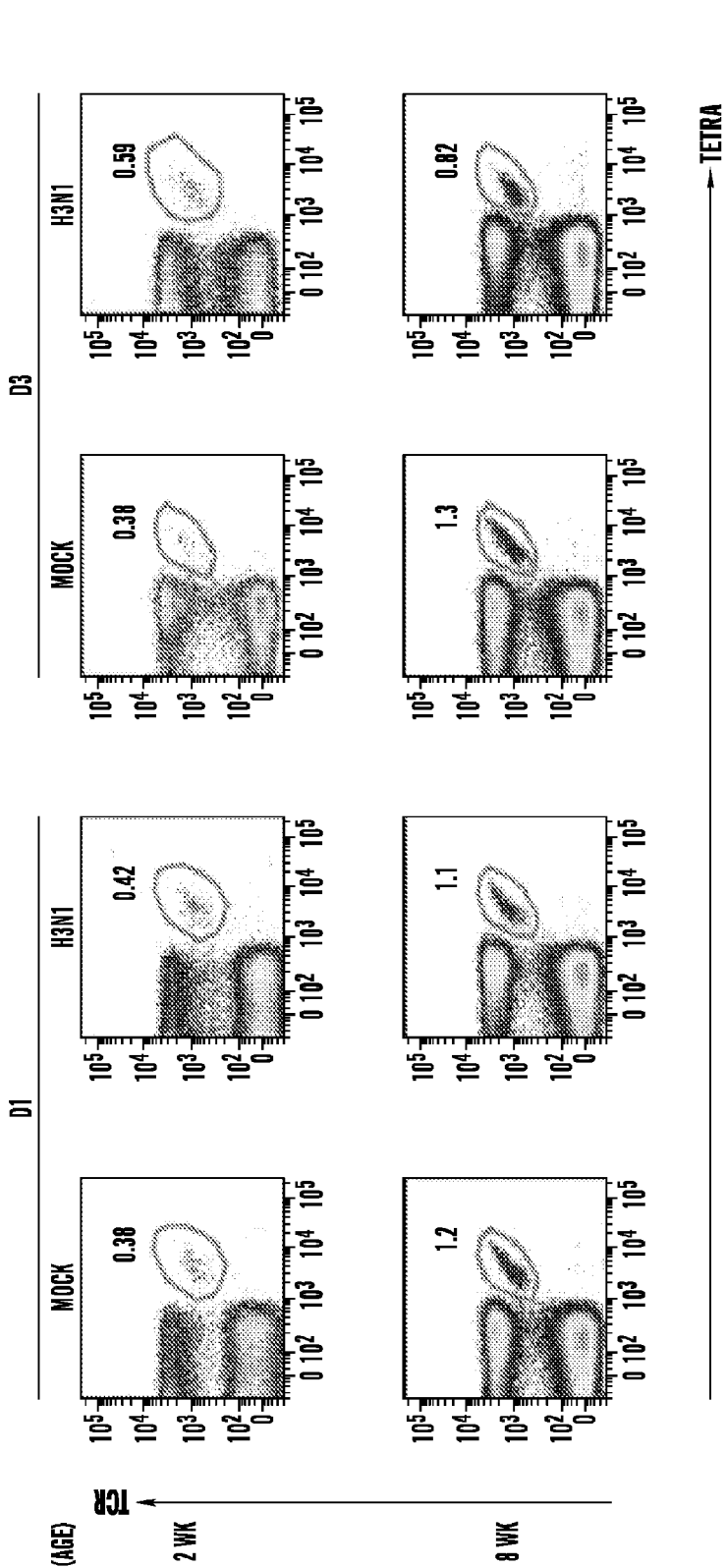
Figure 3B:
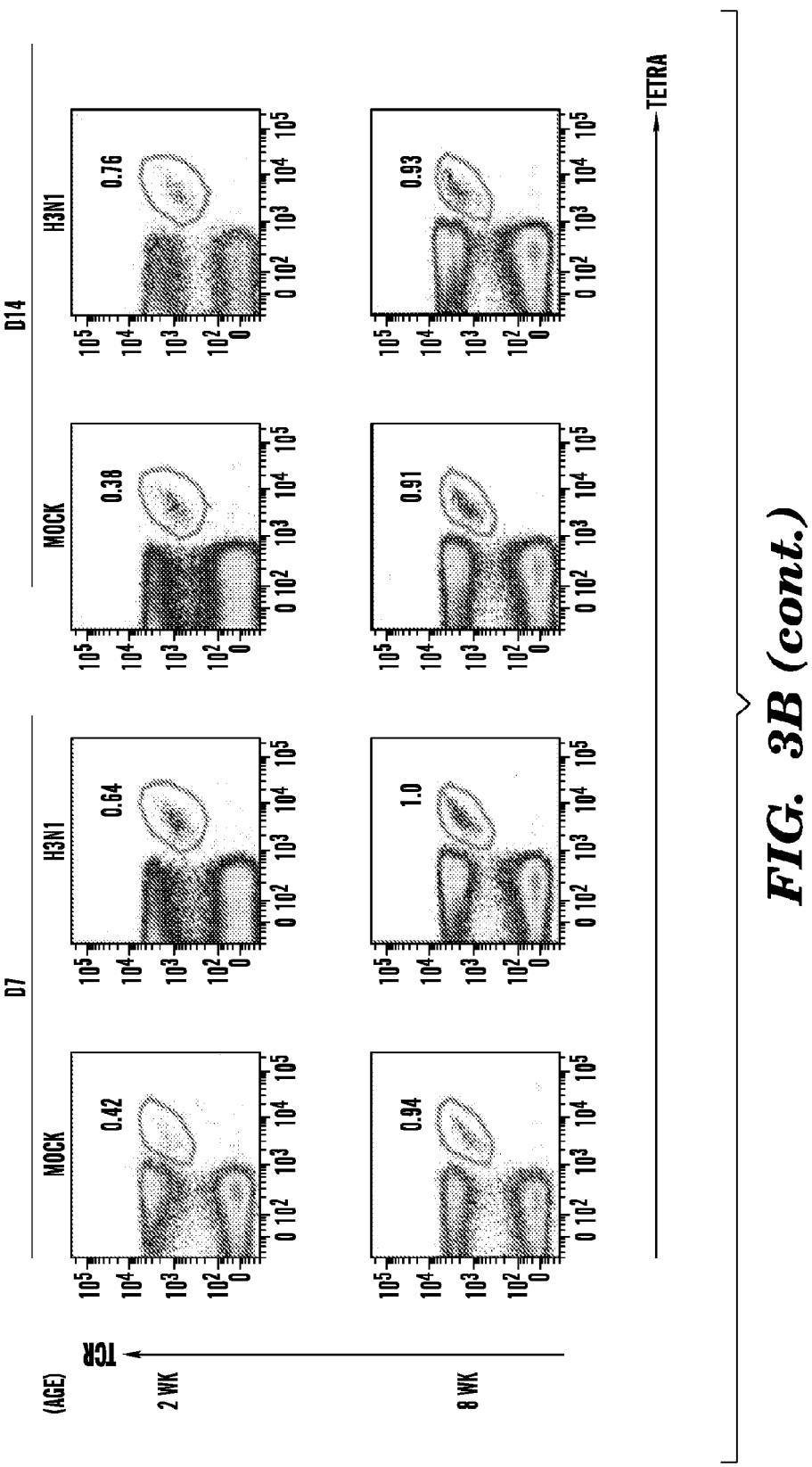

H3N1 Infection Accelerates the Expansion of Pulmonary NKT Cells in Suckling Mice In two-week-old naïve suckling mice, few NKT cells are present in the lungs, although this number increases normally to adult levels over a six-week period of time (FIG. 3A). Importantly, H3N1-infection, but not mock-infection, in suckling mice greatly accelerated the expansion of the pulmonary NKT cell number (FIG. 3B). In contrast, H3N1-infection in adult mice had little effect on pulmonary NKT cell numbers. In fact, H3N1 infection in the adult mice transiently reduced the number of NKT cells, possibly due to activation-induced TCR down-regulation (FIG. 3B). In 2 wk old suckling naïve mice, approximately 50% of the pulmonary NKT cells were CD4$^+$, and over time this fraction increased such that in 8 wk-old adult naïve mice, 89% of the pulmonary NKT cells were CD4$^+$ (FIG. 3A, dot plots).

Figure 3C:
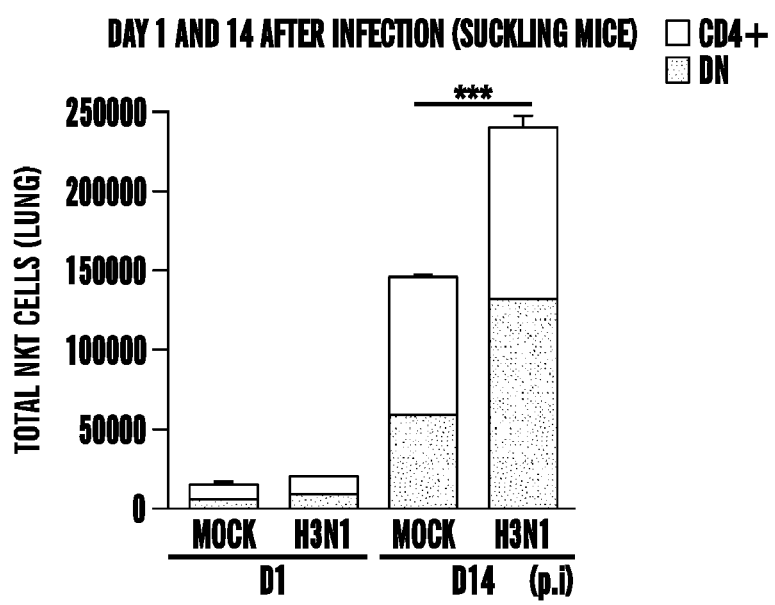
Figure 3D:
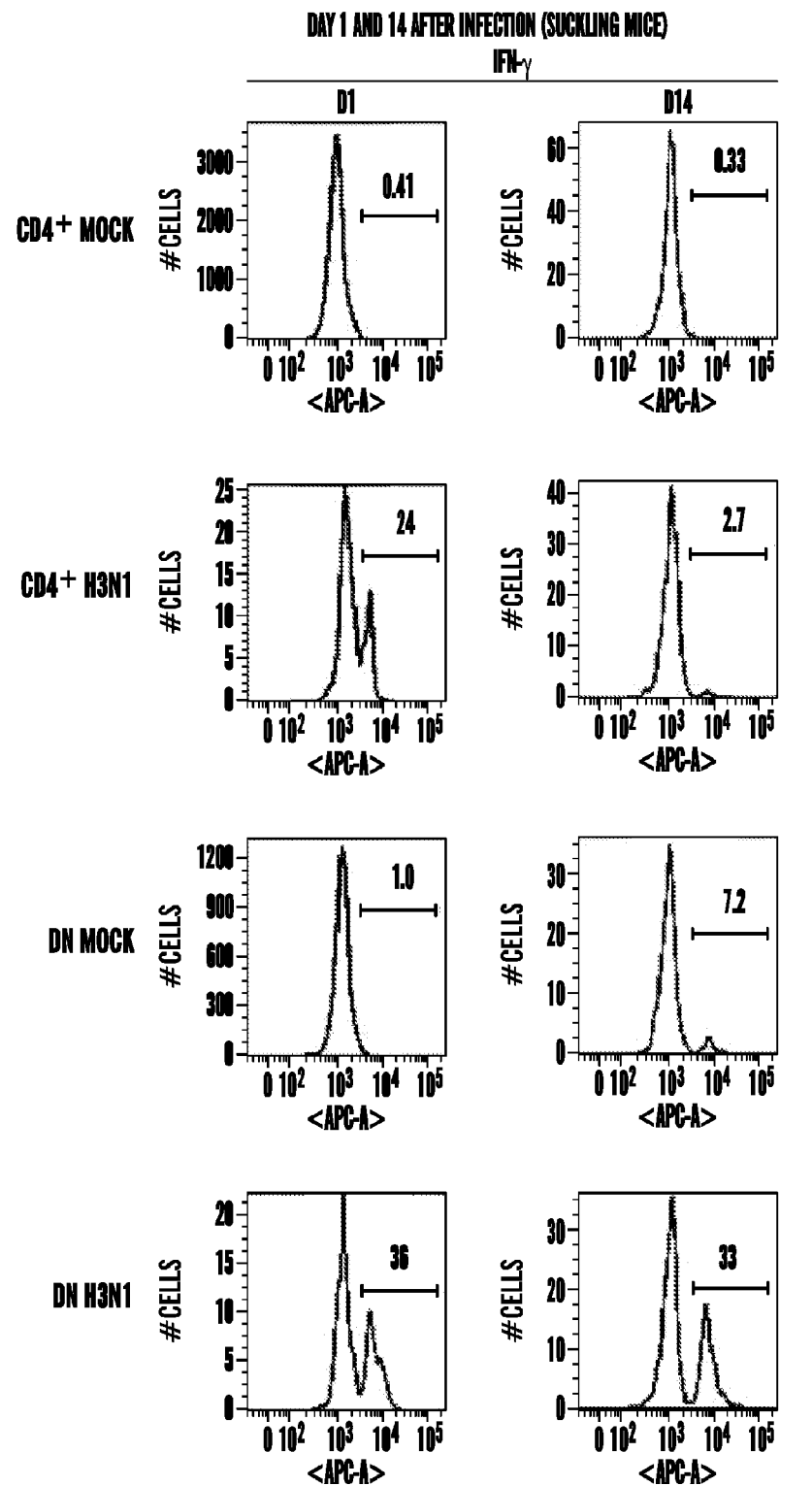
Figure 3D:
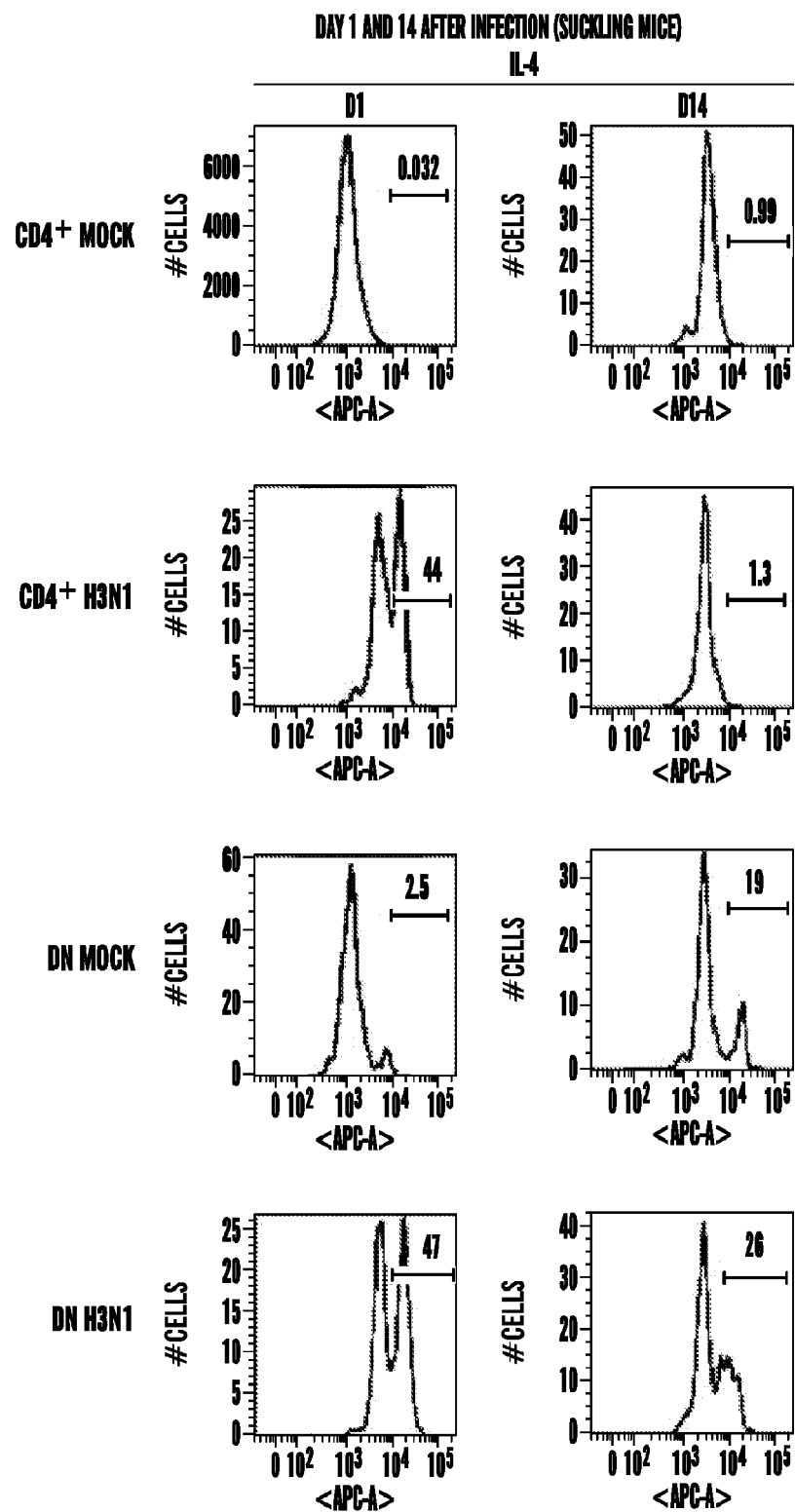

However, H3N1 infection of suckling mice preferentially increased the number of DN NKT cells by day 14 post infection (FIG. 3C). Both CD4+ and DN NKT cells from the suckling mice secreted IFN-γ on day 1 of infection, but 14 days post-infection only DN but not CD4+ pulmonary NKT cells continued to secrete IFN-γ (and IL-4), as assessed with intracellular staining without in vitro restimulation (FIG. 3D). Thus, 14 days post-infection the great majority of cytokine secreting cells in the lungs were DN NKT cells (FIG. 3E).

Figure 3G:
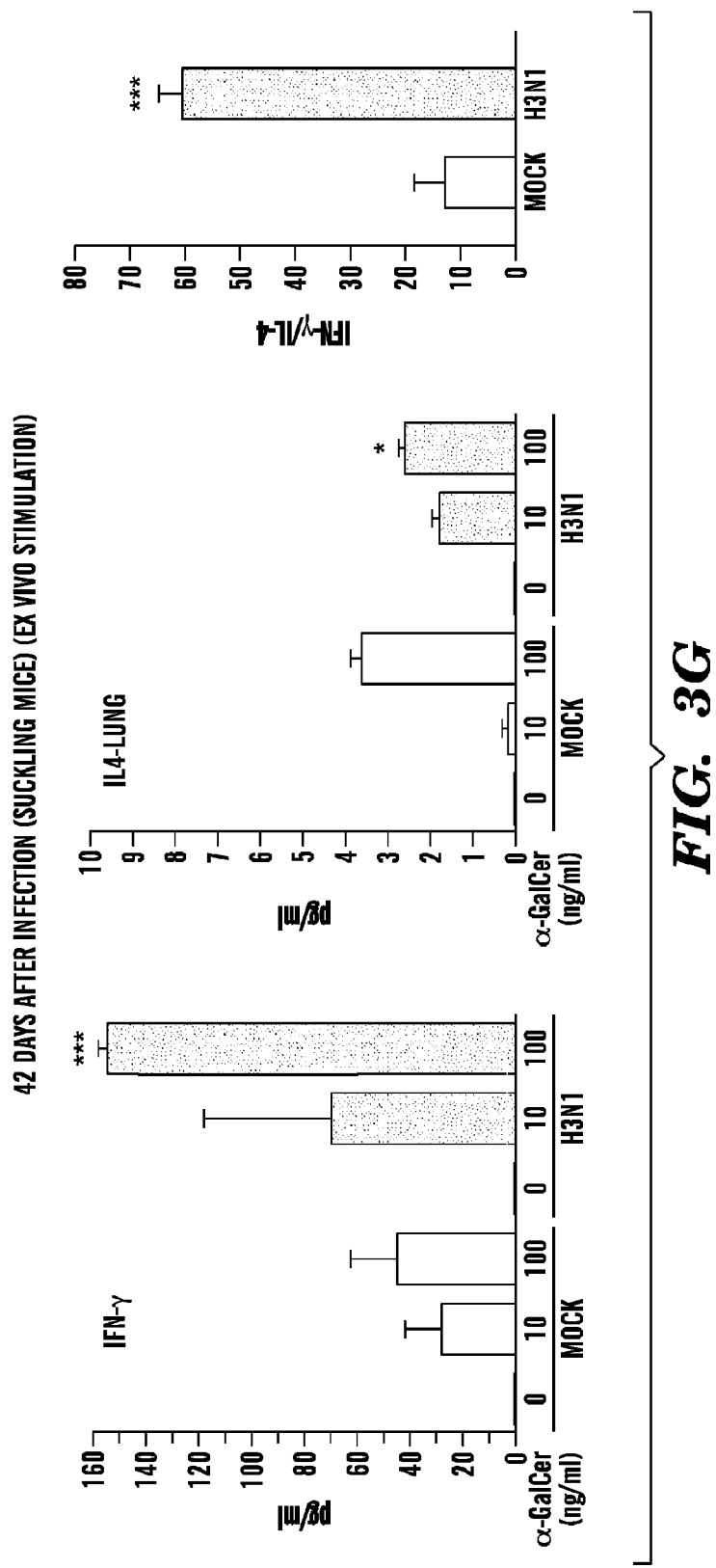

Analysis of the mice 42 days after H3N1 infection, showed that the proportion of DN versus CD4+ NKT cells in the lungs doubled, whereas 42 days post H3N1 infection in 8 wk old mice, there was no effect on the proportion of DN NKT cells in the lungs (FIG. 3F). Assessment of the cytokine profile of NKT cells 42 days post infection after ex vivo stimulation with α-Galactosylceramide (α-GalCer, which specifically activates NKT cells) demonstrated increased IFN-γ but not IL-4 production by the H3N1 exposed NKT cells (FIG. 3G), resulting in a greatly increased IFN-γ/IL-4 ratio (FIG. 3G, right panel). These results indicated that H3N1-infection in suckling mice preferentially expanded a unique NKT cell population in the lungs that by day 42, preferentially produced IFN-γ, but not IL-4, and was associated with a reduced expression of CD4.

Adoptive Transfer of H3N1 Exposed NKT Cells Suppresses AHR and Induces $T_{Reg}$ Cells.

Figure 4C:
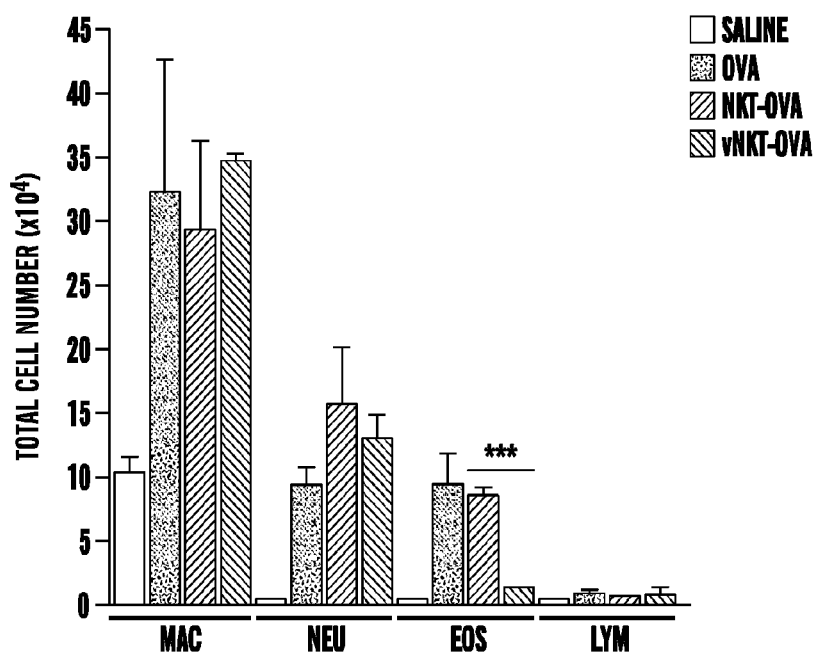
Figure 4D:
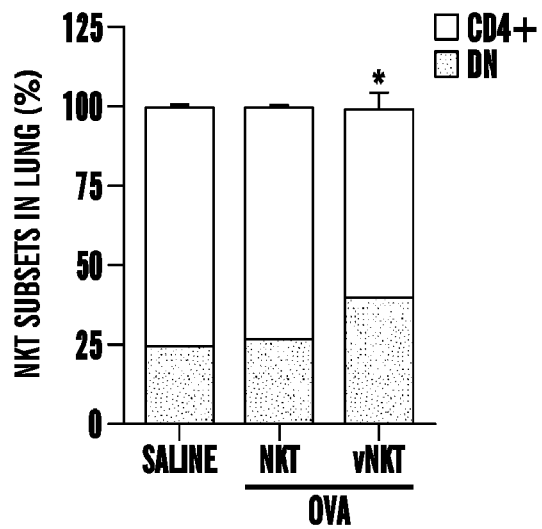

While the H3N1-exposed NKT cells (vNKT) could not induce AHR when transferred into Jα18$^{-/-}$ mice (FIGS. 2A-2D), they were not anergic, but instead potently suppressed OVA-induced AHR (FIGS. 4A and 4B) and inflammation (FIG. 4C), as assessed by adoptive transfer 42 days post-infection into adult wildtype OVA-sensitized mice. In contrast, NKT cells from mock-infected mice (WT NKT) (FIGS. 4B and 4C) or from adult mice infected with H3N1 did not suppress OVA-induced AHR. The proportion of DN NKT cells in the lungs of mice receiving the H3N1 virus-exposed NKT cells was increased (FIG. 4D), consistent with the idea that H3N1 infection in suckling mice preferentially expands a subpopulation of DN NKT cells.

Figure 4E:
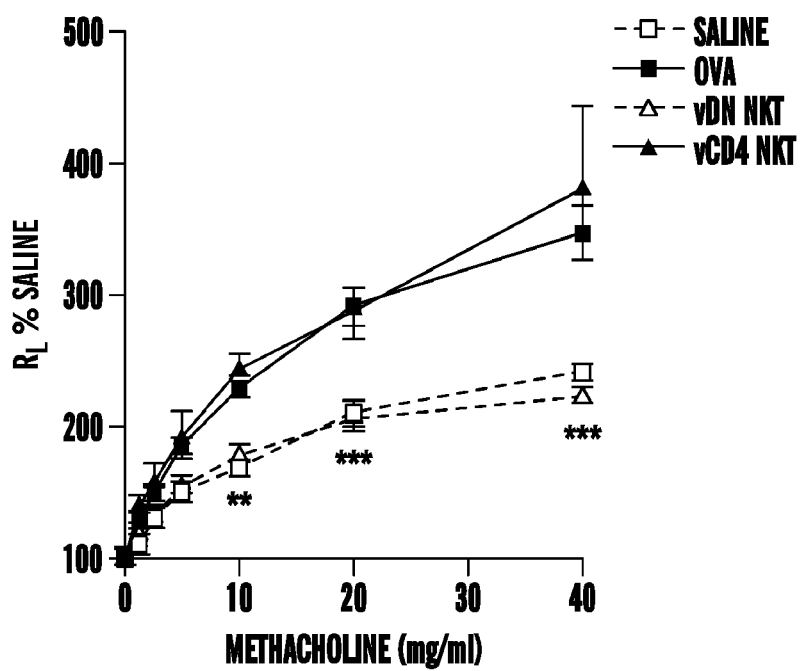

To more clearly demonstrate that the DN NKT cell subpopulation was responsible for the suppression of AHR, we purified CD4+ and DN NKT cell subpopulations from the spleens of mice (purity 96-99%) (FIG. 8C), which had been infected with H3N1, and adoptively transferred these cells into OVA sensitized mice. FIG. 4E shows that the DN but not the CD4+ NKT cell population suppressed AHR that developed on challenge of the mice with OVA, confirming that the H3N1-exposed DN NKT cell population was responsible for this effect.

Figure 4F:
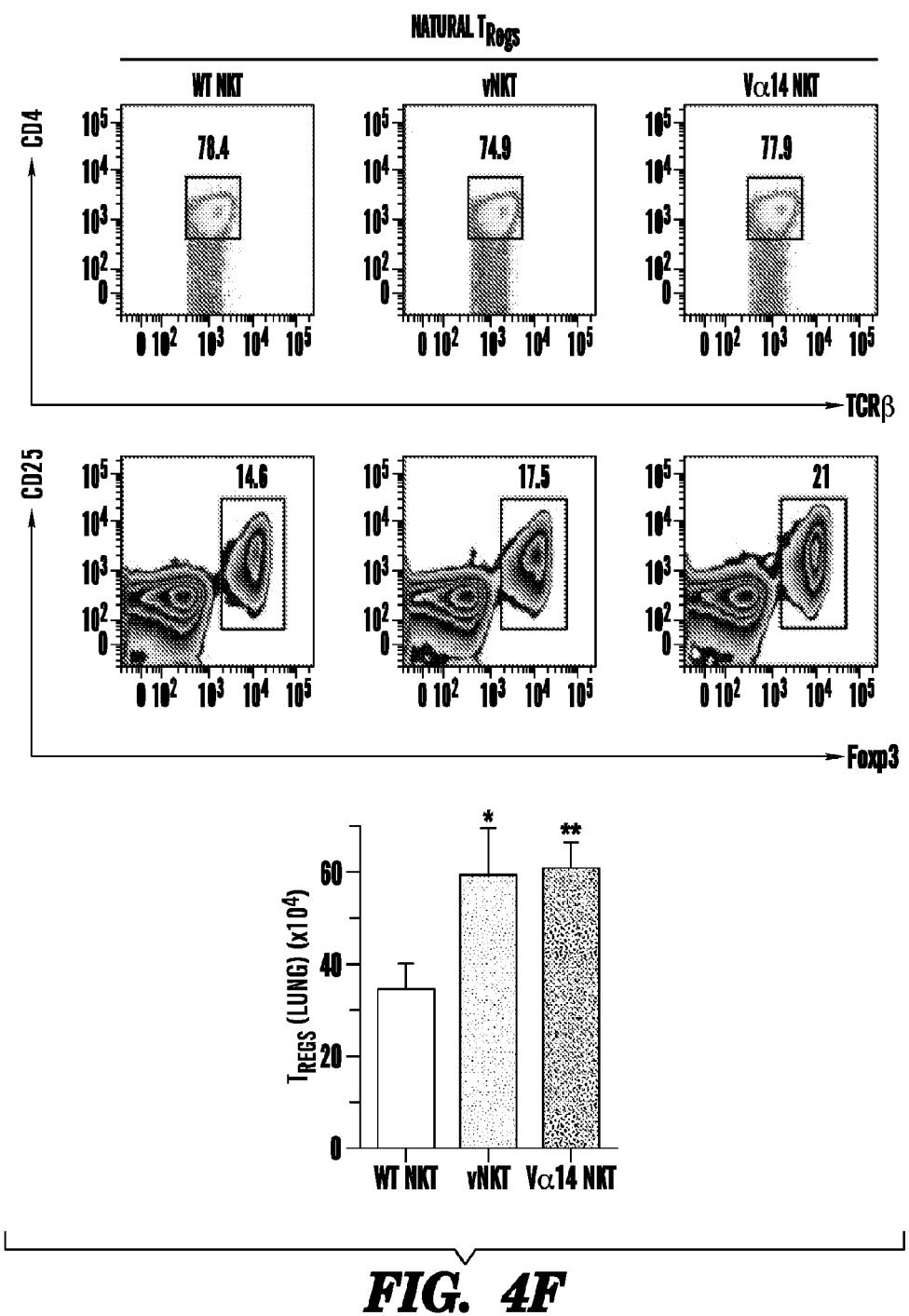
Figure 4F:
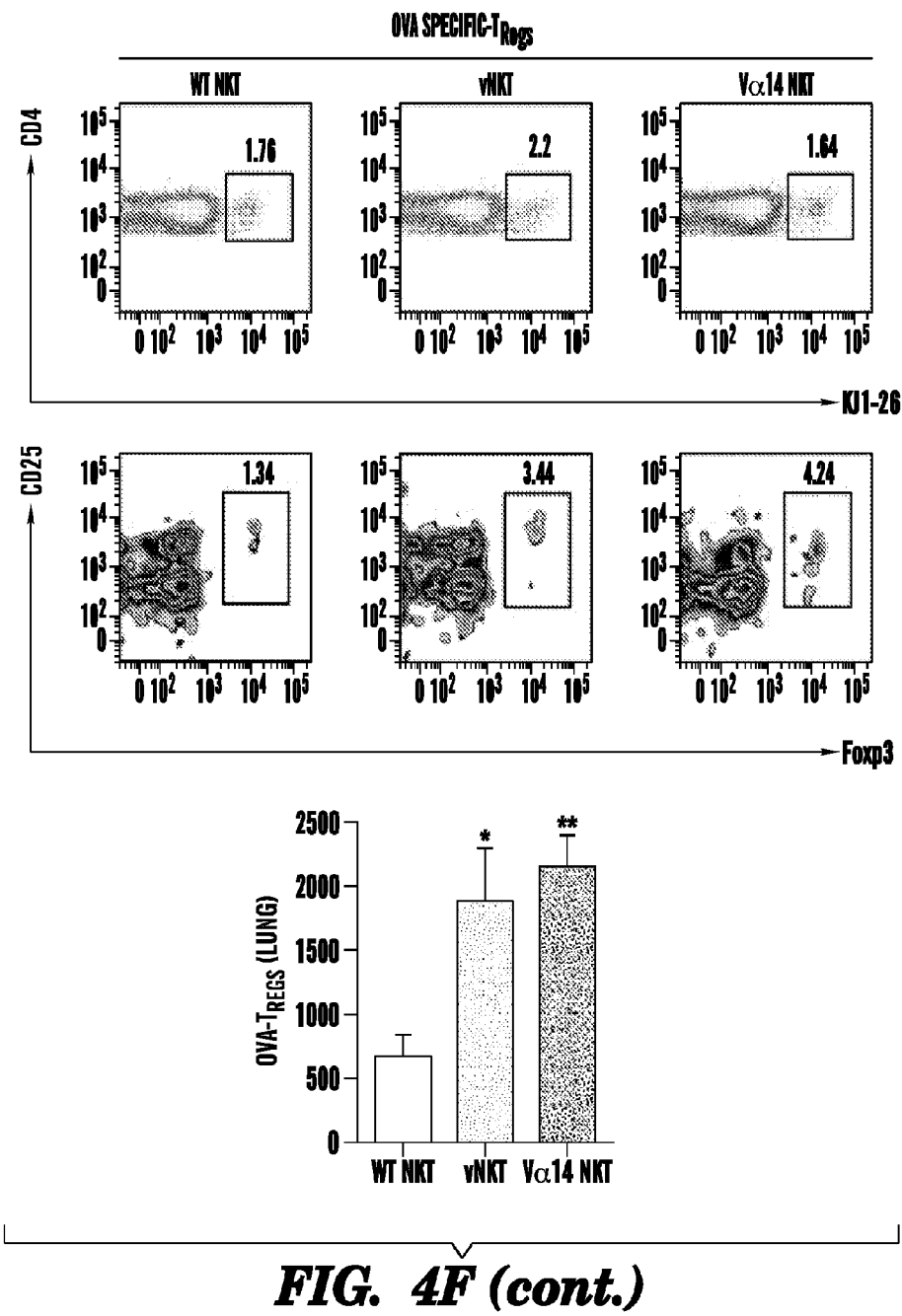
Figure 4G:
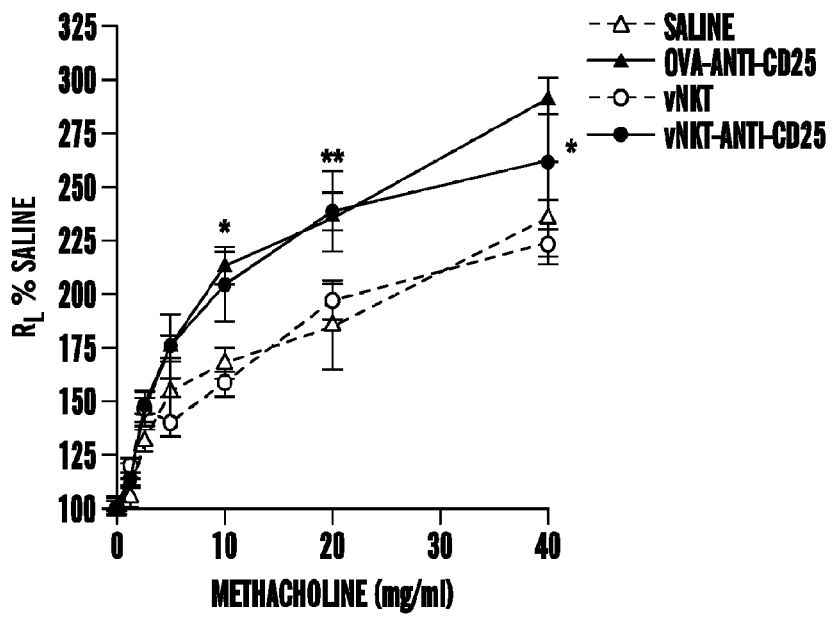

The suppression of AHR by the transferred H3N1-exposed NKT cells was associated with a 50% increase in the number of natural Foxp3+ $T_{Reg}$ cells, and in a 300% increase in the number of adaptive OVA-specific Foxp3+ $T_{Reg}$ cells in the lungs (assessed by transferring DO11.10 Tg OVA-specific Foxp3− T cells from DO11.10 Tg X Rag$^{-/-}$ mice), compared to when NKT cells from mock-infected mice were transferred (FIG. 4F). Furthermore, the inhibitory effect of the NKT cells exposed to H3N1 was reversed by treatment of the recipient mice with an anti-CD25 mAb (FIG. 4G). These results together indicated that H3N1-exposed NKT cells could suppress the development of experimental asthma, and that natural and adaptive $T_{Reg}$ cells can mediate the suppressive effects of the NKT cell population.

Figure 4H:
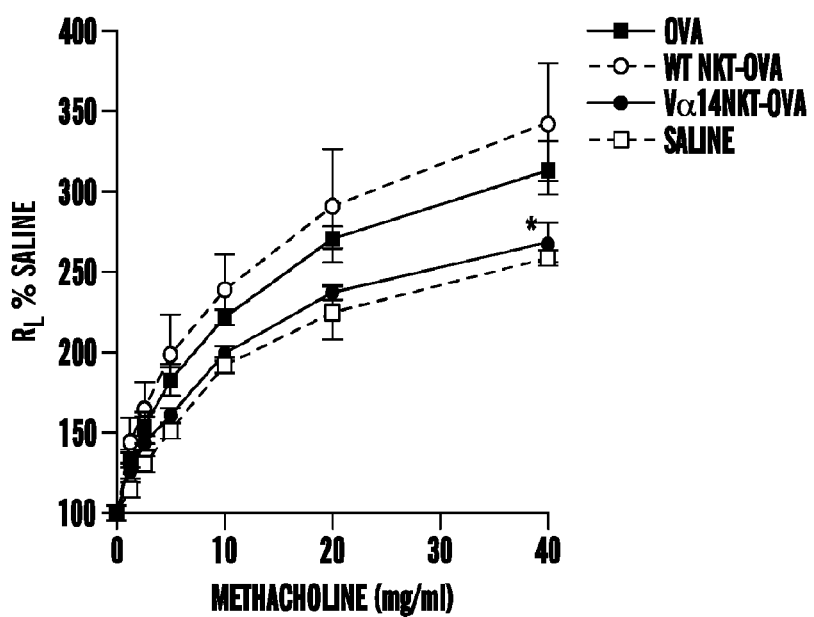
Figure 4I:
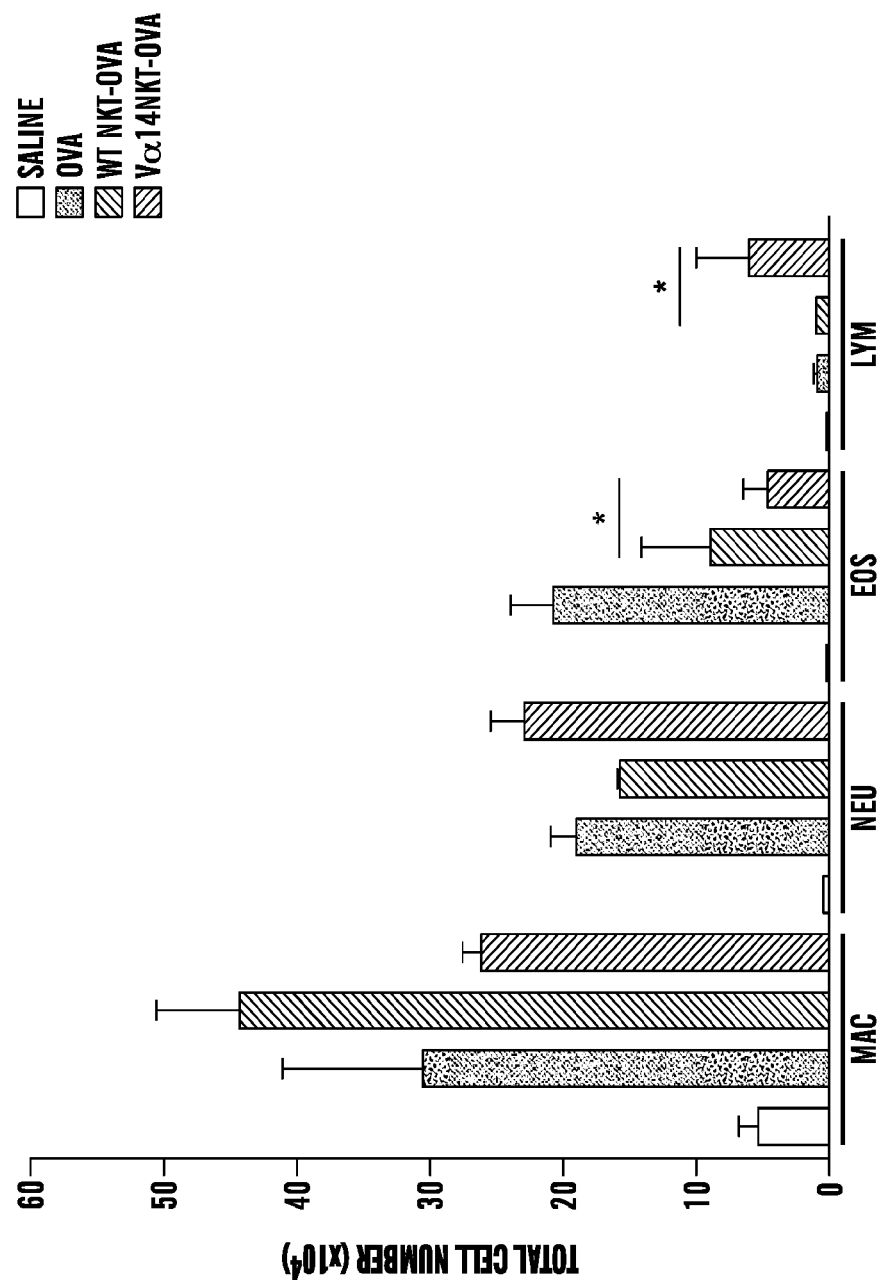
Figure 4J:
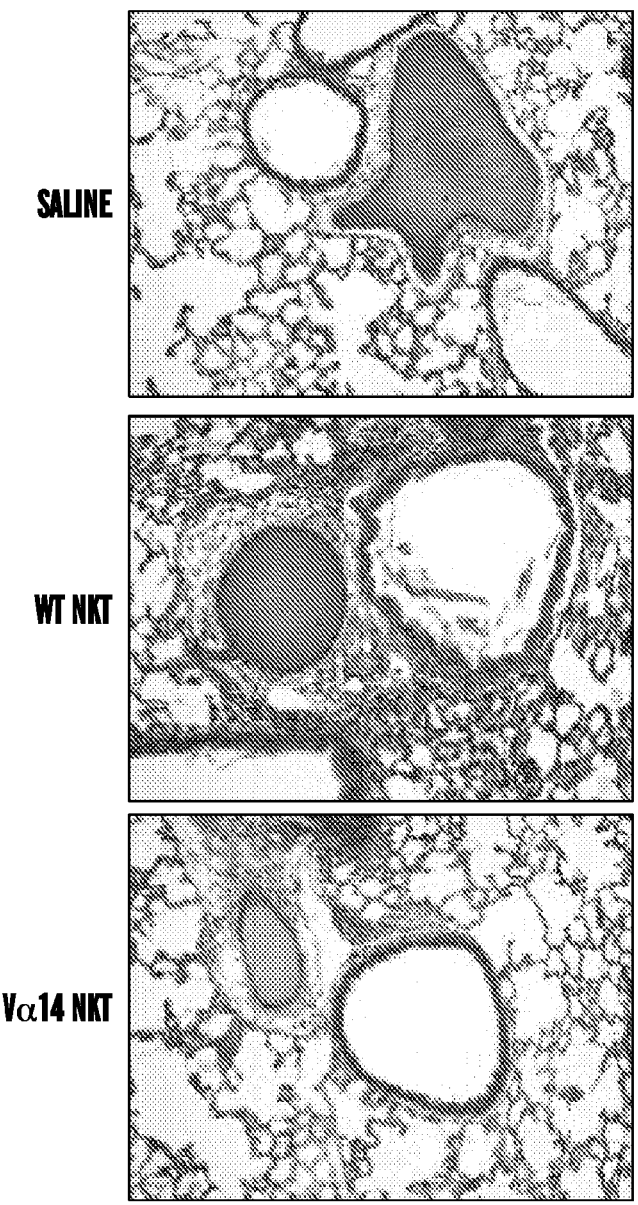
Figure 8B:
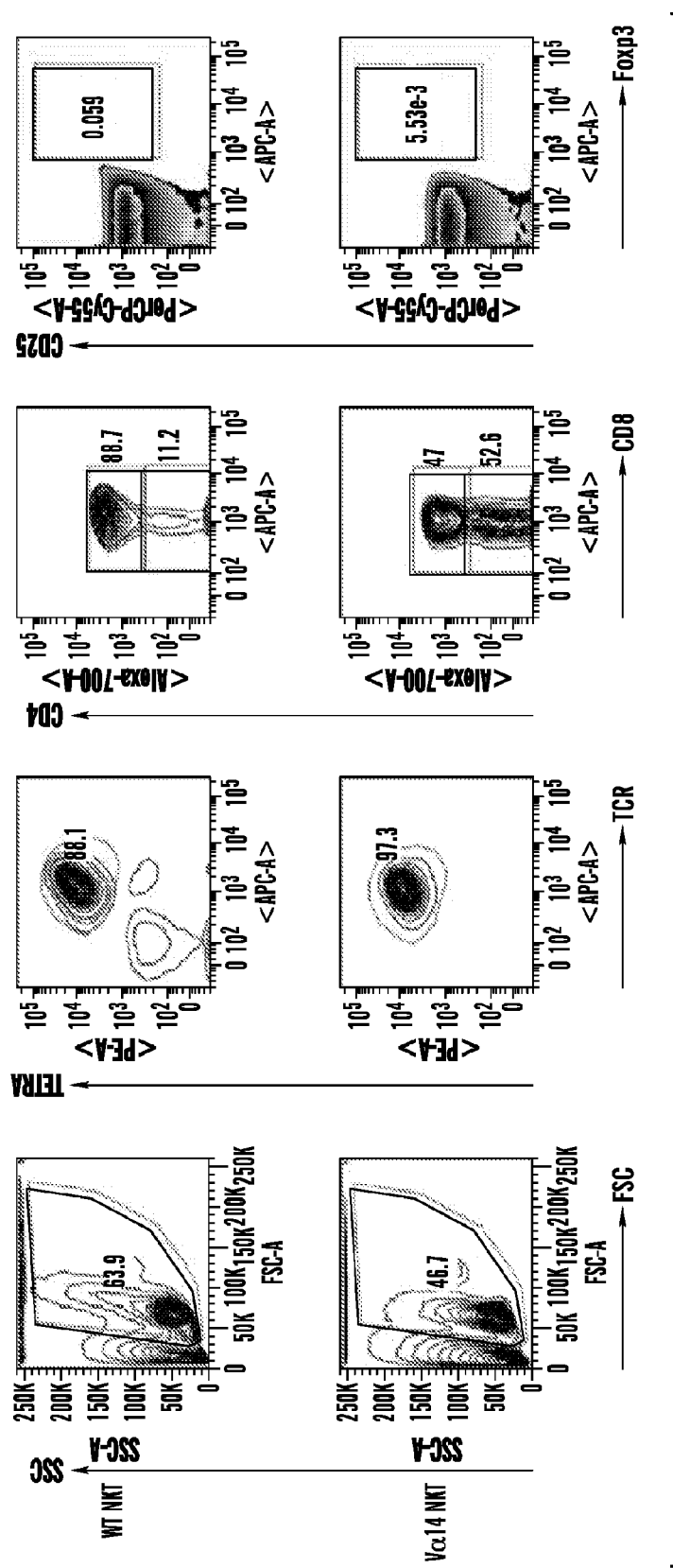
Figure 8C:
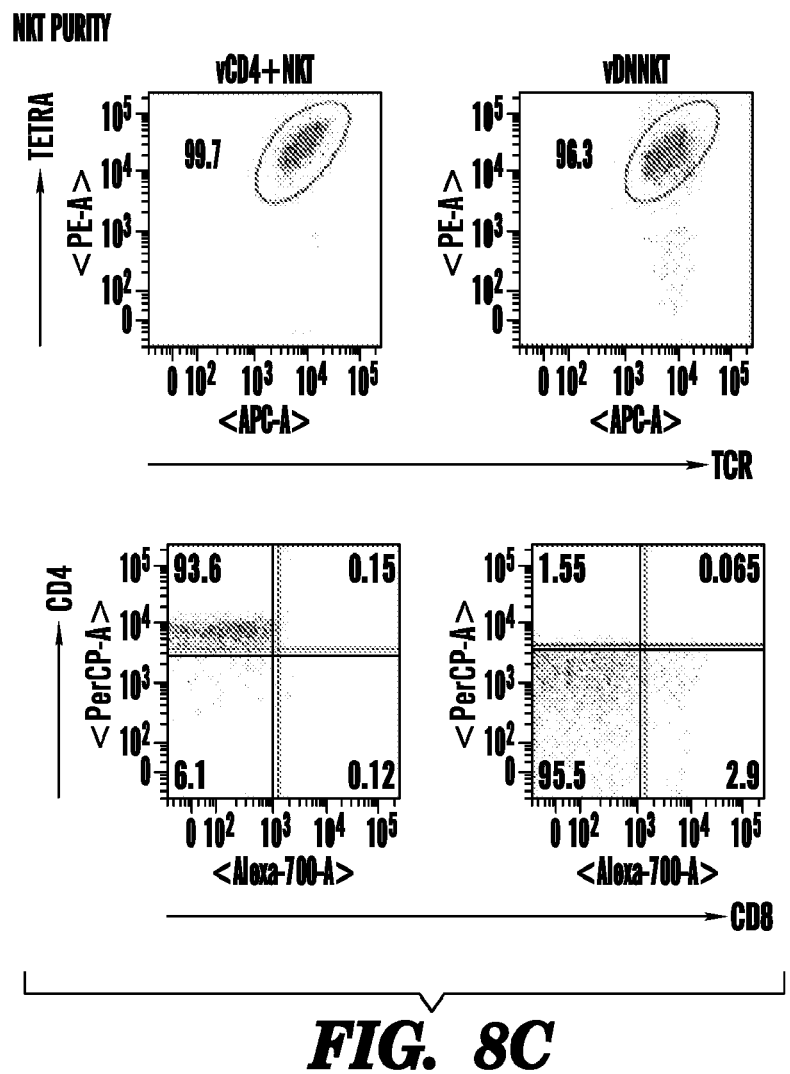

We found a similar suppressive NKT cell population in Vα14 TCR Tg mice. Adult Vα14 TCR transgenic mice have a 5-10 fold increase in the number of NKT cells in the spleen, of which the majority (53%) are DN NKT cells (FIG. 8B), whereas in WT BALB/c mice, only 11% of the splenic NKT cells are DN (FIG. 8B). Adoptive transfer of NKT cells purified from Vα14 TCR Tg mice into adult WT OVA-sensitized BALB/c mice greatly suppressed the development of OVA-induced AHR and airway inflammation (FIGS. 4H, 4I and 4J). Transfer of Vα14 TCR Tg NKT cells was also associated with a 50% increase in the number of natural Foxp3+ $T_{Reg}$ cells, and in a 300% increase in the number of adaptive OVA-specific Foxp3+ $T_{Reg}$ cells (assessed by transfer of DO11.10 Tg OVA-specific cells), compared to when naïve (WT) NKT cells were transferred (FIG. 4F). These results suggest that NKT cells in Vα14 Tg mice, were similar to NKT cells from suckling mice exposed to H3N1 in having suppressive activity for allergen-induced AHR.

the Protective Effect of H3N1 Infection Depends on TLR7 and T-Bet.

Figure 5A:
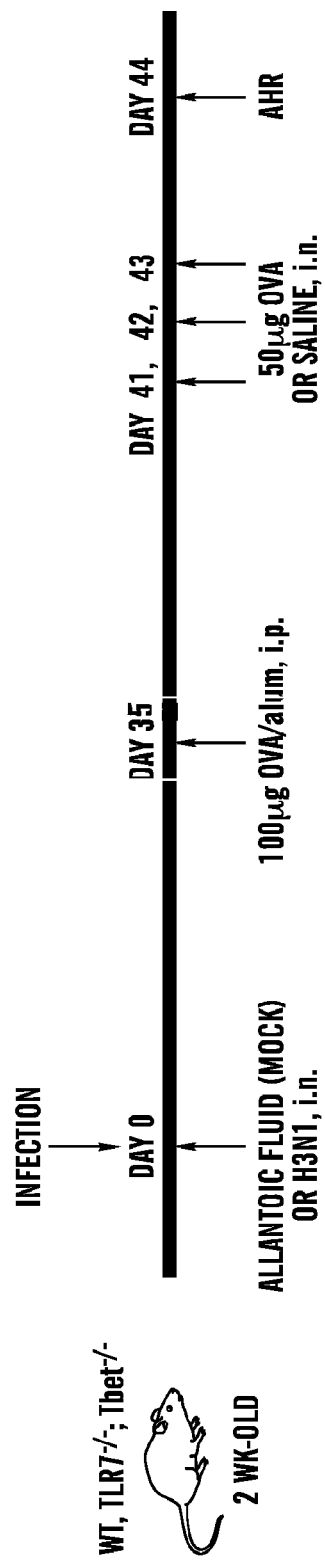
FIGS. 5A-5F demonstrate that protective effects of H3N1 infection depend on TLR7 and T-bet.
Figure 5B:
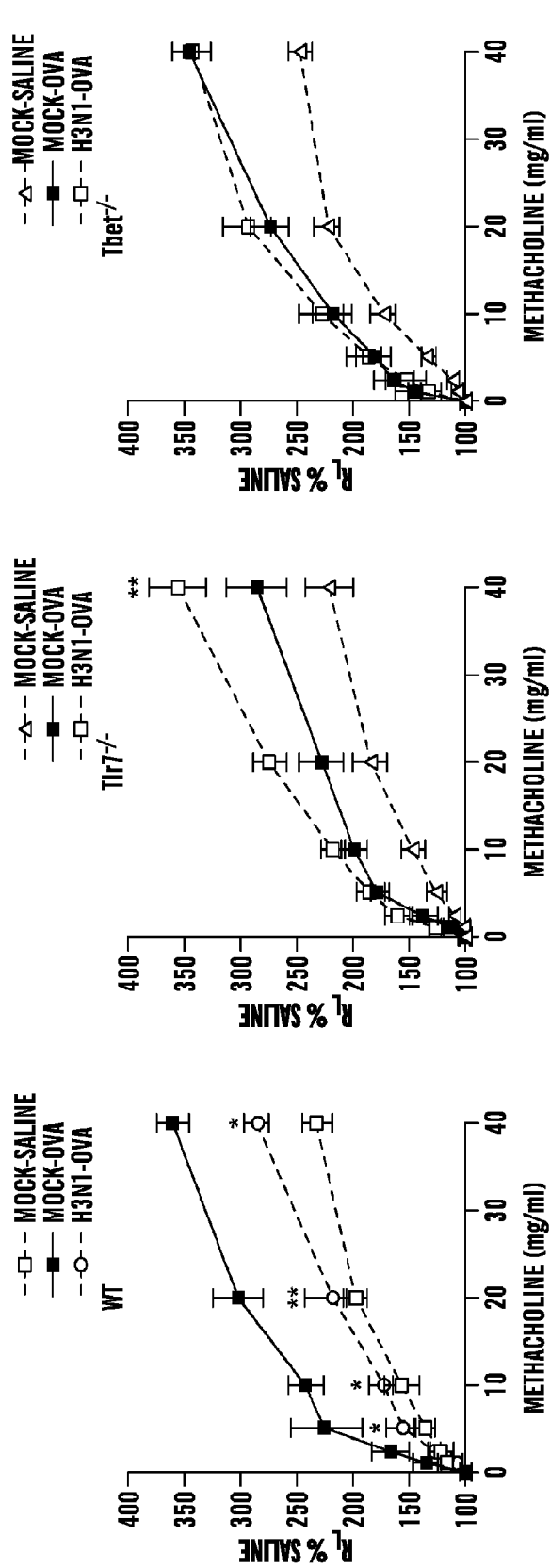
Figure 5C:
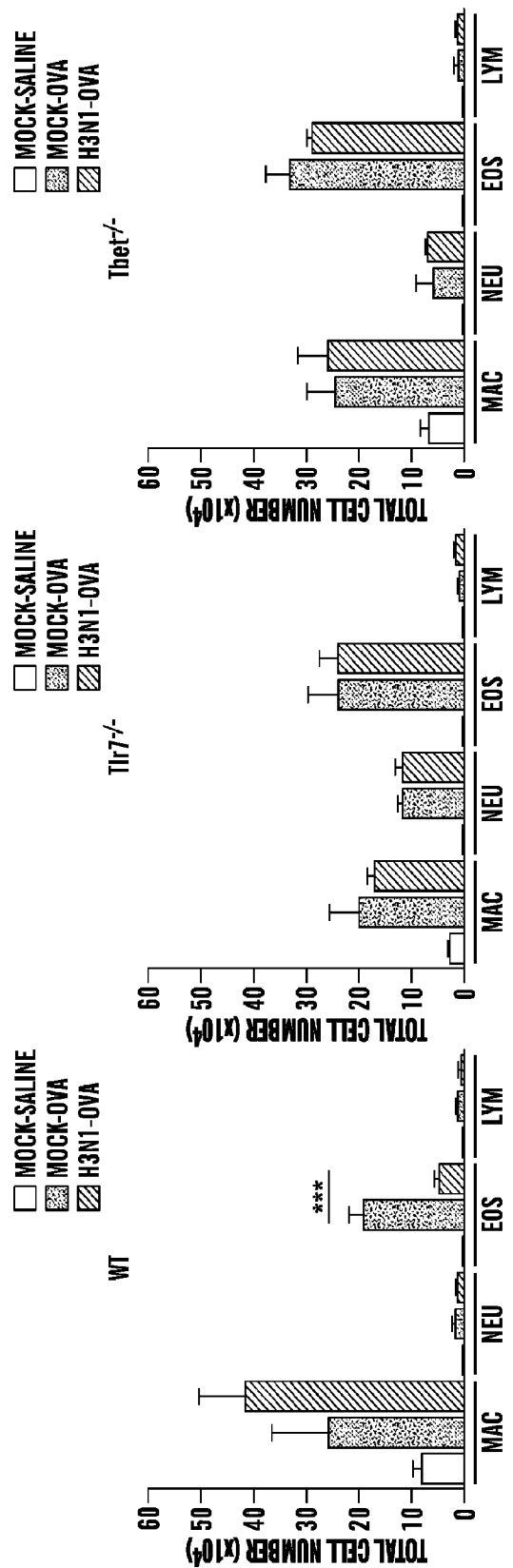
Figure 5D:
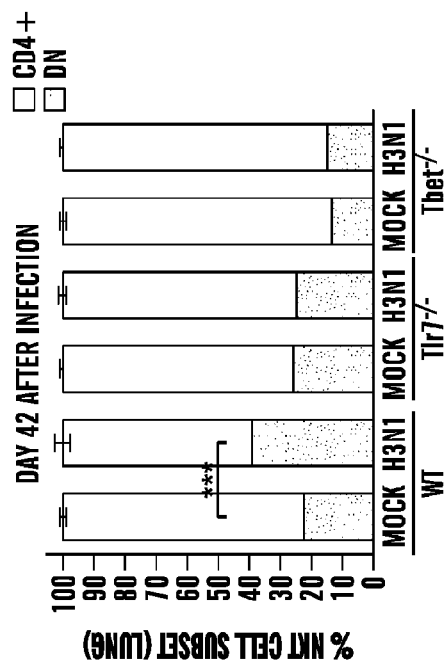
Figure 5E:
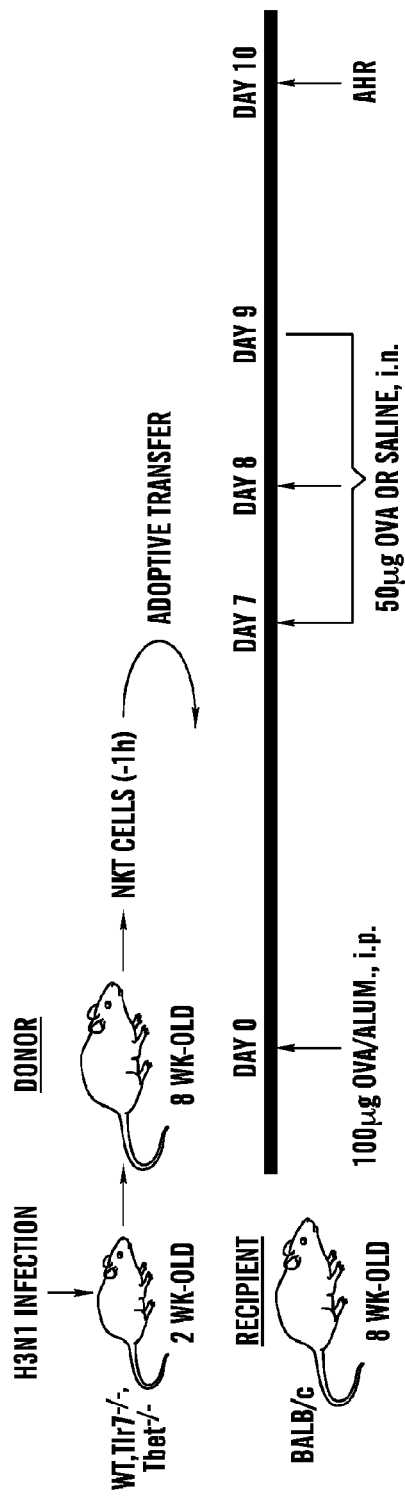
Figure 5F:
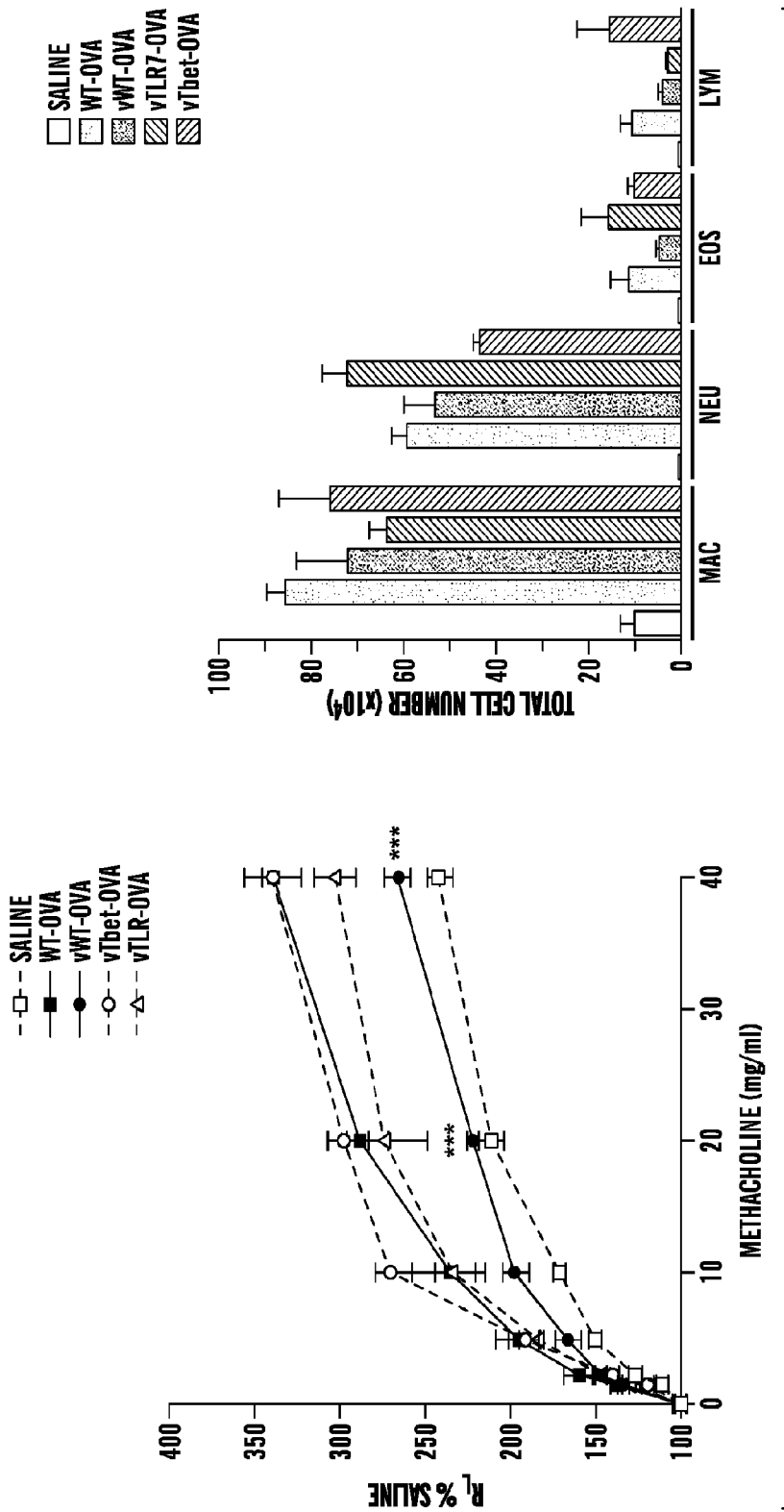
Figure 9D:
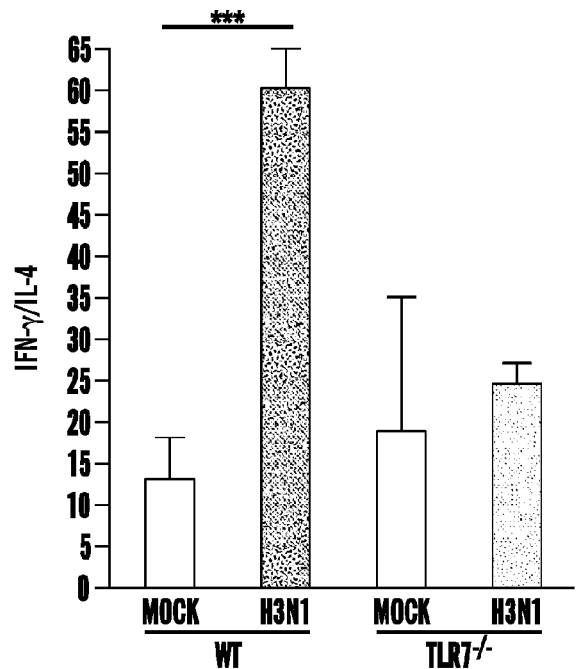
Figure 9E:
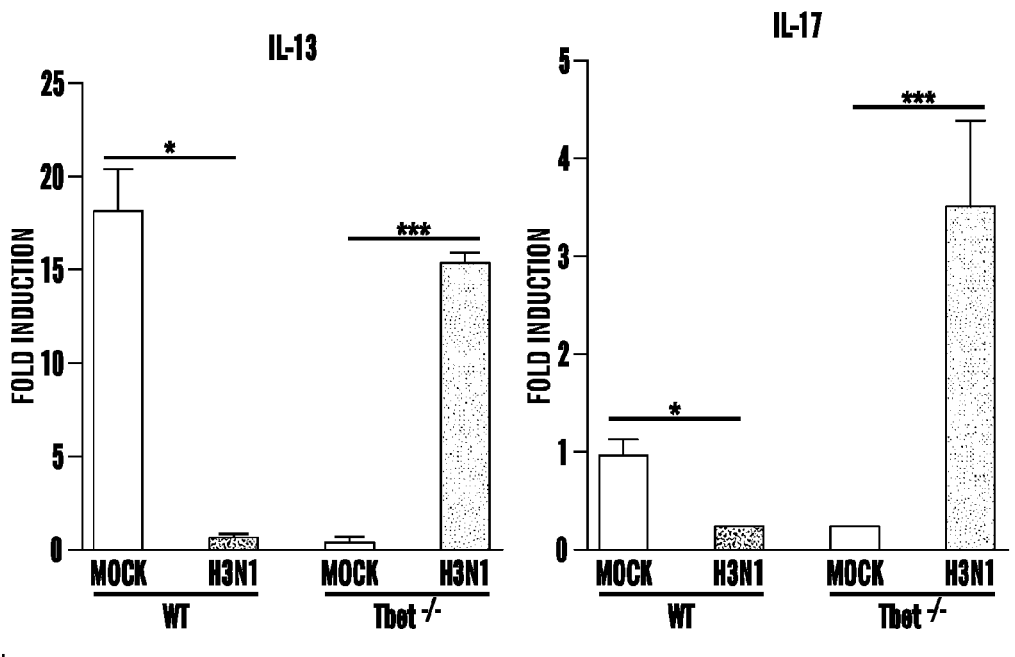
In FIG. 9E, total RNA from H3N1-infected WT or T-bet$^{-/-}$ mice lung cells were isolated on day 42, and analyzed by QRT-PCR for IL-13 or IL-17 mRNA expression. *$p<0.05$, ***$p<0.001$, compared to the mock group.

Since influenza A virus is a ssRNA virus, and since T-bet participates in IFN-γ production and in NKT cell maturation (23), we infected 2 wk old TLR7$^{-/-}$, T-bet$^{-/-}$ mice and control WT BALB/c mice with the H3N1 virus. 6 wks later, the mice were examined for OVA-induced AHR (protocol shown in FIG. 5A). Whereas H3N1 infection in suckling WT mice protected against subsequent OVA-induced AHR and airway inflammation (FIGS. 5B and 5C), H3N1 infection in suckling TLR7$^{-/-}$ or suckling T-bet$^{-/-}$ mice failed to protect against, and even exacerbated, OVA-induced AHR and airway inflammation. Furthermore, the ratio of IFN-γ/IL-4 production in NKT cells from TLR7−/− mice was reduced (FIG. 9D), while IFN-γ was reduced and IL-13 and IL-17 production increased in NKT cells in T-bet$^{-/-}$ mice, compared to WT mice (FIGS. 9A and 9E). (Note that T-bet$^{-/-}$ mice have reduced numbers of NKT cells, particularly in the liver (23), but have significant numbers of pulmonary NKT cells compared to WT mice (24)). As noted earlier (FIG. 3F), protection against AHR was associated with an increase in the number of DN NKT cells following H3N1 infection in WT mice, which did not occur in TLR7$^{-/-}$ or T-bet$^{-/-}$ mice (FIG. 5D). Moreover, adoptive transfer of NKT cells purified 6 weeks after H3N1 infection of WT, but not TLR7$^{-/-}$ or T-bet$^{-/-}$ mice, into OVA-sensitized WT BALB/c mice suppressed OVA-induced AHR and airway inflammation (FIGS. 5E and 5F). Taken together, these results indicated that protection by H3N1-exposed NKT cells against AHR are dependent on TLR7 and T-bet.

Induction of Protection with α-C-GalCer and a Glycolipid from *H. pylori*.

Figure 6B:
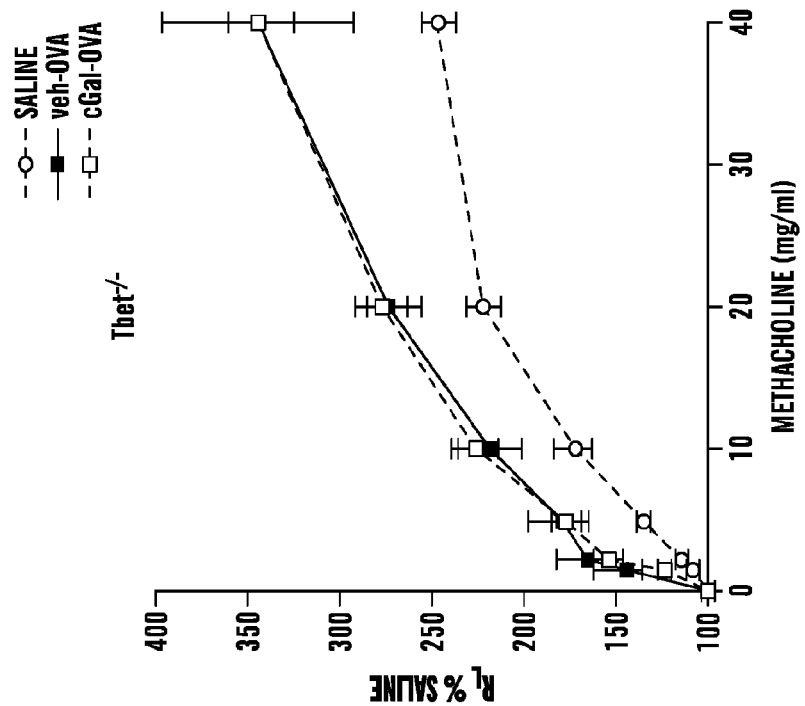
FIGS. 6A-6G demonstrate induction of protection with α-C-GalCer and a glycolipid from *H. pylori*.
Figure 6A:
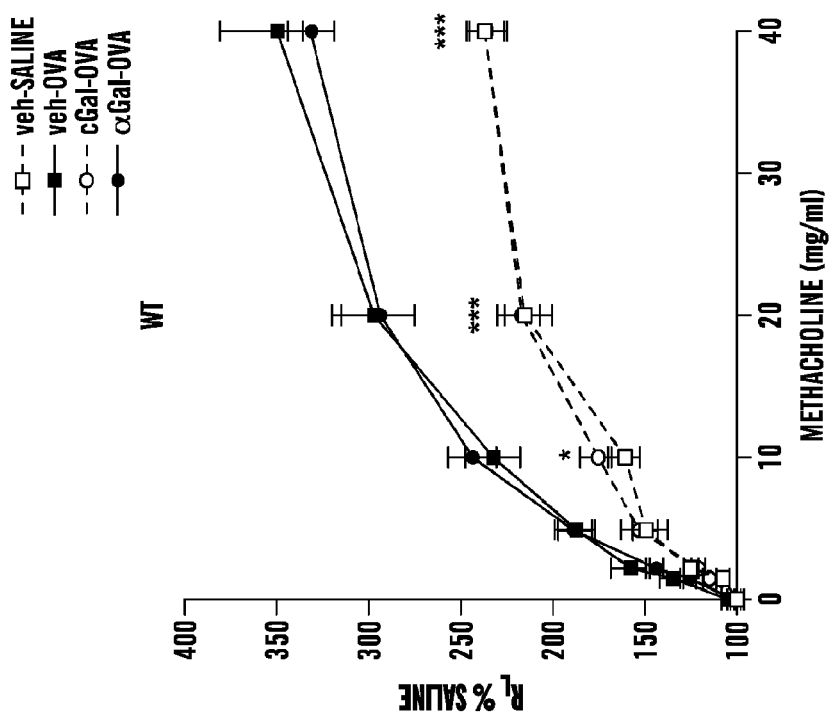
Figure 6C:
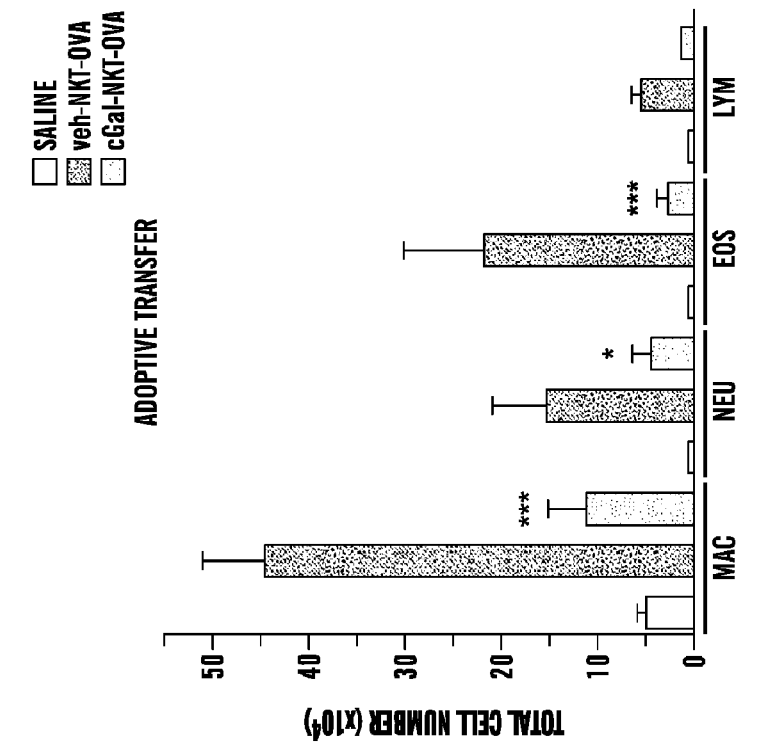
Figure 6C:
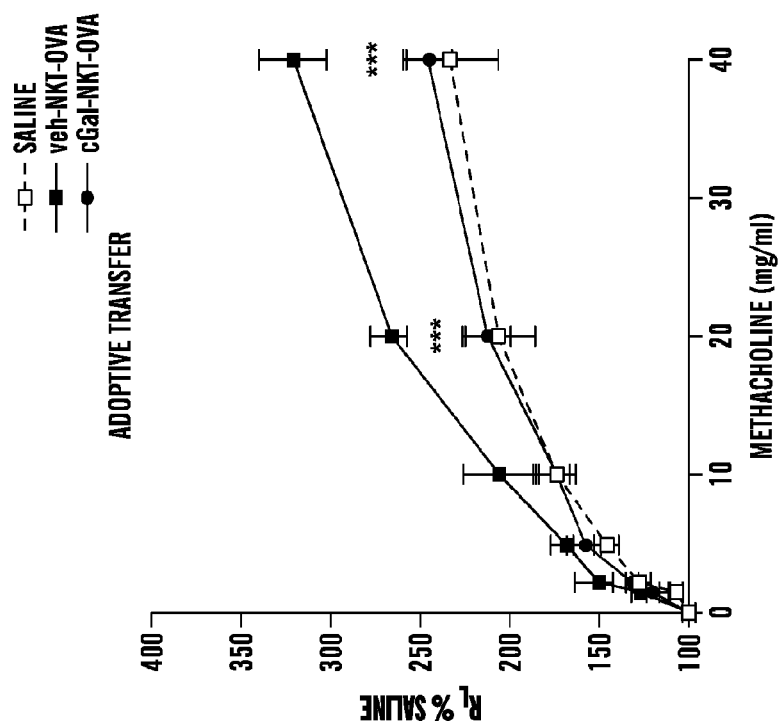

Since NKT cells appeared to mediate the effects of H3N1 infection, we examined a panel of glycolipids that specifically activate NKT cells for the capacity to replicate the beneficial effects of H3N1 infection. We first examined the effects of α-C-GalCer, a synthetic C-glycoside analog of α-GalCer that preferentially induces IFN-γ but not IL-4 synthesis (25-27). Treatment of suckling mice with α-C-GalCer (5 µg), but not α-GalCer, which induces production of both IFN-γ and IL-4, protected the mice as adults (42 days later) from the development of OVA-induced AHR (FIG. 6A). The protective effect was dependent on T-bet, since Tbet$^{-/-}$ mice were not protected by treatment with α-C-GalCer (FIG. 6B). Moreover, adoptive transfer of NKT cells exposed to α-C-GalCer protected recipients against the development of AHR and airway inflammation (FIG. 6C).

Figure 6D:
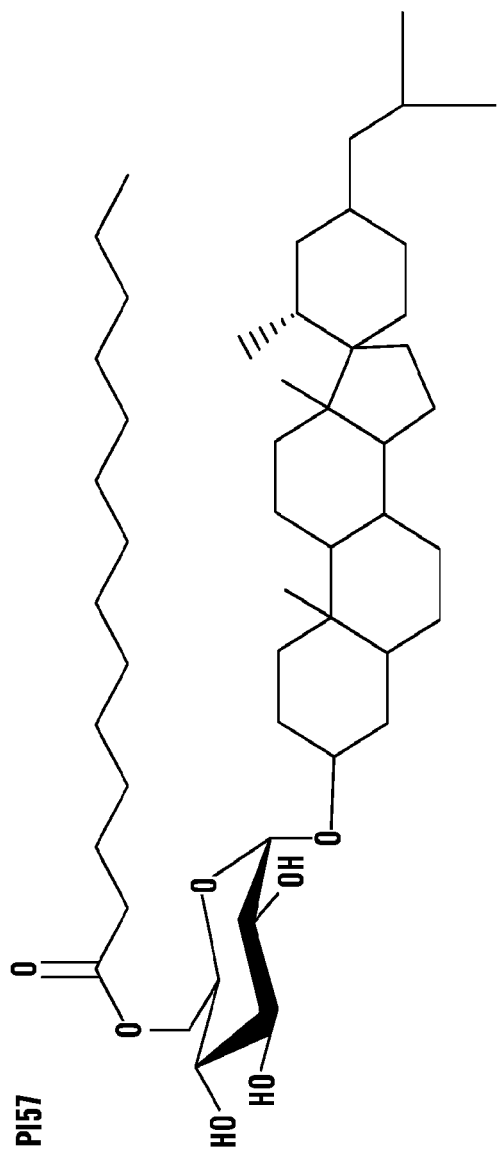
Figure 6E:
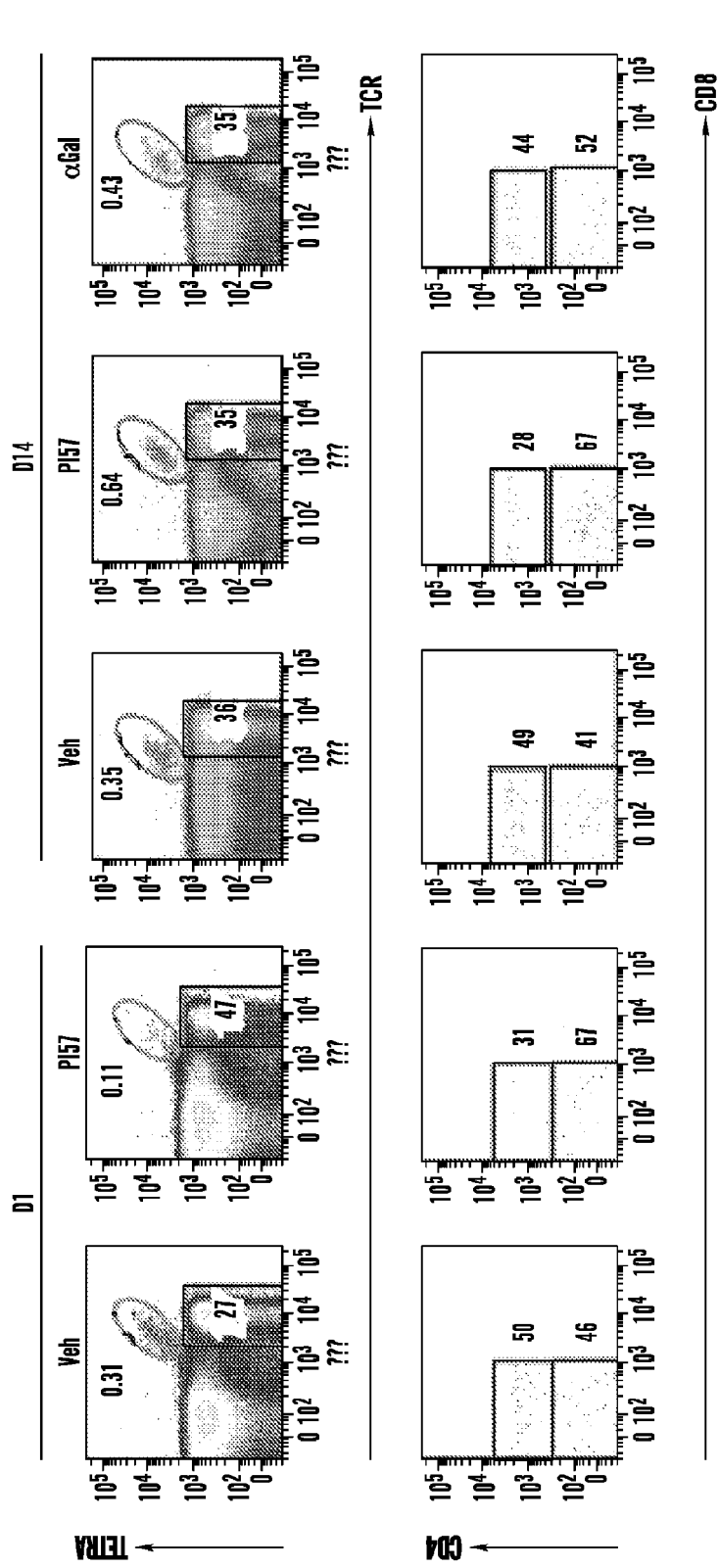
Figure 6F:
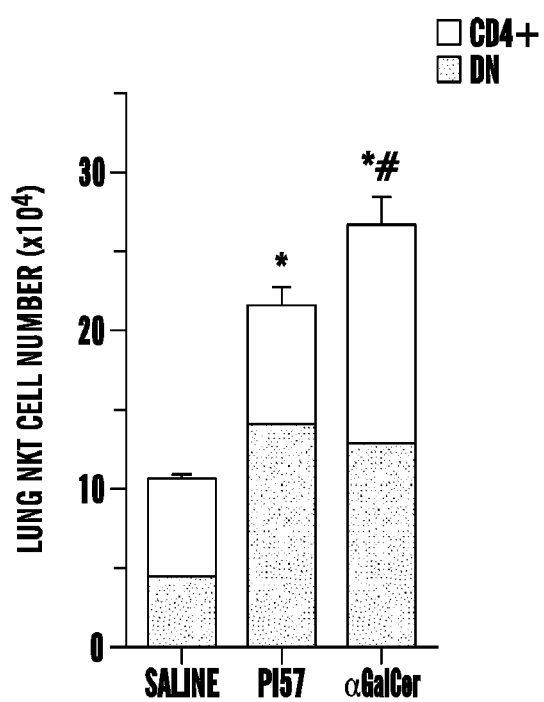
Figure 6G:
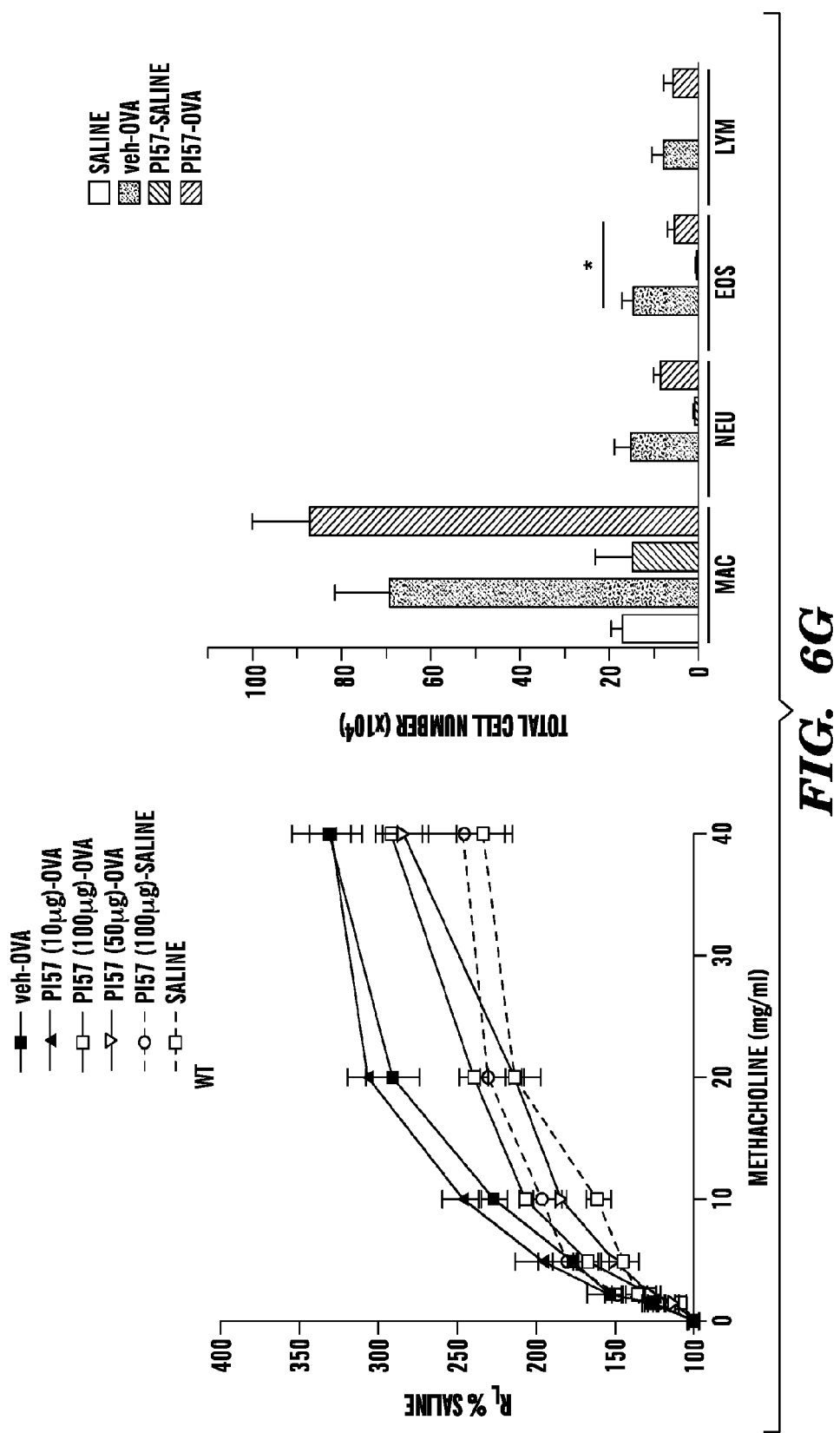
Figure 6H:
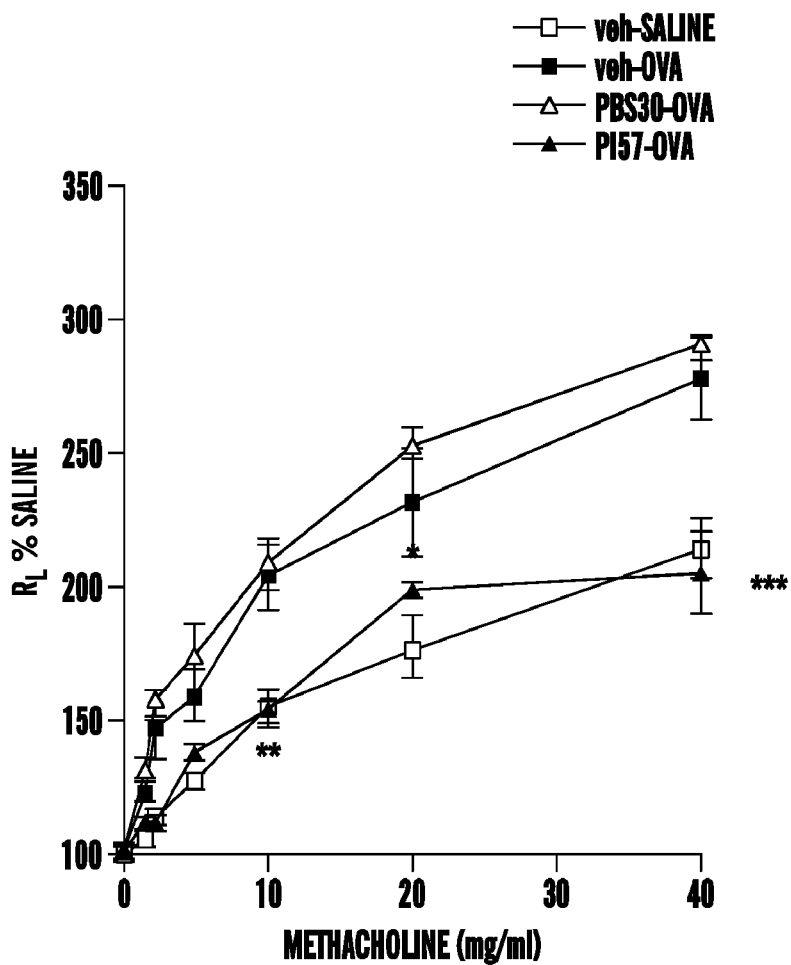
In FIG. 6H, BALB/c mice treated with PI57 (50 μg), PBS30 (*Sphingomonas* glycolipid) (50 μg), or vehicle i.p. were assessed for AHR as in 6G.
Figure 6I:
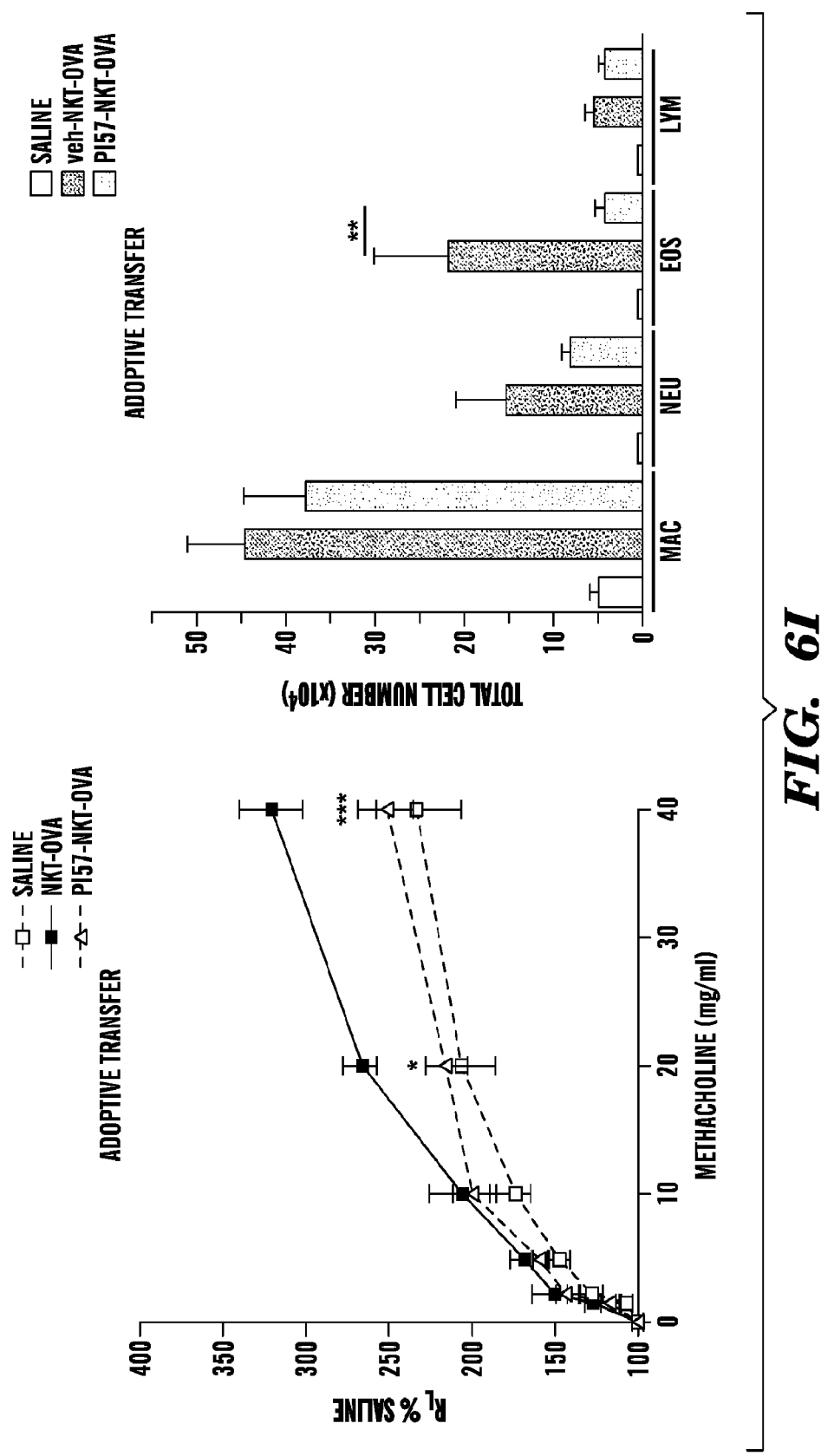
In FIG. 6I, donor mice were treated with PI57 (50 μg) or vehicle i.p. NKT cells served as donors as in FIG. 4A. Lung resistance (left) and BAL cells (right) were assessed (n=4 per group).
Figure 6J:
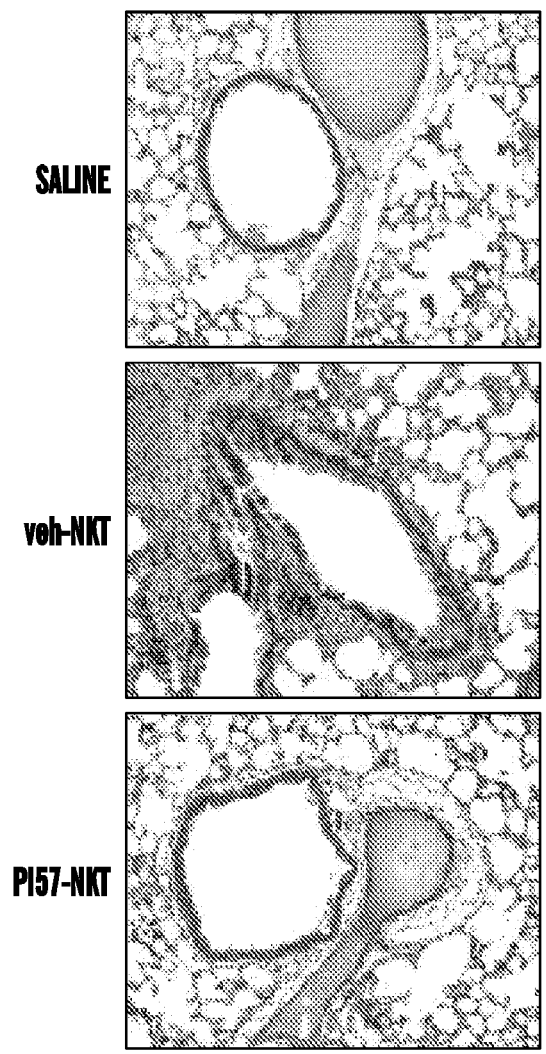
FIG. 6J shows representative lung sections from 6I stained with H&E (original magnification, ×10). Data represent 2-3 independent experiments. *P<0.05, #P<0.05, ***P<0.001 versus vehicle-OVA (6C, 6G, and 6I), DN NKT saline (6F), and CD4$^+$ NKT saline (6F).
Figure 10A:
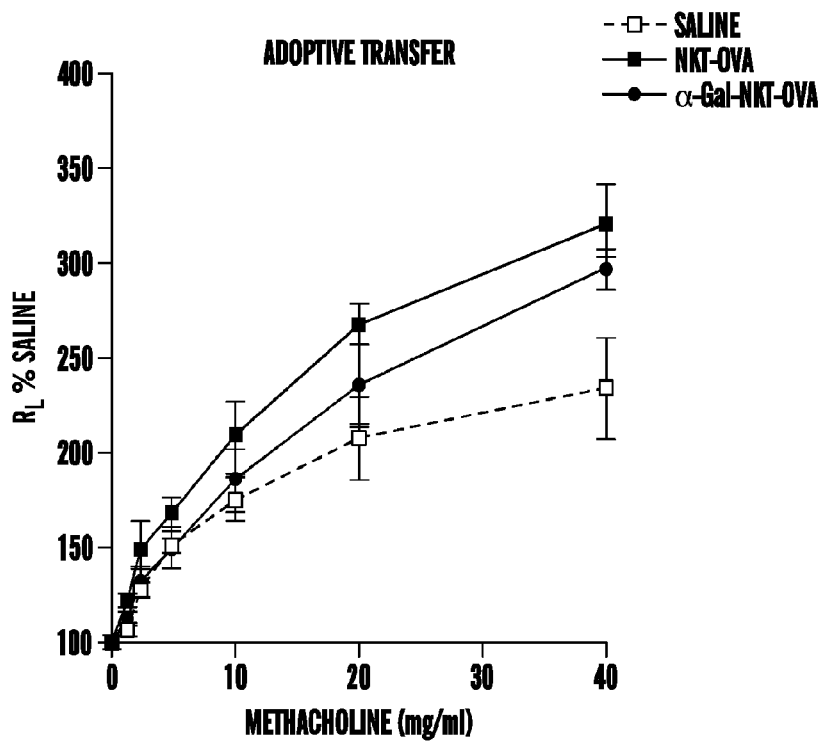
FIGS. 10A-10B demonstrate that treating 2 wk-old mice with α-GalCer did not prevent OVA induced AHR.
Figure 10B:
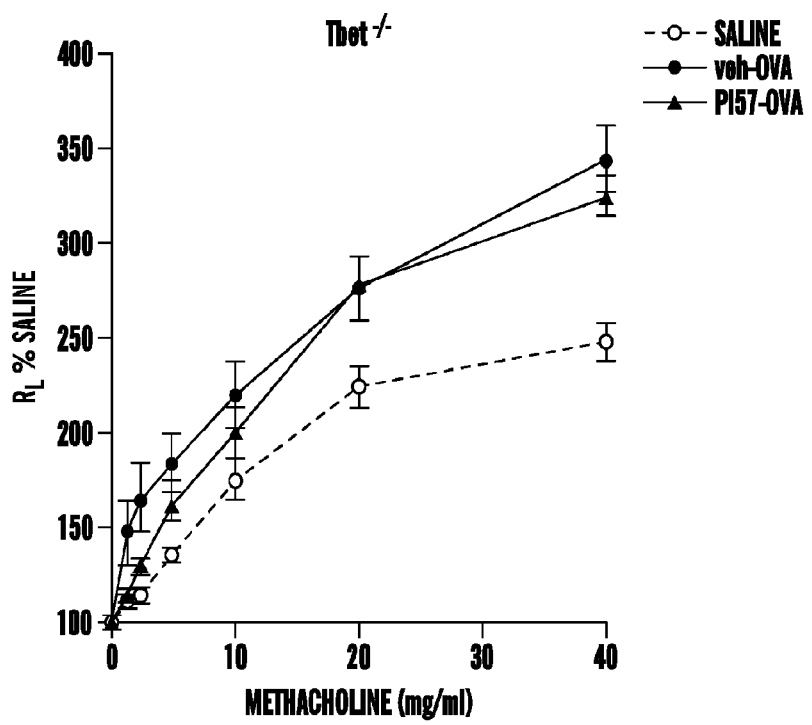

We also found a second glycolipid, PI57, a cholesterol-derived lipid from *H. pylori* (28), that could protect against the development of AHR (FIG. 6D). *H. pylori*, a bacteria that colonizes the stomach (29) and which is associated with protection against asthma (2, 3), produces cholesteryl α-glucosides (30), including cholesteryl 6-O-acyl α-glucoside (AGlc-Chol) (FIG. 11), which was chemically synthesized (PI57) (FIG. 6D). PI57, when administered i.p. to 2 week-old mice, increased the total number of NKT cells, particularly the number of DN NKT cells, found in the lung 2 wks later (FIGS. 6E and 6F). In contrast, treatment with α-GalCer increased both CD4$^+$ and DN NKT cells in the lungs. Importantly, treatment of 2 wk old mice with PI57 (50 or 100 μg) (FIG. 6G) protected the mice from the development of OVA-induced AHR, induced 6 wks after the glycolipid treatment. On the other hand, treatment of 2 wk old mice with PBS30, a lipid present in the cell walls of *Sphingomonas* bacteria (31, 32), failed to protect the mice from OVA-induced AHR (FIG. 6H). Moreover, adoptive transfer of NKT cells from PI57 treated, but not vehicle-treated, 2 wk old mice (harvested 6 wks after treatment) into OVA-sensitized WT mice, suppressed AHR and airway inflammation (FIGS. 6I and 6J). Transfer of NKT cells from α-GalCer treated mice reduced AHR slightly, but this was not statistically significant (FIG. 10A). The production of IFN-γ by the NKT cells was important, since the protective effect of PI57, like that of H3N1 and α-C-GalCer, was dependent on T-bet, since PI57 treatment of 2 wk old T-bet$^{-/-}$ mice did not protect against subsequent OVA-induced AHR (FIG. 10B). These results together indicate that a subset of NKT cells that can be specifically activated by some but not all glycolipid antigens and that preferentially produces IFN-γ mediate the protective effects of H3N1 infection.

PI57 is a CD1d-Dependent NKT Cell Antigen.

Figure 7A:
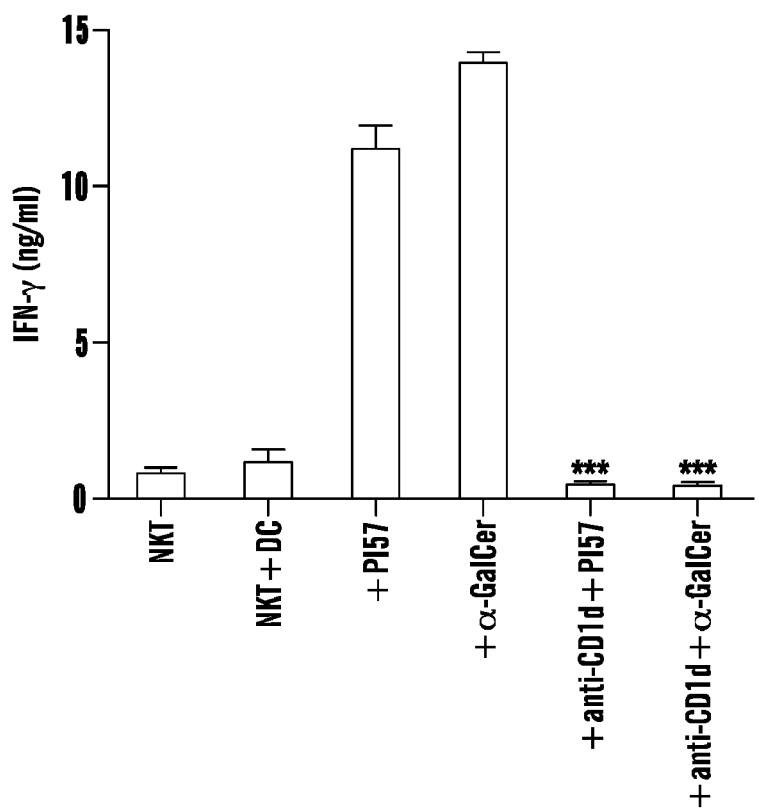
Figure 7B:
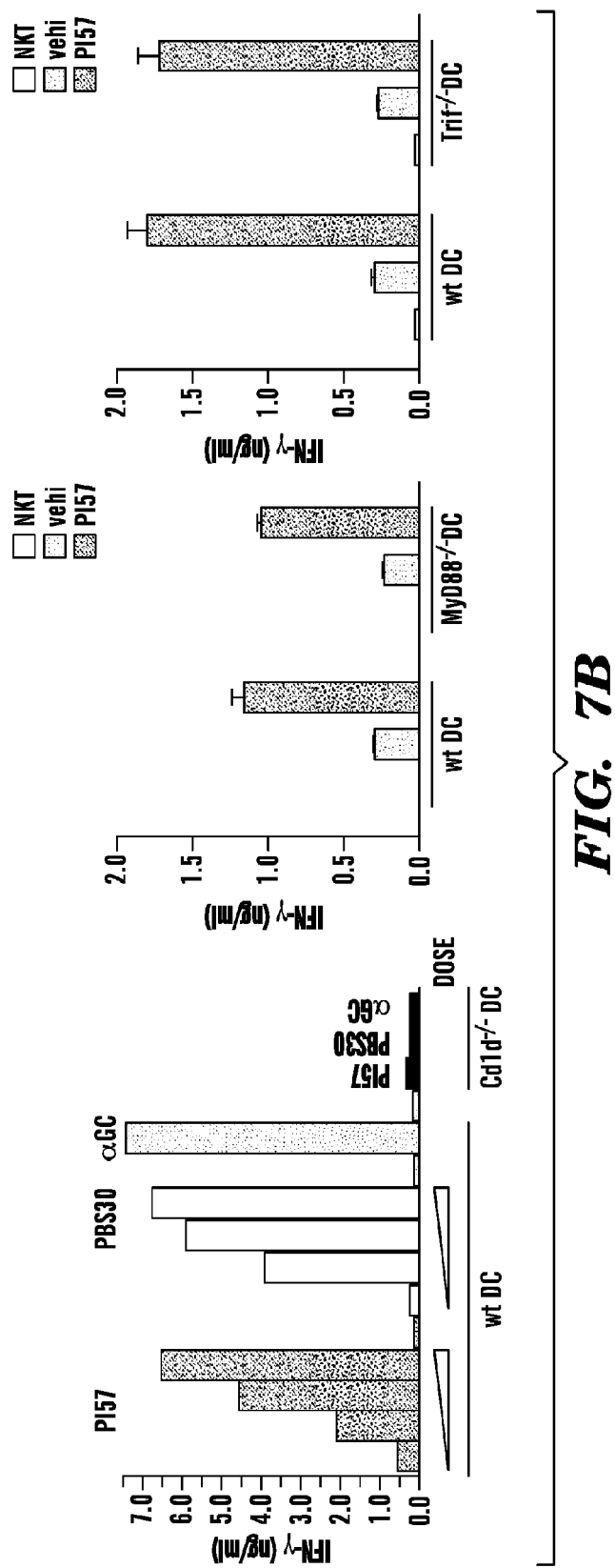
Figure 7B:
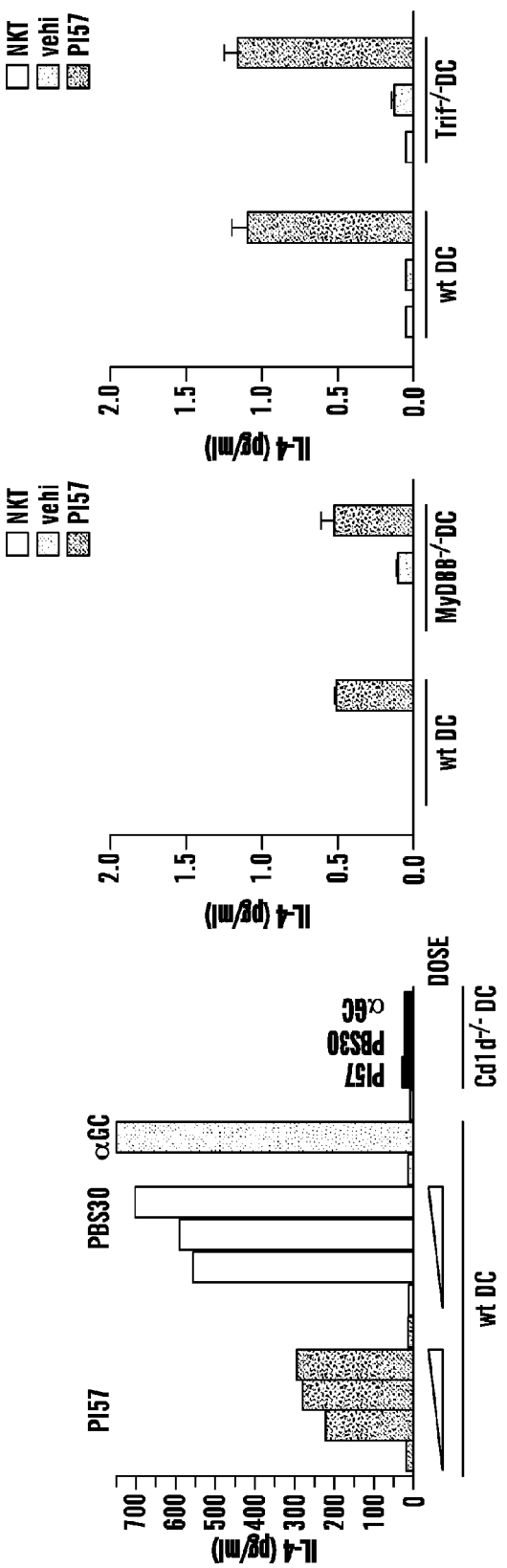
Figure 7C:
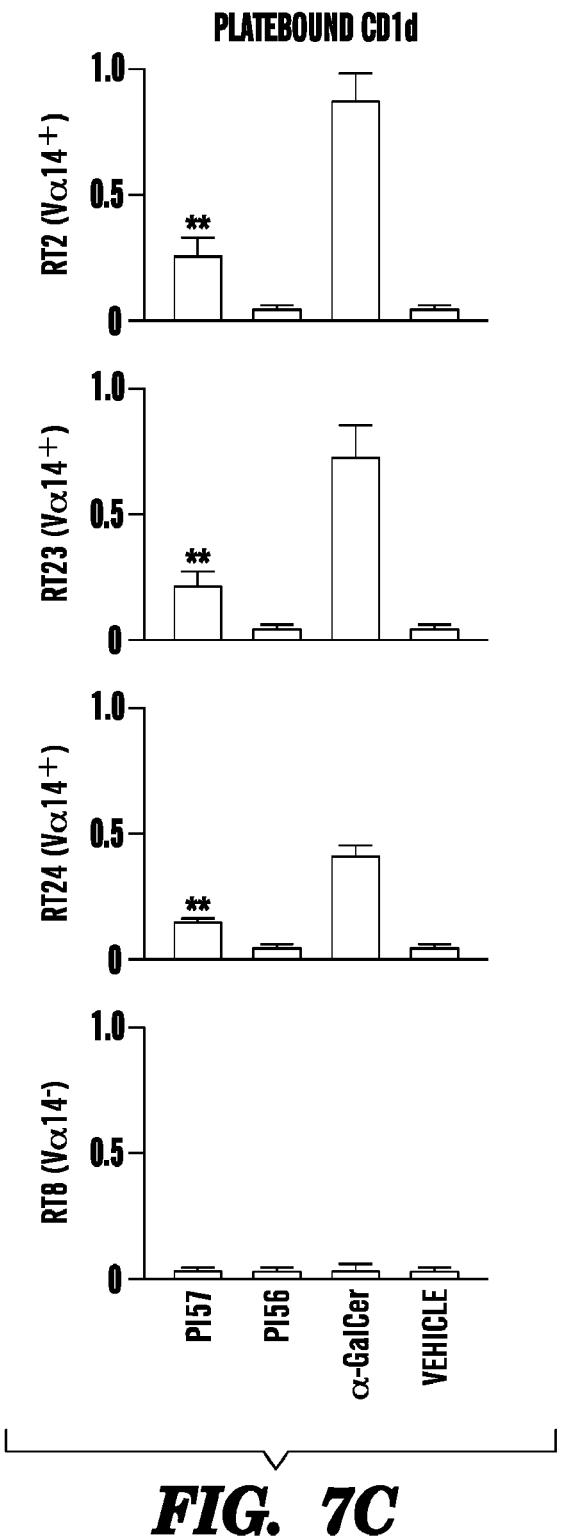
Figure 7D:
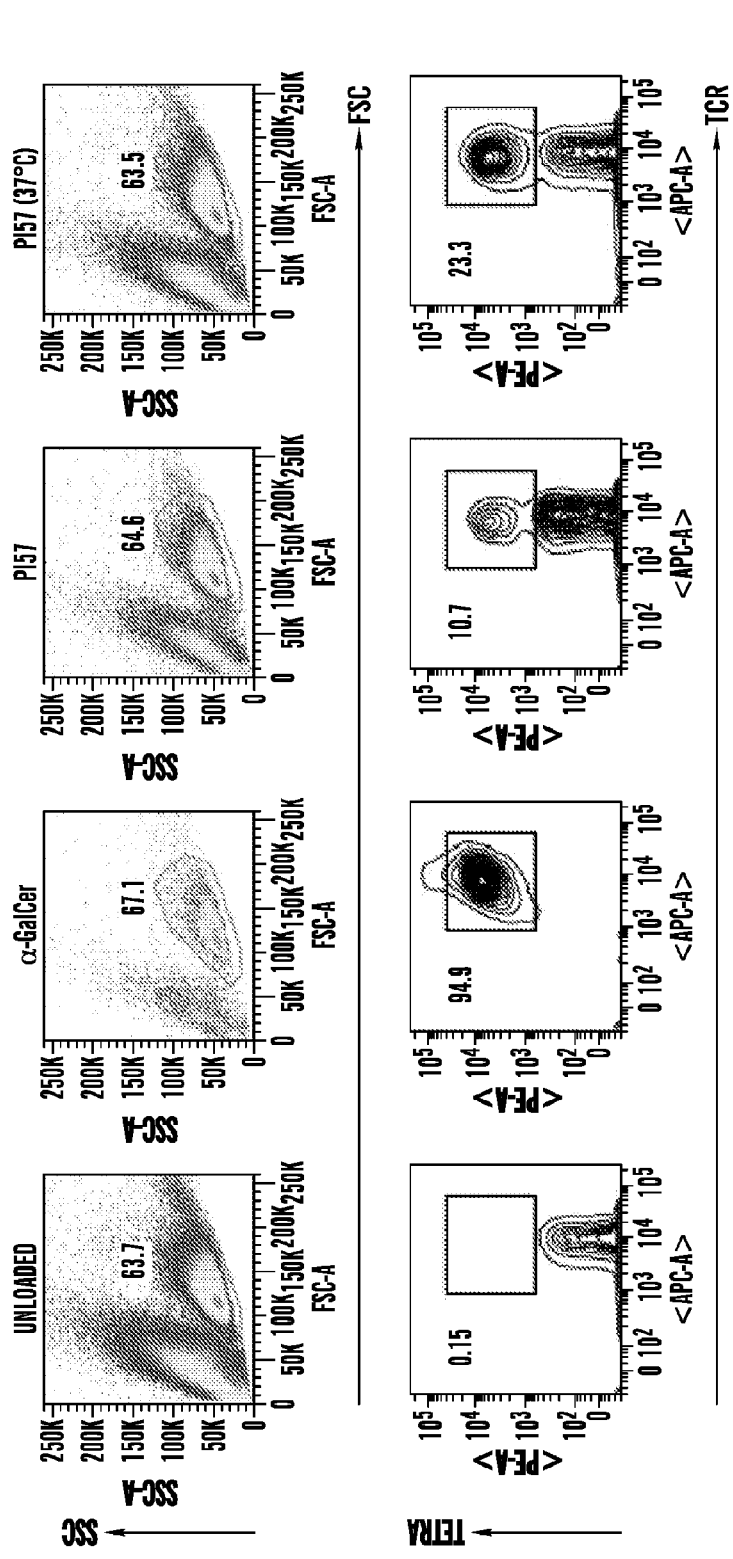

To demonstrate that PI57, like α-C-GalCer, can directly activate NKT cells, we showed that PI57, when added to cultures of NKT cell lines+dendritic cells (DCs), induced the production of IFN-γ in a CD1d-restricted manner, since cytokine production was blocked by anti-CD1d mAb (FIG. 7A). In addition, PI57, induced IFN-γ and less IL-4 in NKT cell lines, compared to PBS30 (from *Sphingomonas*) or α-GalCer, and did so in a CD1d restricted manner, since DCs from CD1d$^{-/-}$ mice failed to support PI57 induced cytokine production (FIG. 7B, left panels). Furthermore, the PI57 response occurred by direct activation of NKT cells, since PI57 induced cytokine production in NKT cell lines with DCs from MyD88$^{-/-}$ or Tri$^{-/-}$ mice (FIG. 7B, middle and right panels), and since three different NKT cell hybridomas derived from Vα14 NKT but not from Vα14-T cells, produced IL-2 in response to immobilized recombinant CD1d previously loaded with PI57 but not with PI56, a control glycolipid (FIG. 7C). Moreover, CD1d tetramers loaded with PI57 stained 10-23% of NKT cells in an NKT cell line (FIG. 7D). 92% of the PI57-CD1d tetramer+ cells were CD4$^-$ (DN). This strongly suggests that PI57 bound to CD1d was directly recognized by the TCR of a population of NKT cells. Finally, human NKT cells were also activated by PI57, since NKT cells lines (FIG. 7E) as well as a Vα24+NKT cell clone (BM2a.3) (FIG. 7F) responded to this glycolipid. The response was also directly induced, since plate bound CD1d loaded with PI57 induced IFN-γ in BM2a.3 cells (FIG. 7G). Taken together, these results indicated that both mouse and human NKT cells were directly activated by PI57, an *H. pylori* glycolipid, in a CD1d restricted manner.

DISCUSSION

As described herein, we show that infection of two-week-old suckling pups with influenza A virus H3N1 protected against the subsequent development of allergen-induced AHR, whereas infection of adult (eight-week-old) mice with H3N1 did not protect against the subsequent development of AHR. The protective effect H3N1 in suckling mice was associated with the maturation and expansion of a specific subset of NKT cells, which suppressed the development of allergen-induced AHR, demonstrated by adoptive transfer of these NKT cells into normal allergen-sensitized adult mice. The protective NKT cell subset required T-bet, as the NKT cells had to be derived from T-bet$^+$ mice, produced IFN-γ, and was present in NKT cell populations enriched for DN (CD4$^-$) NKT cells. Adoptive transfer of the protective NKT cell population was associated with the expansion of allergen-specific Foxp3$^+$ T$_{Reg}$ cells, suggesting that the suppressive effect was mediated by Foxp3$^+$ T$_{Reg}$ cells. Moreover the protective effect of H3N1 infection could be replicated by treating suckling mice with NKT cell-activating glycolipids from *H. pylori* or with α-C-GalCer. These studies are particularly important not only because they characterize an NKT cell population that suppresses AHR, but also because they provide a mechanism for the Hygiene Hypothesis, and for epidemiological studies indicating that infection with respiratory viruses (9) and *H. pylori* (2, 3) protect against the development of asthma.

NKT cells comprise a small subset of T lymphocytes that share characteristics with NK cells and conventional T cells, with potent functions in modulating immunity that have only recently become appreciated (33). NKT cells express a relatively unique transcription factor, PLZF, specific for NKT cells (34) and other innate or activated T cells (35), and an invariant TCR, Vα14Jα18 in mice and Vα24 in humans, and are restricted by the MHC class I-like molecule, CD1d. The conservation of this invariant TCR across many mammalian species suggests that it is a pattern recognition receptor, and that NKT cells play an important role in innate immunity. Activation of NKT cells through this invariant TCR results in the rapid production of large amounts of cytokines, including IL-4 and IFN-γ, particularly from mature NKT cells found in adult mice and humans. In contrast, NKT cells in neonates or in cord blood are immature, and produce only small amounts of cytokines (36, 37). Nevertheless, the ability of mature NKT cells to rapidly produce very large quantities of cytokines endows that NKT cell with the capacity to play very important regulatory roles in autoimmunity, cancer, asthma and infectious diseases (38).

NKT cells participate in immune responses to a growing list of infectious microorganisms, driven either by direct TCR recognition of specific glycolipids expressed by microorganisms, as in the case of *Borrelia burgdorferi* (39) and *Sphingomonas paucimobilis* (32, 40), or by indirect responses to cytokines released by activated dendritic cells (DCs), as in the case of *Salmonella typhimurium* (41), *E. coli, S. aureus, L. monocytogenes* (42) and *Mycobacteria tuberculosis* (43, 44). During influenza A infection in adult mice, NKT cells abolished the suppressive activity of influenza A-induced myeloid-derived suppressor cells, thereby enhancing survival (18). Our current studies also indicate that NKT cells can respond during infection with influenza A, and to glycolipids (PI57) produced by *H. pylori*, resulting in inhibitory effects on immunity, though primarily in young mice. The capacity of *H. pylori* glycolipids to activate a regulatory NKT cell subset but only in young mice can also explain the protective effects of *H. pylori* infection in neonatal but not older mice against gastritis and malignant metaplasia (45), as well as the observation that only wild-type and not cholesterol-α-glucosyltransferase deficient *H.*

*pylori* can infect the gastric mucosa of mice (28), given that cholesterol-α-glucosyltransferase is required for synthesis of PI57 (46). Finally, as demonstrated herein, the structure and function of PI57 is unique, since it includes a cholesterol containing tail distinct from previously described NKT cell ligands, and since it represents the first demonstration of cholesterol as a target for TCR recognition.

NKT cells thus react to a diverse group of pathogens, by functioning as an innate immune cell that can sense and rapidly respond to the presence of infectious agents. The capacity to respond to such pathogens however, may be limited in neonates and young children due to limited numbers and to the immaturity of NKT cells (36, 37). On the other hand, the immaturity of NKT cells in young children may provide an opportunity for infection and therapeutic intervention to influence the subset composition of NKT cells, thereby preventing the development of asthma and allergy.

In asthma, NKT cells have been suggested to play a very important pathogenic role (20, 47). This idea has become controversial, since some patients, particularly those with mild or well-controlled asthma, have few detectable pulmonary NKT cells, although patients with severe, poorly controlled asthma have a significant increase in pulmonary NKT cells (19, 48, 49). Nevertheless, in many distinct mouse models of asthma, the presence of specific NKT cell subsets was required for the development of AHR. For example, in allergen induced AHR, $CD4^+$ $IL-17RB^+$ NKT cells are required (19, 20, 50, 51); in ozone induced AHR, an $NK1.1^-$, IL-17 producing subset is required (21); and in Sendai virus induced AHR a $CD4^+$ NKT cell population that interacts with alternatively activated alveolar macrophages is required (22). While previous studies have suggested that some NKT cells (DN NKT cells) could not induce AHR (50), as described herein for the first time, a population of NKT cells, enriched for a DN, T-bet-dependent and IFN-γ producing subset, has a potent regulatory role, suppressing the development of AHR. Although previous studies have suggested an inhibitory role for NKT cells in asthma, since adoptive transfer of NKT cells acutely activated with α-GalCer (1 hr prior to transfer) could inhibit the development of experimental asthma in a C57BL/6 mouse model (52), the current studies described herein are quite distinct. Instead, we showed that H3N1 infection in suckling mice expanded a population of NKT cells that when examined 42 days after infection, specifically suppressed allergen-induced AHR, without the need for acute activation with exogenous glycolipids.

While H3N1 infection affects many different cell types, the fact that the protective effect of H3N1 infection could be transferred with purified NKT cells, and the fact that the protective effect could be replicated by treatment of suckling mice with α-C-GalCer or a glycolipid from *H. pylori* (PI57) that specifically activated NKT cells in a CD1d restricted fashion, strongly suggests that the protective effect of H3N1 infection in young mice was primarily mediated by a subset of NKT cells. The NKT cell subset activated by PI57 in suckling mice appeared to be a subset of invariant NKT cells, since DN NKT cells in suckling mice expanded after treatment with PI57, and since CD1d tetramers loaded with PI57 could stain NKT cells. The precise mechanism by which the DN NKT cells suppressed AHR can involve the preferential production of IFN-γ but not IL-4, since DN NKT cells from H3N1 infected suckling T-bet$^{-/-}$ mice failed to inhibit AHR. A role for IFN-γ is also supported by our observations described herein that treatment of suckling mice with α-C-GalCer, which preferentially induces IFN-γ (26), also prevented the development of OVA-induced AHR 42 days later, whereas treatment with α-GalCer or with *Sphingomonas* glycolipid (PBS30) did not.

The "regulatory" NKT cells mediating the inhibitory effect of H3N1 and of PI57 and α-C-GalCer may be similar to previously described DN NKT cells that protected against the development of type I diabetes in humans and in mice (53, 54), or to IFN-γ producing NKT cells that were required for allograft tolerance (55) or to IL-4 producing NKT cells that induced $T_{Reg}$ cells in the prevention of graft versus host disease (56-58). In our experiments, increased numbers of both natural and adaptive OVA-specific $T_{Reg}$ cells were associated with the regulatory NKT cells, and were blocked by treatment with anti-CD25 mAb (FIGS. 4F and 4G). Moreover, our studies are the first to demonstrate the existence of a subpopulation of NKT cells that can suppress the effects of other subpopulations of NKT cells that enhance the development of experimental asthma. These results suggest that a balance exists between NKT cells that induce, and those that protect against, AHR, and that stimulation with H3N1, α-C-GalCer or with *H. pylori* glycolipids, but not a *Sphingomas* glycolipid or α-GalCer, can selectively expand this regulatory NKT cell population, but only in young mice. The inability of α-GalCer to protective may be due to the fact, without wishing to be bound or limited by theory, that it non-selectively stimulates all invariant NKT cells, or because it may anergize NKT cells, including suppressive populations. The data described herein support the idea that under normal pathogen free conditions, $CD4^+$ NKT cells that induce AHR predominate, but that in very young mice, exposure to Th1-skewing reagents that can alter the composition of NKT cell subpopulations can change subsequent lung immunity.

Therefore, it appears that the balance between $CD4^+$ versus regulatory, presumably DN, NKT cells is determined or imprinted early in life, but might be influenced by exposure to specific types of infections, particularly those that can affect NKT cells. In our studies described herein, H3N1 infection in two-week-old pups activated the immature NKT cells and preferentially expanded a DN NKT cell subset. In addition, our studies indicate that α-C-GalCer and glycolipids from *H. pylori* can profoundly affect this NKT cell subpopulation, which may explain epidemiological studies showing an association of *H. pylori* infection with protection against asthma (2, 3). Although these studies were performed in mice, which mature from neonates to adults in only 35 days versus many years in humans, taken together, our results indicate that infection with certain microorganisms can prevent the subsequent development of asthma and allergy by expanding the relative proportion of a specific subset of NKT cells, thus providing an immunological mechanism for the Hygiene Hypothesis. Finally, these results indicate that treatment of children with compounds such of α-C-GalCer and others derived from microorganisms such as *H. pylori* can expand this regulatory NKT cell subset and be effective in preventing the development of asthma and other inflammatory disorders.

REFERENCES

1. Strachan, D. P. 1989. Hay fever, hygiene, and household size. BMJ 299:1259-1260.
2. Matricardi, P., Rosmini, F., Riondino, S., Fortini, M., Ferrigno, L., Rapicetta, M., and Bonini, S. 2000. Exposure to foodborne and orofecal microbes versus airborne viruses in relation to atopy and allergic asthma: epidemiological study. BMJ 320:412-417.

3. Reibman, J., Marmor, M., Filner, J., Fernandez-Beros, M. E., Rogers, L., Perez-Perez, G. I., and Blaser, M. J. 2008. Asthma is inversely associated with *Helicobacter pylori* status in an urban population. PLoS One 3:e4060.
4. Braun-Fahrlander, C., Riedler, J., Herz, U., Eder, W., Waser, M., Grize, L., Maisch, S., Carr, D., Gerlach, F., Bufe, A., et al. 2002. Environmental exposure to endotoxin and its relation to asthma in school-age children. N Engl J Med 347:869-877.
5. Conrad, M. L., Ferstl, R., Teich, R., Brand, S., Blumer, N., Yildirim, A. O., Patrascan, C. C., Hanuszkiewicz, A., Akira, S., Wagner, H., et al. 2009. Maternal TLR signaling is required for prenatal asthma protection by the non-pathogenic microbe *Acinetobacter lwoffii* F78. J Exp Med 206:2869-2877.
6. Matricardi, P. M., Rosmini, F., Ferrigno, L., Nisini, R., Rapicetta, M., Chionne, P., Stroffolini, T., Pasquini, P., and D'Amelio, R. 1997. Cross sectional retrospective study of prevalence of atopy among Italian military students with antibodies against hepatitis A virus. BMJ 314:999-1003.
7. Matricardi, P. M., Rosmini, F., Panetta, V., Ferrigno, L., and Bonini, S. 2002. Hay fever and asthma in relation to markers of infection in the United States. J Allergy Clin Immunol 110:381-387.
8. Jackson, D. J., Gangnon, R. E., Evans, M. D., Roberg, K. A., Anderson, E. L., Pappas, T. E., Printz, M. C., Lee, W. M., Shult, P. A., Reisdorf, E., et al. 2008. Wheezing rhinovirus illnesses in early life predict asthma development in high-risk children. Am J Respir Crit Care Med 178:667-672.
9. Martinez, F. D., Wright, A. L., Taussig, L. M., Holberg, C. J., Halonen, M., Morgan, W. J., and Associates, G. H. 1995. Asthma and wheezing in the first six years of life. New Engl. J. Med. 332:133-138.
10. von Mutius, E., Martinez, F. D., Fritzsch, C., Nicolai, T., Roell, G., and Thiemann, H. H. 1994. Prevalence of asthma and atopy in two areas of West and East Germany. Am J Respir Crit Care Med 149:358-364.
11. Tsitoura, D. C., Kim, S., Dabbagh, K., Berry, G., Lewis, D. B., and Umetsu, D. T. 2000. Respiratory infection with influenza A virus interferes with the induction of tolerance to aeroallergens. J. Immunol. 165:3484-3491.
12. Dahl, M., Dabbagh, K., Liggitt, D., Kim, S., and Lewis, D. 2004. Viral-induced T helper type 1 responses enhance allergic disease by effects on lung dendritic cells. Nat Immunol 5:337-343.
13. Marsland, B., Harris, N., Camberis, M., Kopf, M., Hook, S., and Le Gros, G. 2004. Bystander suppression of allergic airway inflammation by lung resident memory CD8+ T cells. Proc Natl Acad Sci USA 101:6116-6121.
14. Wohlleben, G., Muller, J., Tatsch, U., Hambrecht, C., Herz, U., Renz, H., Schmitt, E., Moll, H., and Erb, K. 2003. Influenza A virus infection inhibits the efficient recruitment of Th2 cells into the airways and the development of airway eosinophilia. J Immunol 170:4601-4611.
15. Glezen, W. P., Greenberg, S. B., Atmar, R. L., Piedra, P. A., and Couch, R. B. 2000. Impact of respiratory virus infections on persons with chronic underlying conditions. JAMA 283:499-505.
16. Miller, E. K., Griffin, M. R., Edwards, K. M., Weinberg, G. A., Szilagyi, P. G., Staat, M. A., Iwane, M. K., Zhu, Y., Hall, C. B., Fairbrother, G., et al. 2008. Influenza burden for children with asthma. Pediatrics 121:1-8.
17. Jain, S., Kamimoto, L., Bramley, A. M., Schmitz, A. M., Benoit, S. R., Louie, J., Sugerman, D. E., Druckenmiller, J. K., Ritger, K. A., Chugh, R., et al. 2009. Hospitalized patients with 2009 H1N1 influenza in the United States, April-June 2009. N Engl J Med 361:1935-1944.
18. De Santo, C., Salio, M., Masri, S. H., Lee, L. Y., Dong, T., Speak, A. O., Porubsky, S., Booth, S., Veerapen, N., Besra, G. S., et al. 2008. Invariant NKT cells reduce the immunosuppressive activity of influenza A virus-induced myeloid-derived suppressor cells in mice and humans. J Clin Invest 118:4036-4048.
19. Matangkasombut, P., Pichavant, M., Dekruyff, R. H., and Umetsu, D. T. 2009. Natural killer T cells and the regulation of asthma. Mucosal Immunol 2:383-392.
20. Akbari, O., Stock, P., Meyer, E., Kronenberg, M., Sidobre, S., Nakayama, T., Taniguchi, M., Grusby, M. J., DeKruyff, R. H., and Umetsu, D. T. 2003. Essential role of NKT cells producing IL-4 and IL-13 in the development of allergen-induced airway hyperreactivity. Nature Medicine 9:582-588.
21. Pichavant, M., Goya, S., Meyer, E. H., Johnston, R. A., Kim, H. Y., Matangkasombut, P., Zhu, M., Iwakura, Y., Savage, P. B., Dekruyff, R. H., et al. 2008. Ozone exposure in a mouse model induces airway hyperreactivity that requires the presence of natural killer T cells and IL-17. J Exp Med 205:385-393.
22. Kim, E. Y., Battaile, J. T., Patel, A. C., You, Y., Agapov, E., Grayson, M. H., Benoit, L. A., Byers, D. E., Alevy, Y., Tucker, J., et al. 2008. Persistent activation of an innate immune response translates respiratory viral infection into chronic lung disease. Nat Med 14:633-640.
23. Townsend, M. J., Weinmann, A. S., Matsuda, J. L., Salomon, R., Farnham, P. J., Biron, C. A., Gapin, L., and Glimcher, L. H. 2004. T-bet regulates the terminal maturation and homeostasis of NK and Valphal4i NKT cells. Immunity 20:477-494.
24. Kim, H. Y., Pichavant, M., Matangkasombut, P., Koh, Y. I., Savage, P. B., DeKruyff, R. H., and Umetsu, D. T. 2009. The development of airway hyperreactivity in T-bet-deficient mice requires CD1d-restricted NKT cells. J Immunol 182:3252-3261.
25. Schmieg, J., Yang, G., Franck, R. W., and Tsuji, M. 2003. Superior protection against malaria and melanoma metastases by a C-glycoside analogue of the natural killer T cell ligand alpha-Galactosylceramide. J Exp Med 198:1631-1641.
26. Fujii, S., Shimizu, K., Hemmi, H., Fukui, M., Bonito, A. J., Chen, G., Franck, R. W., Tsuji, M., and Steinman, R. M. 2006. Glycolipid alpha-C-galactosylceramide is a distinct inducer of dendritic cell function during innate and adaptive immune responses of mice. Proc Natl Acad Sci USA 103:11252-11257.
27. Li, X., Chen, G., Garcia-Navarro, R., Franck, R. W., and Tsuji, M. 2009. Identification of C-glycoside analogues that display a potent biological activity against murine and human invariant natural killer T cells. Immunology 127:216-225.
28. Wunder, C., Churin, Y., Winau, F., Warnecke, D., Vieth, M., Lindner, B., Zahringer, U., Mollenkopf, H. J., Heinz, E., and Meyer, T. F. 2006. Cholesterol glucosylation promotes immune evasion by *Helicobacter pylori*. Nat Med 12:1030-1038.
29. Linz, B., Balloux, F., Moodley, Y., Manica, A., Liu, H., Roumagnac, P., Falush, D., Stamer, C., Prugnolle, F., van der Merwe, S. W., et al. 2007. An African origin for the intimate association between humans and *Helicobacter pylori*. Nature 445:915-918.

30. Hirai, Y., Hague, M., Yoshida, T., Yokota, K., Yasuda, T., and Oguma, K. 1995. Unique cholesteryl glucosides in *Helicobacter pylori*: composition and structural analysis. J Bacteriol 177:5327-5333.
31. Mattner, J., Debord, K. L., Ismail, N., Goff, R. D., Cantu, C., 3rd, Zhou, D., Saint-Mezard, P., Wang, V., Gao, Y., Yin, N., et al. 2005. Exogenous and endogenous glycolipid antigens activate NKT cells during microbial infections. Nature 434:525-529.
32. Kinjo, Y., Wu, D., Kim, G., Xing, G.-W., Poles, M., Ho, D. D., Tsuji, M., Kawahara, K., Wong, C.-H., and Kronenberg, M. 2005. Recognition of bacterial glycosphingolipids by natural killer T cells. Nature 434:520-525.
33. Bendelac, A., Savage, P. B., and Teyton, L. 2007. The biology of NKT cells. Annu Rev Immunol 25:297-336.
34. Savage, A. K., Constantinides, M. G., Han, J., Picard, D., Martin, E., Li, B., Lantz, O., and Bendelac, A. 2008. The transcription factor PLZF directs the effector program of the NKT cell lineage. Immunity 29:391-403.
35. Kreslaysky, T., Savage, A. K., Hobbs, R., Gounari, F., Bronson, R., Pereira, P., Pandolfi, P. P., Bendelac, A., and von Boehmer, H. 2009. TCR-inducible PLZF transcription factor required for innate phenotype of a subset of gammadelta T cells with restricted TCR diversity. Proc Natl Acad Sci USA 106:12453-12458.
36. Kadowaki, N., Antonenko, S., Ho, S., Rissoan, M. C., Soumelis, V., Porcelli, S. A., Lanier, L. L., and Liu, Y. J. 2001. Distinct cytokine profiles of neonatal natural killer T cells after expansion with subsets of dendritic cells. J Exp Med 193:1221-1226.
37. D'Andrea, A., Goux, D., De Lalla, C., Koezuka, Y., Montagna, D., Moretta, A., Dellabona, P., Casorati, G., and Abrignani, S. 2000. Neonatal invariant Valpha24+ NKT lymphocytes are activated memory cells. Eur J Immunol 30:1544-1550.
38. Kronenberg, M. 2005. Toward an understanding of NKT cell biology: progress and paradoxes. Annu Rev Immunol 23:877-900.
39. Kinjo, Y., Tupin, E., Wu, D., Fujio, M., Garcia-Navarro, R., Benhnia, M. R., Zajonc, D. M., Ben-Menachem, G., Ainge, G. D., Painter, G. F., et al. 2006. Natural killer T cells recognize diacylglycerol antigens from pathogenic bacteria. Nat Immunol 7:978-986.
40. Mattner, J., DeBord, K. L., Ismail, N., Goff, R. D., III, C. C., Zhou, D., Saint-Mezard, P., Wang, V., Gao, Y., Yin, N., et al. 2005. Exogenous and endogenous glycolipid antigens activate NKT cells during microbial infections. Nature 434:525-529.
41. Brigl, M., Bry, L., Kent, S. C., Gumperz, J. E., and Brenner, M. B. 2003. Mechanism of CD1d-restricted natural killer T cell activation during microbial infection. Nat Immunol 4:1230-1237.
42. Kim, S., Lalani, S., Parekh, V. V., Vincent, T. L., Wu, L., and Van Kaer, L. 2008. Impact of bacteria on the phenotype, functions, and therapeutic activities of invariant NKT cells in mice. J Clin Invest 118:2301-2315.
43. Fischer, K., Scotet, E., Niemeyer, M., Koebernick, H., Zerrahn, J., Maillet, S., Hurwitz, R., Kursar, M., Bonneville, M., Kaufmann, S. H., et al. 2004. Mycobacterial phosphatidylinositol mannoside is a natural antigen for CD1d-restricted T cells. Proc Natl Acad Sci USA 101:10685-10690.
44. Sada-Ovalle, I., Chiba, A., Gonzales, A., Brenner, M. B., and Behar, S. M. 2008. Innate invariant NKT cells recognize *Mycobacterium tuberculosis*-infected macrophages, produce interferon-gamma, and kill intracellular bacteria. PLoS Pathog 4:e1000239.
45. Arnold, I., Lee, J. Y., Amieva, M. R., Roers, A., Flavell, R. A., Sparwasser, T., and Muller, A. 2010. Tolerance rather than immunity protects from *Helicobacter pylori*-induced gastric preneoplasia. Gastroenterology ePub ahead of print:June 2010.
46. Lebrun, A. H., Wunder, C., Hildebrand, J., Churin, Y., Zahringer, U., Lindner, B., Meyer, T. F., Heinz, E., and Warnecke, D. 2006. Cloning of a cholesterol-alpha-glucosyltransferase from *Helicobacter pylori*. J Biol Chem 281:27765-27772.
47. Lisbonne, M., Diem, S., de Castro Keller, A., Lefort, J., Araujo, L., Hachem, P., Fourneau, J., Sidobre, S., Kronenberg, M., Taniguchi, M., et al. 2003. Cutting edge: invariant V alpha 14 NKT cells are required for allergen-induced airway inflammation and hyperreactivity in an experimental asthma model. J Immunol 171:1637-1641.
48. Akbari, O., Faul, J. L., Hoyte, E. G., Berry, G. J., Wahlstrom, J., Kronenberg, M., DeKruyff, R. H., and Umetsu, D. T. 2006. CD4+ invariant T-cell-receptor+ natural killer T cells in bronchial asthma. N Engl J Med 354:1117-1129.
49. Vijayanand, P., Seumois, G., Pickard, C., Powell, R. M., Angco, G., Sammut, D., Gadola, S. D., Friedmann, P. S., and Djukanovic, R. 2007. Invariant natural killer T cells in asthma and chronic obstructive pulmonary disease. N Engl J Med 356:1410-1422.
50. Stock, P., Lombardi, V., Kohlrautz, V., and Akbari, O. 2009. Induction of airway hyperreactivity by IL-25 is dependent on a subset of invariant NKT cells expressing IL-17RB. J Immunol 182:5116-5122.
51. Terashima, A., Watarai, H., Inoue, S., Sekine, E., Nakagawa, R., Hase, K., Iwamura, C., Nakajima, H., Nakayama, T., and Taniguchi, M. 2008. A novel subset of mouse NKT cells bearing the IL-17 receptor B responds to IL-25 and contributes to airway hyperreactivity. J Exp Med 205:2727-2733.
52. Hachem, P., Lisbonne, M., Michel, M. L., Diem, S., Roongapinun, S., Lefort, J., Marchal, G., Herbelin, A., Askenase, P. W., Dy, M., et al. 2005. Alpha-galactosyl-ceramide-induced iNKT cells suppress experimental allergic asthma in sensitized mice: role of IFN-gamma. Eur J Immunol 35:2793-2802.
53. Wilson, S. B., Kent, S. C., Patton, K. T., Orban, T., Jackson, R. A., Exley, M., Porcelli, S., Schatz, D. A., Atkinson, M. A., Balk, S. P., et al. 1998. Extreme Th1 bias of invariant Vα24JaQ T cells in type 1 diabetes. Nature 391:177-181.
54. Diana, J., Griseri, T., Lagaye, S., Beaudoin, L., Autrusseau, E., Gautron, A. S., Tomkiewicz, C., Herbelin, A., Barouki, R., von Herrath, M., et al. 2009. NKT cell-plasmacytoid dendritic cell cooperation via OX40 controls viral infection in a tissue-specific manner. Immunity 30:289-299.
55. Seino, K. I., Fukao, K., Muramoto, K., Yanagisawa, K., Takada, Y., Kakuta, S., Iwakura, Y., Van Kaer, L., Takeda, K., Nakayama, T., et al. 2001. Requirement for natural killer T (NKT) cells in the induction of allograft tolerance. Proc Natl Acad Sci USA 98:2577-2581.
56. Zeng, D., Lewis, D., Dejbakhsh-Jones, S., Lan, F., Garcia-Ojeda, M., Sibley, R., and Strober, S. 1999. Bone marrow NK1.1(−) and NK1.1(+) T cells reciprocally regulate acute graft versus host disease. J Exp Med 189:1073-1081.
57. Lowsky, R., Takahashi, T., Liu, Y. P., Dejbakhsh-Jones, S., Grumet, F. C., Shizuru, J. A., Laport, G. G., Stockerl-Goldstein, K. E., Johnston, L. J., Hoppe, R. T., et al. 2005.

Protective conditioning for acute graft-versus-host disease. N Engl J Med 353:1321-1331.
58. Pillai, A. B., George, T. I., Dutt, S., and Strober, S. 2009. Host natural killer T cells induce an interleukin-4-dependent expansion of donor CD4+CD25+Foxp3+ T regulatory cells that protects against graft-versus-host disease. Blood 113:4458-4467.
59. Baumgarth, N., Brown, L., Jackson, D., and Kelso, A. 1994. Novel features of the respiratory tract T-cell response to influenza virus infection: lung T cells increase expression of gamma interferon mRNA in vivo and maintain high levels of mRNA expression for interleukin-5 (IL-5) and IL-10. J Virol 68:7575-7581.
60. Liu, Y., Goff, R. D., Zhou, D., Mattner, J., Sullivan, B. A., Khurana, A., Cantu, C., 3rd, Ravkov, E. V., Ibegbu, C. C., Altman, J. D., et al. 2006. A modified alpha-galactosyl ceramide for staining and stimulating natural killer T cells. *J Immunol Methods* 312:34-39.
61. Shimamura, M., Ohteki, T., Beutner, U., and MacDonald, H. R. 1997. Lack of directed V alpha 14-J alpha 281 rearrangements in NK1+ T cells. *Eur J Immunol* 27:1576-1579.
62. Brigl, M., van den Elzen, P., Chen, X., Meyers, J. H., Wu, D., Wong, C. H., Reddington, F., Illarianov, P. A., Besra, G. S., Brenner, M. B., et al. 2006. Conserved and heterogeneous lipid antigen specificities of CD1d-restricted NKT cell receptors. *J Immunol* 176:3625-3634.
63. Exley, M., Garcia, J., Balk, S. P., and Porcelli, S. 1997. Requirements for CD1d recognition by human invariant Valpha24+CD4-CD8- T cells. *J Exp Med* 186:109-120.
64. Gumperz, J. E., Miyake, S., Yamamura, T., and Brenner, M. B. 2002. Functionally distinct subsets of CD1d-restricted natural killer T cells revealed by CD1d tetramer staining. *J Exp Med* 195:625-636
65. Bukholm, G., Tannws, T., Nedenskov, P., Esbensen, Y., Gray, H. J., Hovig, T., Ariansen, S., and Guldvog, I. 1997. Colony variation of *Helicobacter pylori*: pathogenic potential is correlated to cell wall lipid composition. Scand. *J. Gastroenterol.* 32:445-454.
66. Lebrun, A. H, Wunder, C., Hildebrand, J., Churin, Y., Zahringer, U., Lindner, B., Meyer, T. F., Heinz, E., and Warnecke, D. 2006 Cloning of a cholesterol-alpha-glucosyltransferase from *Helicobacter pylori*. *J. Biol. Chem.* 281, 27765-27772.
67. Hirai, Y., Hague, M., Yoshida, T., Yokota, K., Yasuda, T., and Oguma, K. 1995. Unique cholesteryl glucosides in *Helicobacter pylori*: composition and structural analysis. *J. Bacteriology*, 177, 5327-33.

What is claimed is:

1. A method for the treatment of asthma in a subject in need thereof, the method comprising administering to a subject having asthma an effective amount of a compound of formula (I):

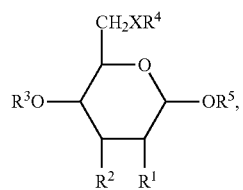

FORMULA (I)

wherein:
R$^1$ is OR$^3$, NH$_2$, or NHC(O)-alkyl, or together with R$^2$ forms a second bond between the carbons they are attached to;
R$^2$ is OR$^3$ or together with R$^1$ forms a second bond between the carbons they are attached to;
R$^3$ and R$^4$ are independently H, alkyl, alkenyl, alkynyl, acyl, PO$_3^{2-}$, each of which may be optionally substituted;
R$^5$ is

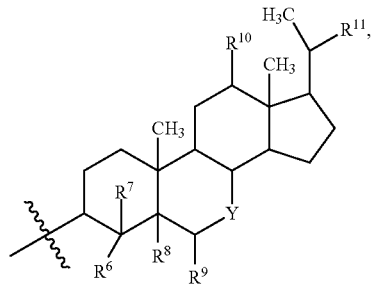

alkyl, alkenyl, alkynyl, or acyl, each of which may be optionally substituted;
R$^6$ and R$^7$ are both H or both alkyl;
R$^8$ is H or together with R$^9$ forms a second bond between the carbons to which they are attached;
R$^9$ is H, OR$^3$, or together with R$^8$ forms a second bond between the carbons to which they are attached;
R$^{10}$ is H, OH, alkyl, or O-alkyl, each of which may be optionally substituted;
R$^{11}$ is alkyl, alkenyl, or alkynyl, each of which may be optionally substituted;
X is O, or NH;
Y is CH$_2$, C(O), or CHOR$^3$; and
pharmaceutically acceptable salts thereof.

2. The method of claim 1, further comprising administering an effective amount of antigen presenting cells.

3. A method for the treatment of asthma in a subject in need thereof, the method comprising administering to a subject having asthma an NKT cell population contacted with an effective amount of a compound of formula (I):

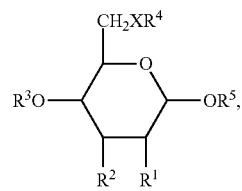

FORMULA (I)

wherein:
R$^1$ is OR$^3$, NH$_2$, or NHC(O)-alkyl, or together with R$^2$ forms a second bond between the carbons they are attached to;
R$^2$ is OR$^3$ or together with R$^1$ forms a second bond between the carbons they are attached to;
R$^3$ and R$^4$ are independently H, alkyl, alkenyl, alkynyl, acyl, PO$_3^{2-}$, each of which may be optionally substituted;

R⁵ is

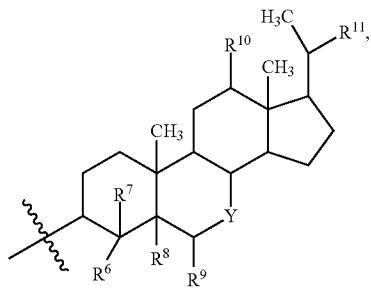

alkyl, alkenyl, alkynyl, or acyl, each of which may be optionally substituted;
R⁶ and R⁷ are both H or both alkyl;
R⁸ is H or together with R⁹ forms a second bond between the carbons to which they are attached;
R⁹ is H, OR³, or together with R⁸ forms a second bond between the carbons to which they are attached;
R¹⁰ is H, OH, alkyl, or O-alkyl, each of which may be optionally substituted;
R¹¹ is alkyl, alkenyl, or alkynyl, each of which may be optionally substituted;
X is O, or NH;
Y is CH₂, C(O), or CHOR³; and
pharmaceutically acceptable salts thereof.

4. The method of claim 3, wherein the contacting of the NKT cell population with the compound of formula (I) occurs in vitro, ex vivo, or in vivo.

5. The method of claim 3, wherein the contacting of the NKT cell population with the compound of formula (I) occurs in the presence of one or more antigen-presenting cells.

6. The method of claim 3, wherein the NKT cells are allogeneic NKT cells obtained from one or more donors.

7. The method of claim 3, wherein the NKT cells are autologous NKT cells.

8. A method for the treatment of asthma disease in a subject in need thereof, the method comprising:
a) isolating a plurality of immune cells from a first subject, wherein the immune cells comprise an NKT population;
b) contacting said immune cells with an effective amount of a compound of formula (I):

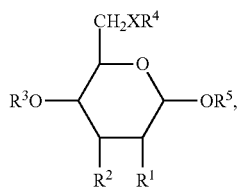

FORMULA (I)

wherein:
R¹ is OR³, NH₂, or NHC(O)-alkyl, or together with R² forms a second bond between the carbons they are attached to;
R² is OR³ or together with R¹ forms a second bond between the carbons they are attached to;
R³ and R⁴ are independently H, alkyl, alkenyl, alkynyl, acyl, PO₃²⁻, each of which may be optionally substituted;

R⁵ is

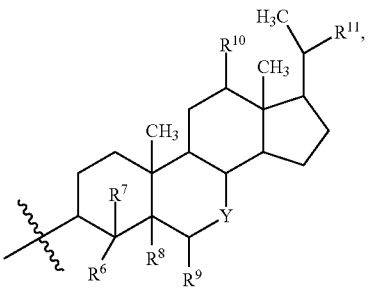

alkyl, alkenyl, alkynyl, or acyl, each of which may be optionally substituted;
R⁶ and R⁷ are both H or both alkyl;
R⁸ is H or together with R⁹ forms a second bond between the carbons to which they are attached;
R⁹ is H, OR³, or together with R⁸ forms a second bond between the carbons to which they are attached;
R¹⁰ is H, OH, alkyl, or O-alkyl, each of which may be optionally substituted;
R¹¹ is alkyl, alkenyl, or alkynyl, each of which may be optionally substituted;
X is O, or NH;
Y is CH₂, C(O), or CHOR³; and
pharmaceutically acceptable salts thereof; and
c) administering to a second subject an effective amount of the plurality of immune cells contacted with a compound of formula (I), wherein said second subject has asthma.

9. The method of claim 8, wherein the immune cells are contacted with the compound of formula (I) in an amount and time sufficient to expand an NKT cell population in the plurality of immune cells.

10. A method for the treatment of asthma in a subject in need thereof, the method comprising:
a. administering to a first subject an effective amount of a compound of formula (I):

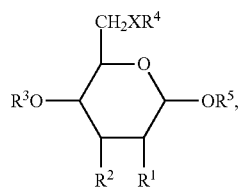

FORMULA (I)

wherein:
R¹ is OR³, NH₂, or NHC(O)-alkyl, or together with R² forms a second bond between the carbons they are attached to;
R² is OR³ or together with R¹ forms a second bond between the carbons they are attached to;
R³ and R⁴ are independently H, alkyl, alkenyl, alkynyl, acyl, PO₃²⁻, each of which may be optionally substituted;

$R^5$ is

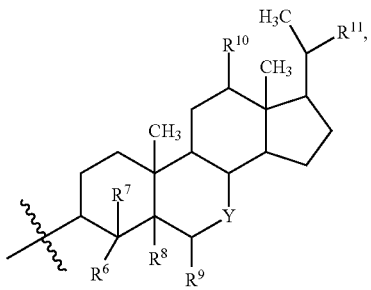

alkyl, alkenyl, alkynyl, or acyl, each of which may be optionally substituted;

$R^6$ and $R^7$ are both H or both alkyl;

$R^8$ is H or together with $R^9$ forms a second bond between the carbons to which they are attached;

$R^9$ is H, $OR^3$, or together with $R^8$ forms a second bond between the carbons to which they are attached;

$R^{10}$ is H, OH, alkyl, or O-alkyl, each of which may be optionally substituted;

$R^{11}$ is alkyl, alkenyl, or alkynyl, each of which may be optionally substituted;

X is O, or NH;

Y is $CH_2$, C(O), or $CHOR^3$; and pharmaceutically acceptable salts thereof; and b. isolating a plurality of immune cells from the first subject, wherein the immune cells comprise an NKT population;

c. administering to a second subject an effective amount of the plurality of immune cells isolated from the first subject contacted with a compound of formula (I), wherein said second subject has asthma.

11. The method of claim 8, wherein the first and second subject are the same subject.

12. The method of claim 3, wherein the first subject is a young subject or an infant subject.

13. The method of claim 8, wherein the first subject is less than 10 years of age.

14. The method of claim 8, wherein the plurality of immune cells further comprise antigen-presenting cells.

15. The method of claim 8, wherein the plurality of immune cells are isolated from the peripheral blood, bone marrow, thymus, or spleen of the first subject.

16. The method of claim 8, further comprising purifying an NKT cell population from the plurality of immune cells prior to the administration of the plurality of immune cells to the second subject.

17. The method of claim 16, wherein the purified NKT cell population has a $CD4^-$ $CD8^-$ phenotype.

18. The method of claim 1, wherein the compound of formula (I) is selected from cholesteryl-α-D-alloside; cholesteryl-α-D-glucoside; cholesteryl-α-D-mannoside; cholesteryl-α-D-guloside; cholesteryl-α-D-galactoside; cholesteryl-α-D-taloside; cholesteryl-α-D-glucosamine; cholesteryl-6-O-tetradecanoyl-α-D-alloside; cholesteryl-6-O-tetradecanoyl-α-D-glucoside; cholesteryl-6-O-tetradecanoyl-α-D-mannoside; cholesteryl-6-O-tetradecanoyl-α-D-guloside; cholesteryl-6-O-tetradecanoyl-α-D-galactoside; cholesteryl-6-O-tetradecanoyl-α-D-taloside; cholesteryl-6-O-tetradecanoyl-α-D-glucosamine; cholesteryl-6-phosphate-α-D-alloside; cholesteryl-6-phosphate-α-D-glucoside; cholesteryl-6-phosphate-α-D-mannoside; cholesteryl-6-phosphate-α-D-guloside; cholesteryl-6-phosphate-α-D-galactoside; cholesteryl-6-phosphate-α-D-taloside; cholesteryl-6-phosphate-α-D-glucosamine; cholesteryl-1,6-bisphosphate-α-D-alloside; cholesteryl-1,6-bisphosphate-α-D-glucoside; cholesteryl-1,6-bisphosphate-α-D-mannoside; cholesteryl-1,6-bisphosphate-α-D-guloside; cholesteryl-1,6-bisphosphate-α-D-galactoside; cholesteryl-1,6-bisphosphate-α-D-taloside; 7-beta-hydroxycholesteryl-α-D-alloside; 7-beta-hydroxycholesteryl-α-D-glucoside; 7-beta-hydroxycholesteryl-α-D-mannoside; 7-beta-hydroxycholesteryl-α-D-guloside; 7-beta-hydroxycholesteryl-α-D-galactoside; 7-beta-hydroxycholesteryl-α-D-taloside; 7-beta-hydroxycholesteryl-α-D-glucosamine; 7-beta-hydroxycholesteryl-6-O-tetradecanoyl-α-D-alloside; 7-beta-hydroxycholesteryl-6-O-tetradecanoyl-α-D-glucoside; 7-beta-hydroxycholesteryl-6-O-tetradecanoyl-α-D-mannoside; 7-beta-hydroxycholesteryl-6-O-tetradecanoyl-α-D-guloside; 7-beta-hydroxycholesteryl-6-O-tetradecanoyl-α-D-galactoside; 7-beta-hydroxycholesteryl-6-O-tetradecanoyl-α-D-taloside; 7-beta-hydroxycholesteryl-6-O-tetradecanoyl-α-D-glucosamine; 7-beta-hydroxycholesteryl-6-phosphate-α-D-alloside; 7-beta-hydroxycholesteryl-6-phosphate-α-D-glucoside; 7-beta-hydroxycholesteryl-6-phosphate-α-D-mannoside; 7-beta-hydroxycholesteryl-6-phosphate-α-D-guloside; 7-beta-hydroxycholesteryl-6-phosphate-α-D-galactoside; 7-beta-hydroxycholesteryl-6-phosphate-α-D-taloside; 7-beta-hydroxycholesteryl-6-phosphate-α-D-glucosamine; 7-beta-hydroxycholesteryl-1,6-bisphosphate-α-D-alloside; 7-beta-hydroxycholesteryl-1,6-bisphosphate-α-D-glucoside; 7-beta-hydroxycholesteryl-1,6-bisphosphate-α-D-mannoside; 7-beta-hydroxycholesteryl-1,6-bisphosphate-α-D-guloside; 7-beta-hydroxycholesteryl-1,6-bisphosphate-α-D-galactoside; 7-beta-hydroxycholesteryl-1,6-bisphosphate-α-D-taloside; 7-keto-cholesteryl-α-D-alloside; 7-keto-cholesteryl-α-D-glucoside; 7-keto-cholesteryl-α-D-mannoside; 7-keto-cholesteryl-α-D-guloside; 7-keto-cholesteryl-α-D-galactoside; 7-keto-cholesteryl-α-D-taloside; 7-keto-cholesteryl-α-D-glucosamine; 7-keto-cholesteryl-6-O-tetradecanoyl-α-D-alloside; 7-keto-cholesteryl-6-O-tetradecanoyl-α-D-glucoside; 7-keto-cholesteryl-6-O-tetradecanoyl-α-D-mannoside; 7-keto-cholesteryl-6-O-tetradecanoyl-α-D-guloside; 7-keto-cholesteryl-6-O-tetradecanoyl-α-D-galactoside; 7-keto-cholesteryl-6-O-tetradecanoyl-α-D-taloside; 7-keto-cholesteryl-6-O-tetradecanoyl-α-D-glucosamine; 7-keto-cholesteryl-6-phosphate-α-D-alloside; 7-keto-cholesteryl-6-phosphate-α-D-glucoside; 7-keto-cholesteryl-6-phosphate-α-D-mannoside; 7-keto-cholesteryl-6-phosphate-α-D-guloside; 7-keto-cholesteryl-6-phosphate-α-D-galactoside; 7-keto-cholesteryl-6-phosphate-α-D-taloside; 7-keto-cholesteryl-6-phosphate-α-D-glucosamine; 7-keto-cholesteryl-1,6-bisphosphate-α-D-alloside; 7-keto-cholesteryl-1,6-bisphosphate-α-D-glucoside; 7-keto-cholesteryl-1,6-bisphosphate-α-D-mannoside; 7-keto-cholesteryl-1,6-bisphosphate-α-D-guloside; 7-keto-cholesteryl-1,6-bisphosphate-α-D-galactoside; 7-keto-cholesteryl-1,6-bisphosphate-α-D-taloside; 6,7-dihydroxycholesteryl-α-D-alloside; 6,7-dihydroxycholesteryl-α-D-glucoside; 6,7-dihydroxycholesteryl-α-D-mannoside; 6,7-dihydroxycholesteryl-α-D-guloside; 6,7-dihydroxycholesteryl-α-D-galactoside; 6,7-dihydroxycholesteryl-α-D-taloside; 6,7-dihydroxycholesteryl-α-D-glucosamine; 6,7-dihydroxycholesteryl-6-O-tetradecanoyl-α-D-alloside; 6,7-dihydroxycholesteryl-6-O-tetradecanoyl-α-D-glucoside; 6,7-dihydroxycholesteryl-6-O-tetradecanoyl-α-D-mannoside; 6,7-dihydroxycholesteryl-6-O-tetradecanoyl-α-D-guloside; 6,7-dihydroxycholesteryl-6-O-tetradecanoyl-α-D-galactoside; 6,7-dihydroxycholesteryl-6-O-tetradecanoyl-α-D-taloside; 6,7-dihydroxycholesteryl-6-O-tetradecanoyl-α-D-glucosamine; 6,7-dihydroxycholesteryl-6-phosphate-α-D-alloside; 6,7-dihydroxycholesteryl-6-phosphate-α-D-glucoside; 6,7-dihydroxycholesteryl-6-phosphate-α-D-mannoside; 6,7-dihydroxycholesteryl-6-phosphate-α-D-guloside; 6,7-dihydroxycholesteryl-6-phosphate-α-D-galactoside; 6,7-dihydroxycholesteryl-6-phosphate-α-D-taloside; 6,7-dihydroxycholesteryl-6-phosphate-α-D-glucosamine; 6,7-dihydroxycholesteryl-1,6-bisphosphate-α-D-alloside; 6,7-dihydroxycholesteryl-1,6-bisphosphate-α-D-glucoside; 6,7-dihydroxycholesteryl-1,6-bisphosphate-α-D-mannoside; 6,7-dihydroxycholesteryl-1,6-bisphosphate-α-D-guloside; 6,7-dihydroxycholesteryl-1,6-bisphosphate-α-D-galactoside; and 6,7-dihydroxycholesteryl-1,6-bisphosphate-α-D-taloside.

19. The method of claim 1, wherein the compound of formula (I) is cholesteryl 6-O-tetradecanoyl-α-D-glucopyranoside.

20. The method of claim 1, wherein the asthma is allergic or non-allergic asthma.

21. A method for the treatment of asthma in a subject in need thereof, the method comprising administering to a subject having asthma an NKT cell population contacted with an effective amount of a compound of formula (VI):

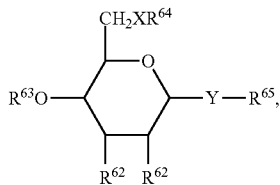

FORMULA (VI)

wherein:
$R^{61}$ is $OR^{63}$, $NH_2$, or NHC(O)-alkyl, or together with $R^{62}$ forms a second bond between the carbons they are attached to;
$R^{62}$ is $OR^{63}$ or together with $R^{61}$ forms a second bond between the carbons they are attached to;
$R^{63}$ and $R^{64}$ are independently H, alkyl, alkenyl, alkynyl, acyl, $PO_3^{2-}$, each of which may be optionally substituted;
$R^{65}$ is alkyl, alkenyl, alkynyl, acyl, fatty acid, or lipid each of which may be optionally substituted;
X is O, or NH;
Y is absent, or a linker; and
pharmaceutically acceptable salts thereof.

* * * * *

UNITED STATES PATENT AND TRADEMARK OFFICE
CERTIFICATE OF CORRECTION

PATENT NO. : 9,657,046 B2
APPLICATION NO. : 13/699436
DATED : May 23, 2017
INVENTOR(S) : Dale T. Umetsu et al.

It is certified that error appears in the above-identified patent and that said Letters Patent is hereby corrected as shown below:

In the Specification

At Column 1, Line numbers 20-23 should be changed to:
--This invention was made with government support under grant number AI068085 awarded by the National Institutes of Health. The Government has certain rights in the invention.--

Signed and Sealed this
Twenty-third Day of April, 2019

Andrei Iancu
*Director of the United States Patent and Trademark Office*

UNITED STATES PATENT AND TRADEMARK OFFICE
CERTIFICATE OF CORRECTION

Page 1 of 1

PATENT NO. : 9,657,046 B2
APPLICATION NO. : 13/699436
DATED : May 23, 2017
INVENTOR(S) : Dale T. Umetsu et al.

It is certified that error appears in the above-identified patent and that said Letters Patent is hereby corrected as shown below:

In the Specification

Column 1, Line numbers 20-23 should be changed to:
--This invention was made with Government support under grant number R01 AI68085, R01 HL62348, R01 AI026322, and RC1HL069507 awarded by the National Institutes of Health (NIH). The Government has certain rights in the invention.--

This certificate supersedes the Certificate of Correction issued April 23, 2019.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*